(12) United States Patent
Ahmad et al.

(10) Patent No.: US 10,786,177 B1
(45) Date of Patent: Sep. 29, 2020

(54) EXTRACTING AN ANALYE FROM A BREATH SAMPLE USING A SOLID POROUS STRUCTURE CONTAINING A REACTIVE MATERIAL

(71) Applicant: Invoy Holdings, LLC, Aliso Viejo, CA (US)

(72) Inventors: Lubna M. Ahmad, Chandler, AZ (US);
Zachary B. Smith, Phoenix, AZ (US);
Salman A. Ahmad, Chandler, AZ (US);
Connie Kim, Garden Grove, CA (US)

(73) Assignee: Invoy Holdings Inc., Irvine, CA (US)

( * ) Notice: Subject to any disclaimer, the term of this patent is extended or adjusted under 35 U.S.C. 154(b) by 0 days.

(21) Appl. No.: 16/414,487

(22) Filed: May 16, 2019

Related U.S. Application Data

(60) Provisional application No. 62/675,109, filed on May 22, 2018.

(51) Int. Cl.
*A61B 5/00* (2006.01)
*A61B 5/08* (2006.01)
*A61B 5/083* (2006.01)
*A61B 5/097* (2006.01)
*G01N 33/497* (2006.01)

(52) U.S. Cl.
CPC ............ *A61B 5/082* (2013.01); *A61B 5/0833* (2013.01); *A61B 5/0836* (2013.01); *A61B 5/097* (2013.01); *A61B 5/0059* (2013.01); *A61B 5/742* (2013.01); *G01N 33/497* (2013.01)

(58) Field of Classification Search
CPC ...................................................... A61B 5/082

USPC ......................................................... 436/167
See application file for complete search history.

(56) References Cited

U.S. PATENT DOCUMENTS

| | | | |
|---|---|---|---|
| 4,970,172 A * | 11/1990 | Kundu | .................... A61B 5/083 422/413 |
| 5,071,769 A | 12/1991 | Kundu et al. | |
| 5,174,959 A | 12/1992 | Kundu | |
| 8,349,400 B2 | 1/2013 | Ramsey et al. | |
| 9,533,136 B2 | 1/2017 | Midgette et al. | |
| 9,636,044 B2 | 5/2017 | Ahmad et al. | |

(Continued)

OTHER PUBLICATIONS

Xing et al. "Au-modified three-dimensional In2O3 inverse opals: synthesis and improved performance for acetone sensing toward diagnosis of diabetes" Nanoscale, 2015, 7, 13051 (Year: 2015).*

*Primary Examiner* — Christopher Adam Hixson
*Assistant Examiner* — Emily R. Berkeley
(74) *Attorney, Agent, or Firm* — Knobbe, Martens, Olson & Bear, LLP

(57) ABSTRACT

Various devices are disclosed for measuring the concentration of an analyte, such as acetone, in a breath sample. The disclosed devices include a disposable cartridge containing a reactive material that extracts the analyte from a breath sample passed through the cartridge. In some embodiments, the cartridge contains a solid, porous structure (such as a disk, bowl or puck) that contains the reactive material. The porous structure may be created by mixing reactive particles with resin particles, and then using a sintering process to transform the mixture into a solid structure. Also disclosed are devices for routing a breath sample through the cartridge during exhalation, and for analyzing a reaction in the cartridge to measure a concentration of the analyte.

19 Claims, 48 Drawing Sheets

(56) References Cited

U.S. PATENT DOCUMENTS

| | | |
|---|---|---|
| 9,696,241 B2 | 7/2017 | Mao et al. |
| 10,195,635 B2 | 2/2019 | Sporrer |
| 10,226,201 B2 | 3/2019 | Ahmad et al. |
| 2004/0180980 A1* | 9/2004 | Petter .................. B29C 64/153 522/2 |
| 2009/0275852 A1 | 11/2009 | Oki |
| 2013/0316070 A1 | 11/2013 | Patel |
| 2014/0276100 A1 | 9/2014 | Satterfiled et al. |

* cited by examiner

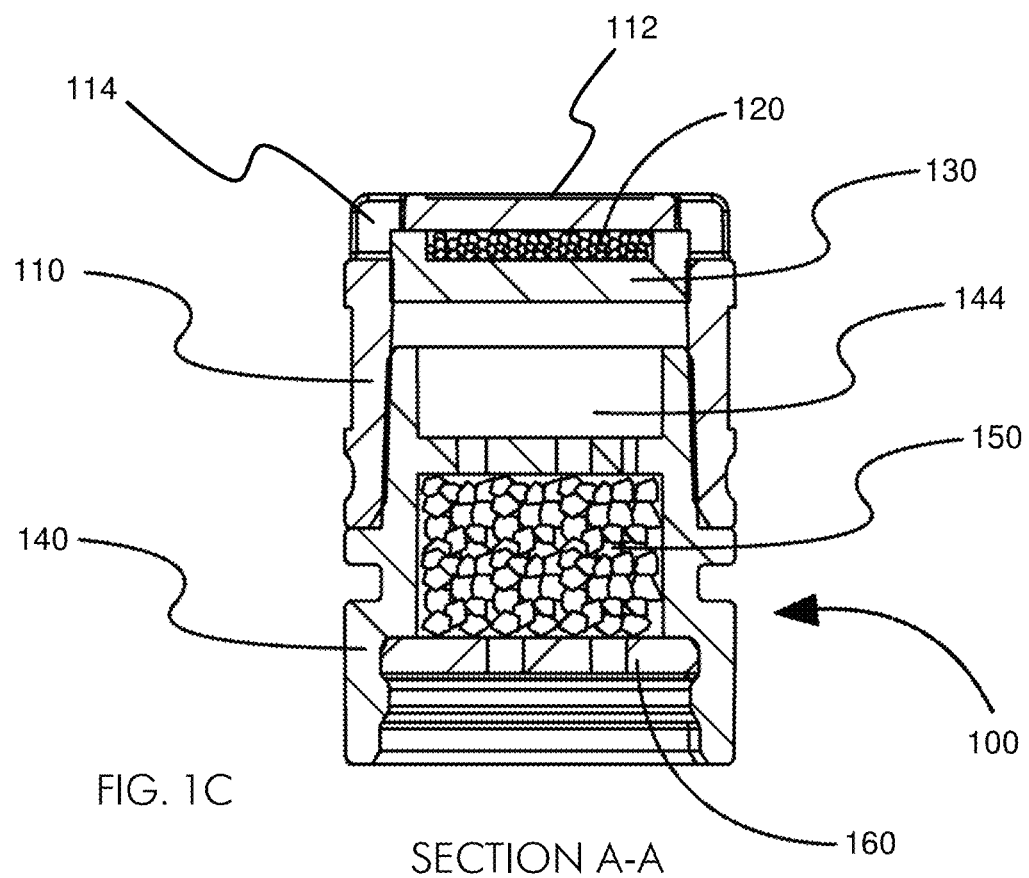
FIG. 1C  SECTION A-A
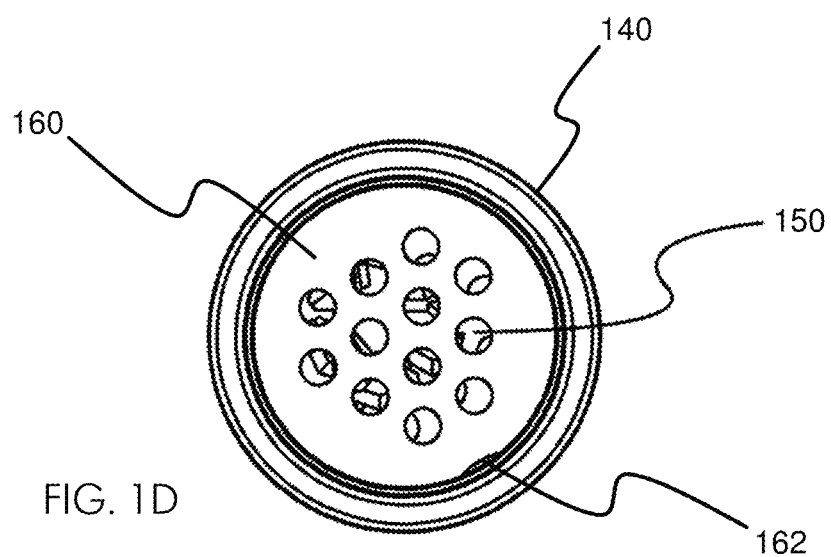
FIG. 1D

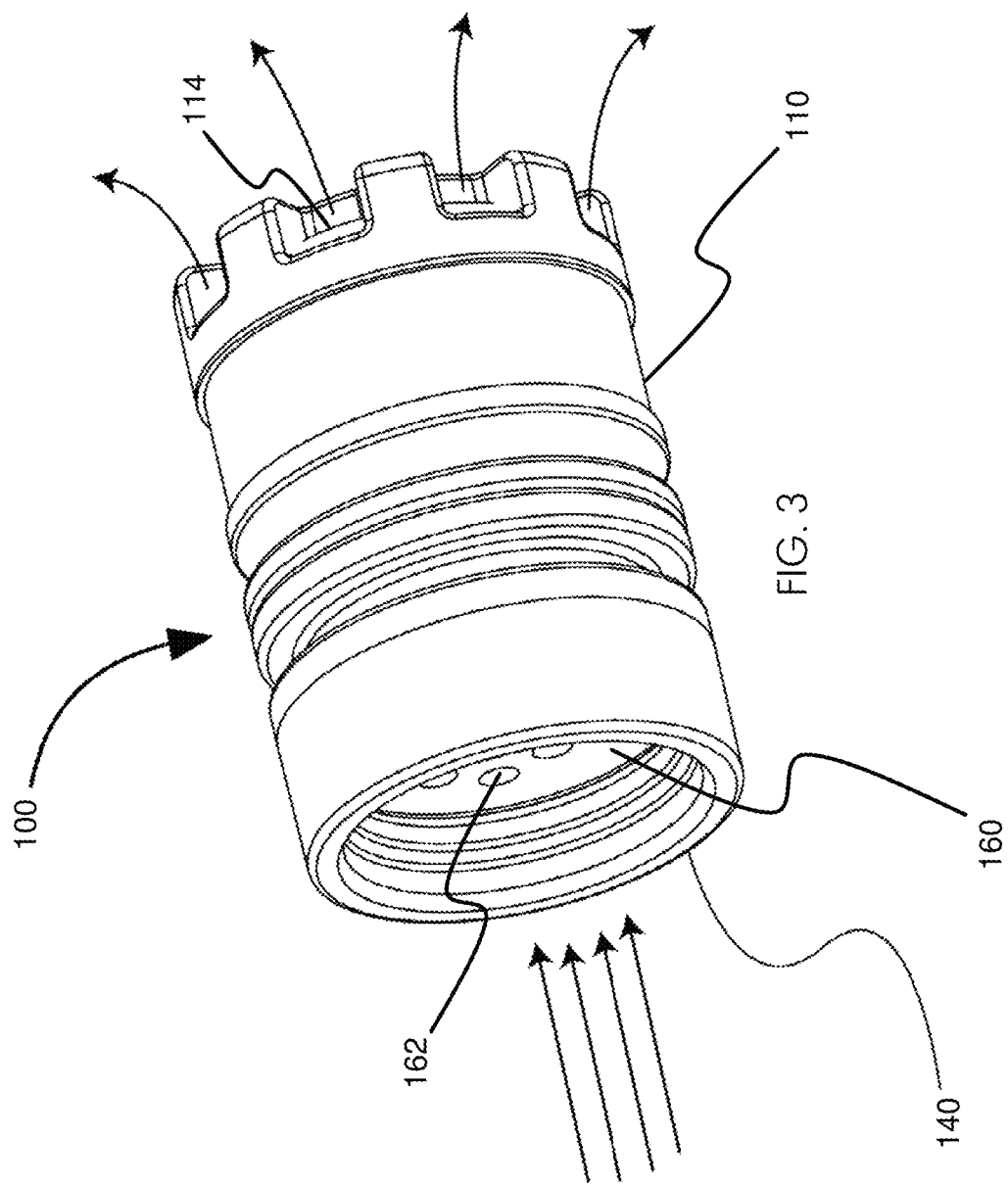

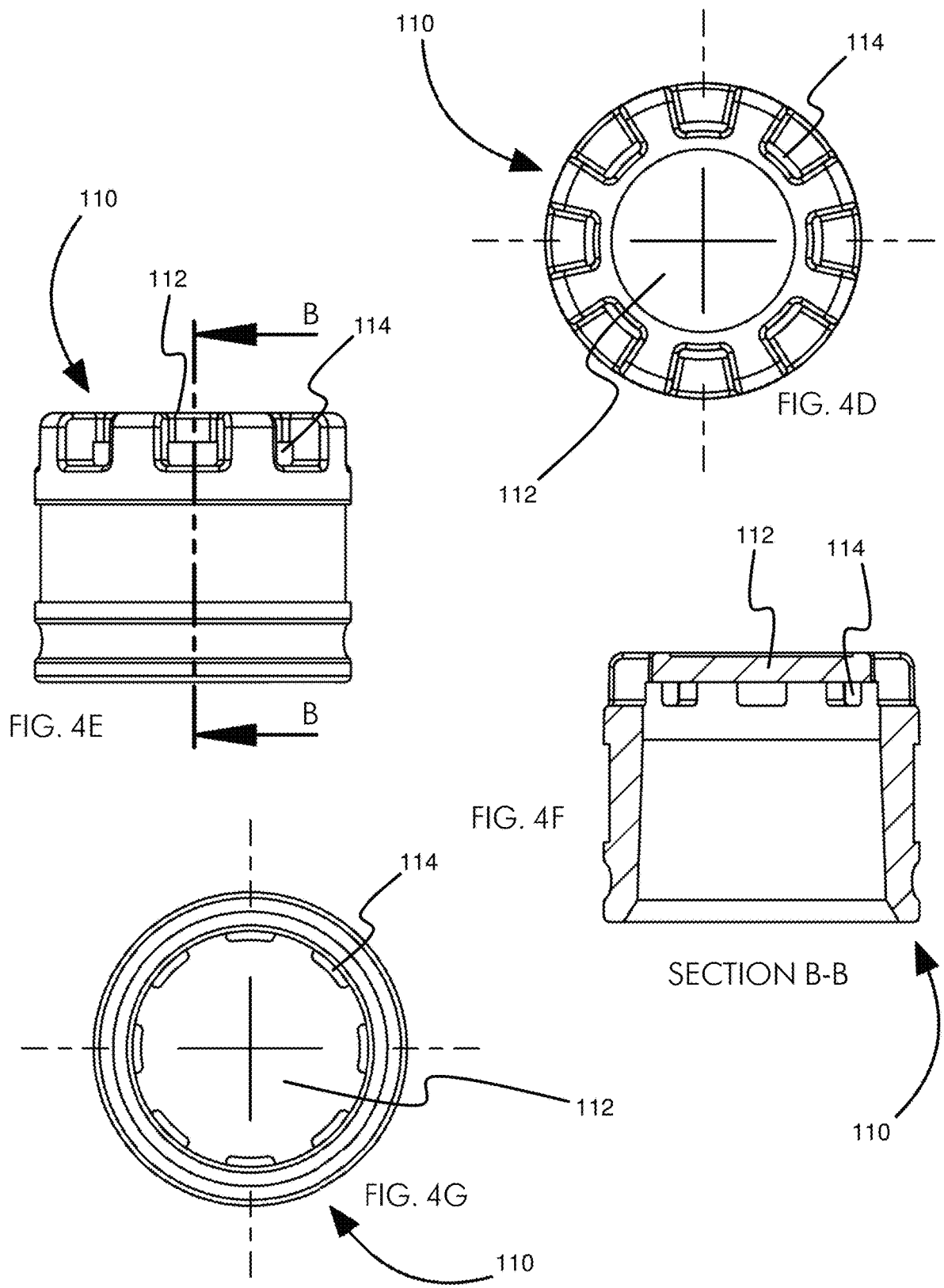

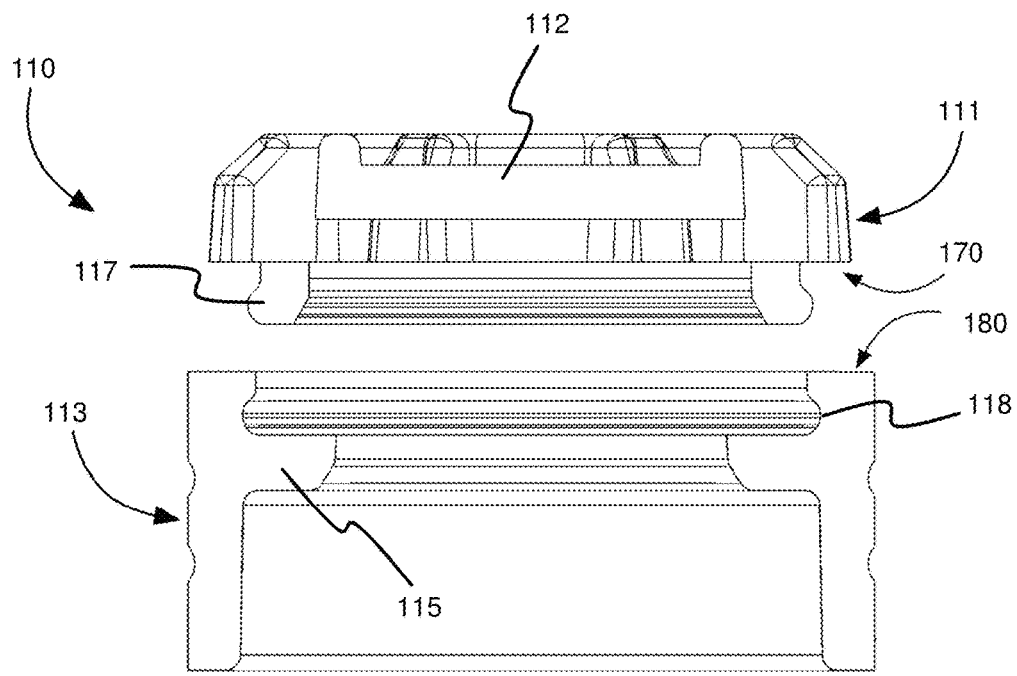
FIG. 4H
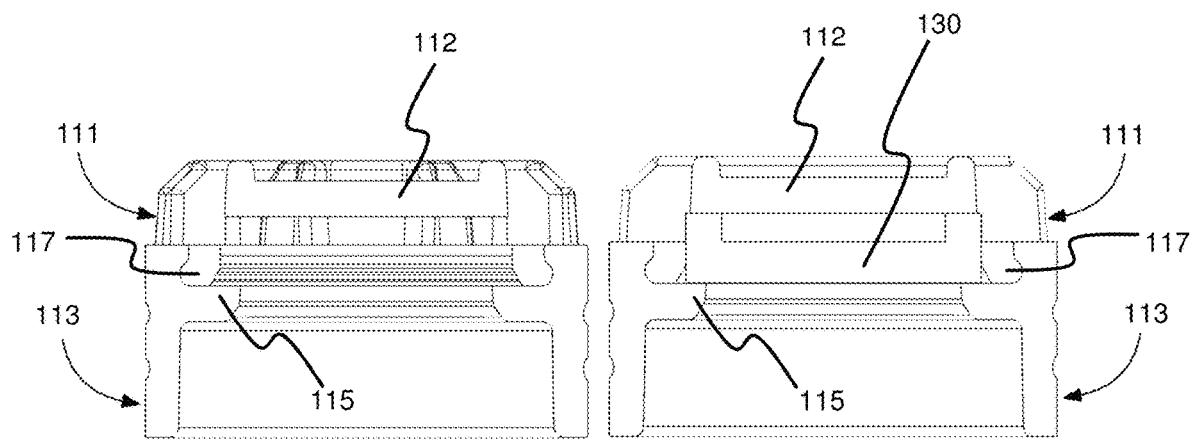
FIG. 4I
FIG. 4J

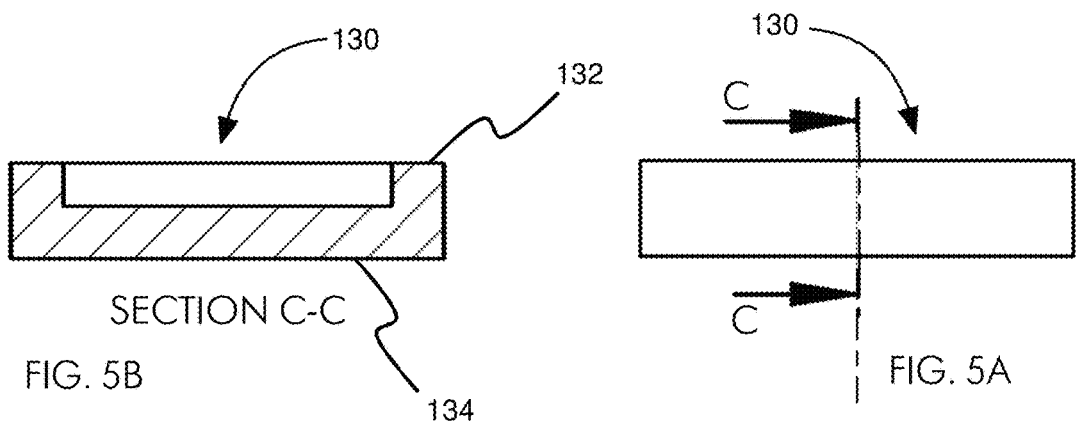
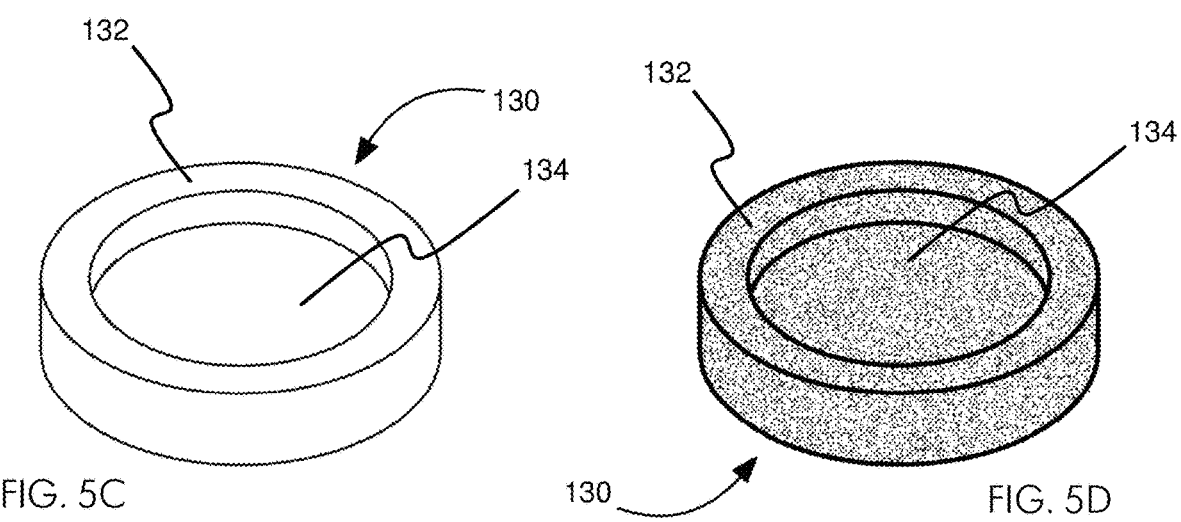
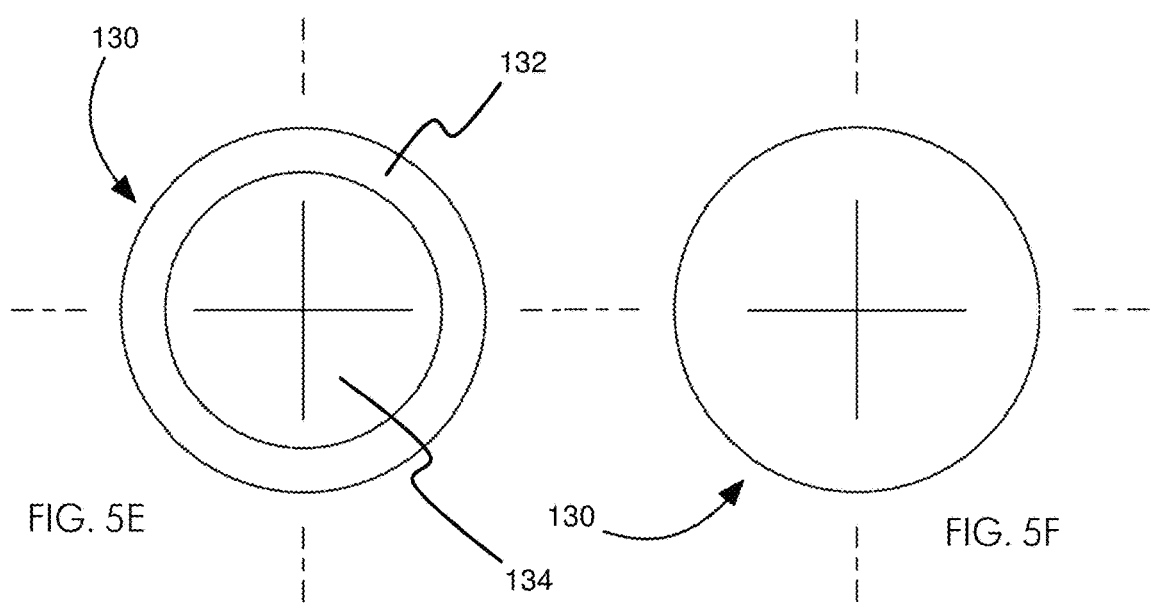

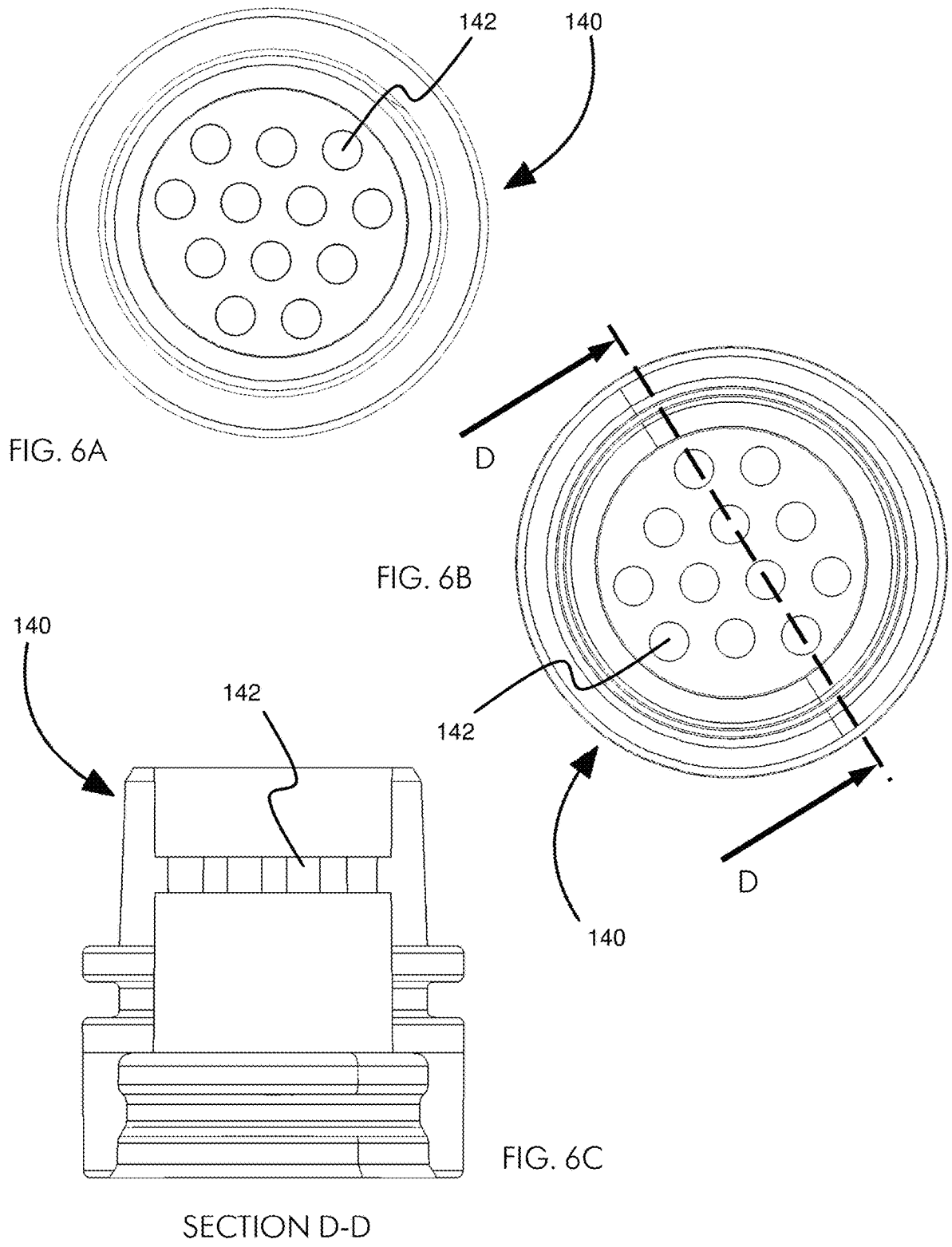

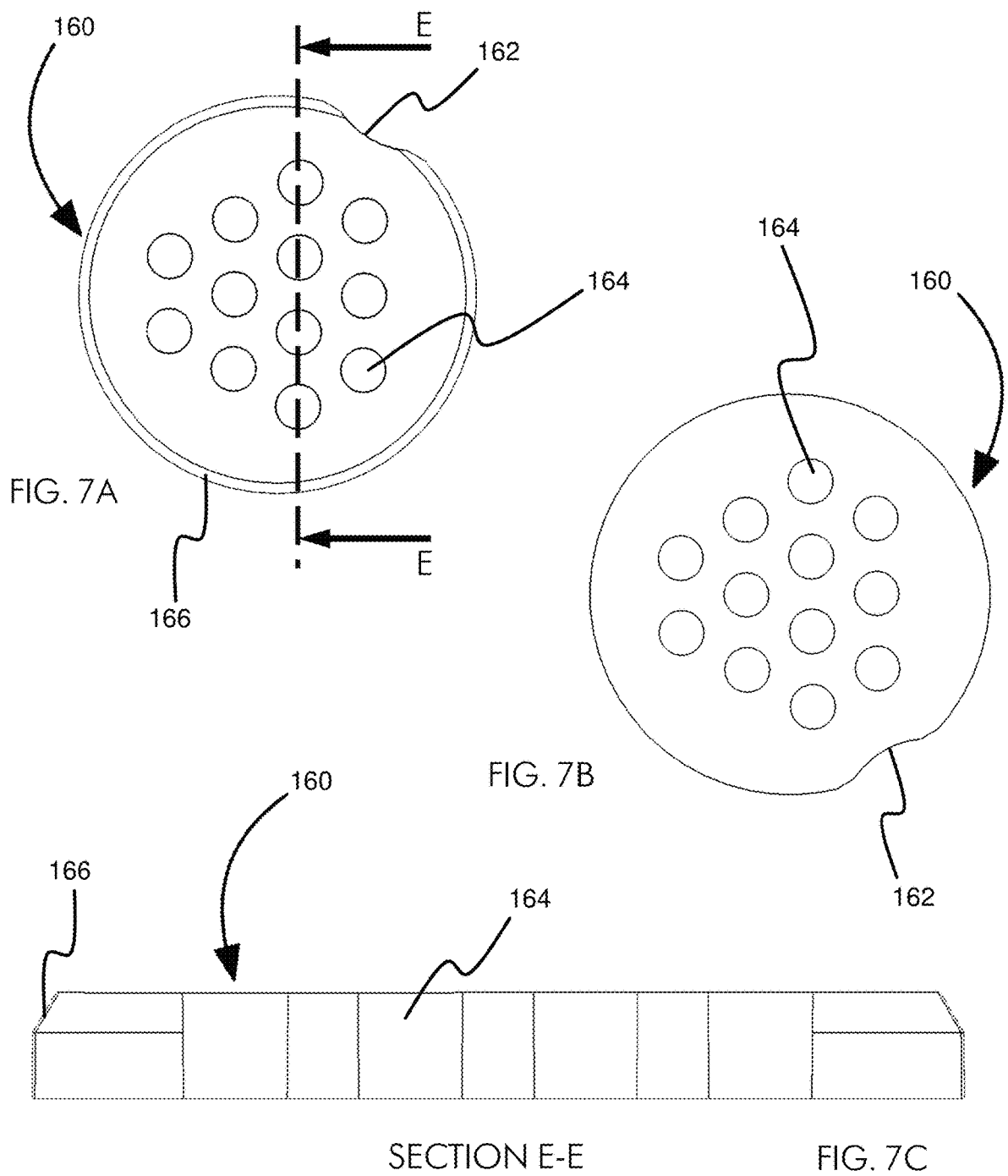

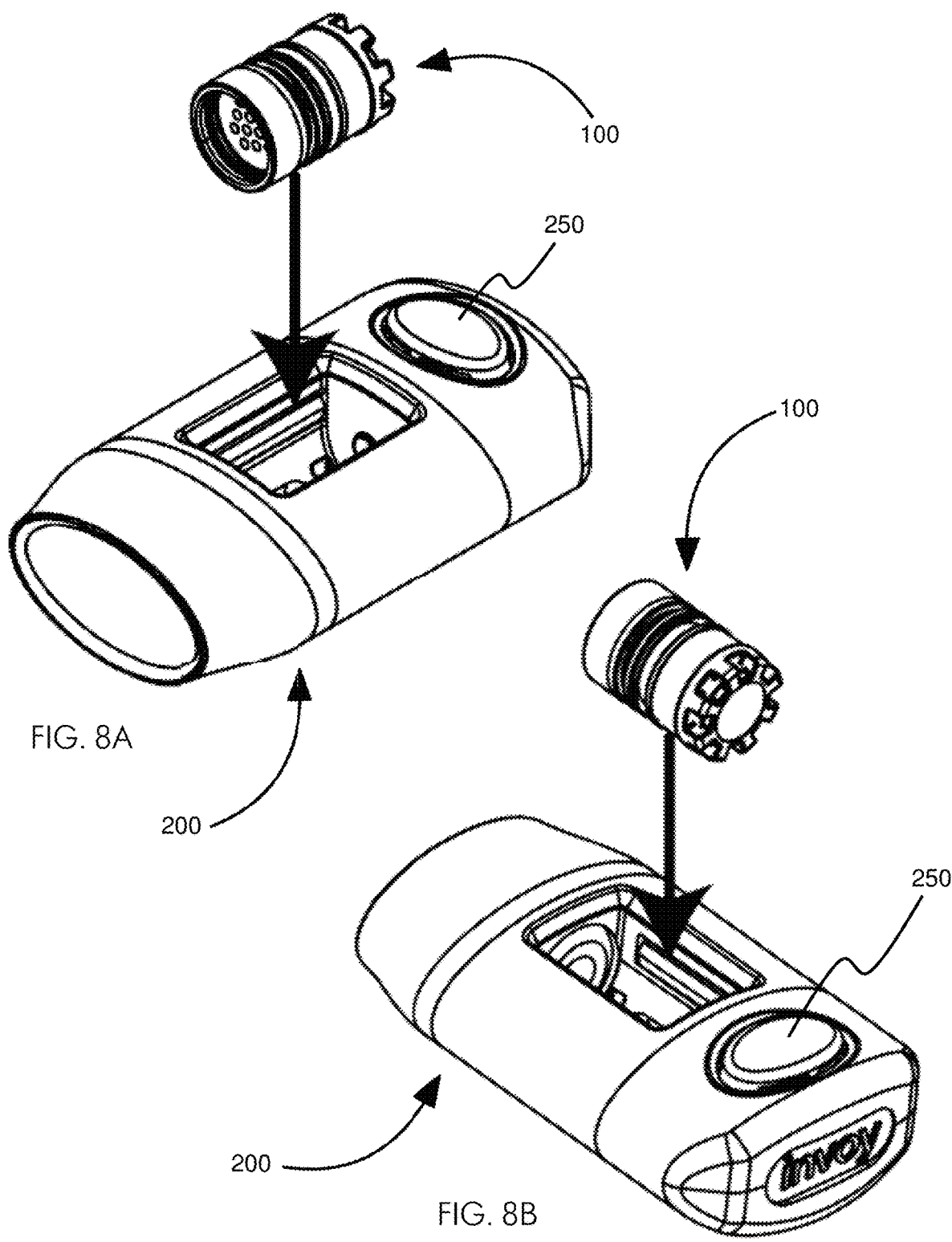

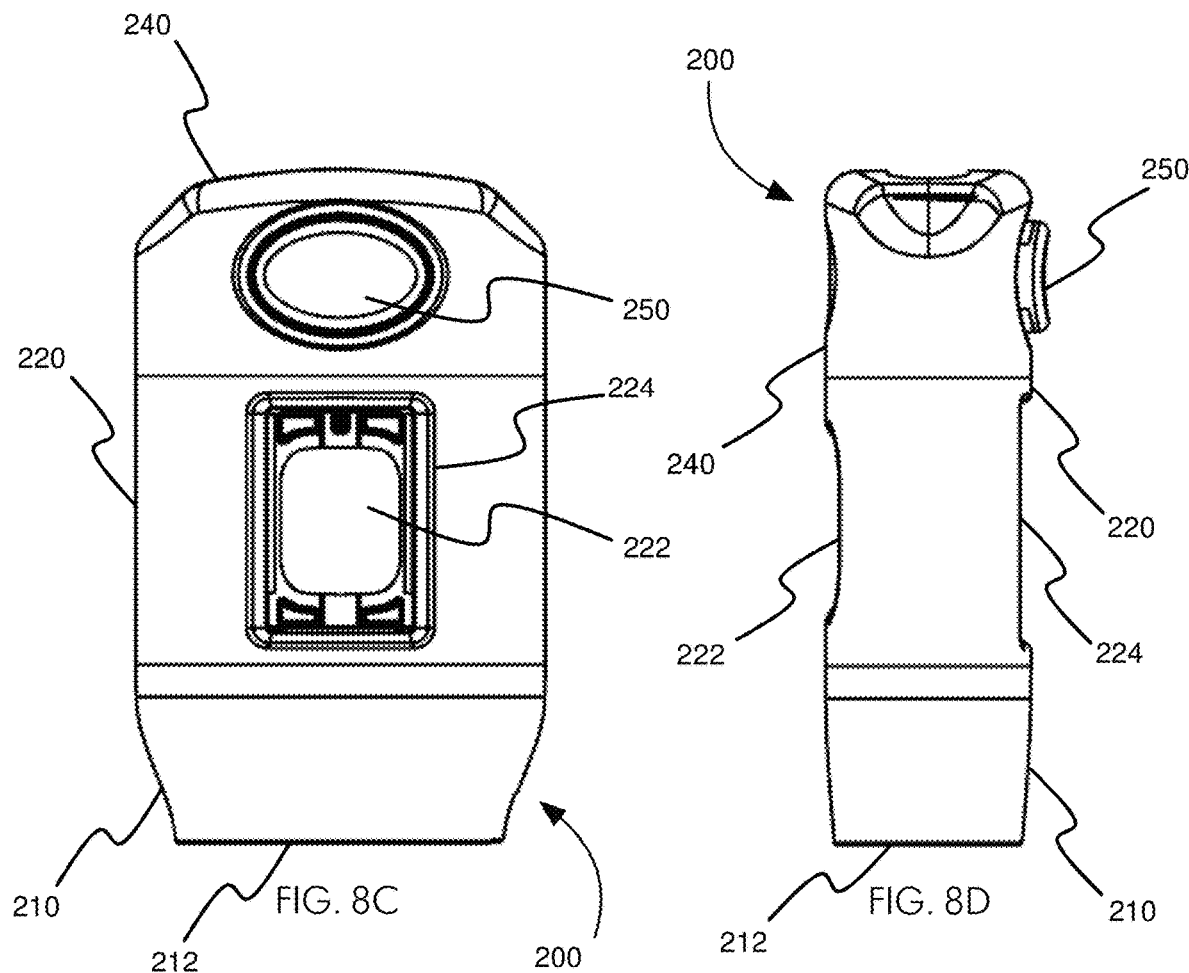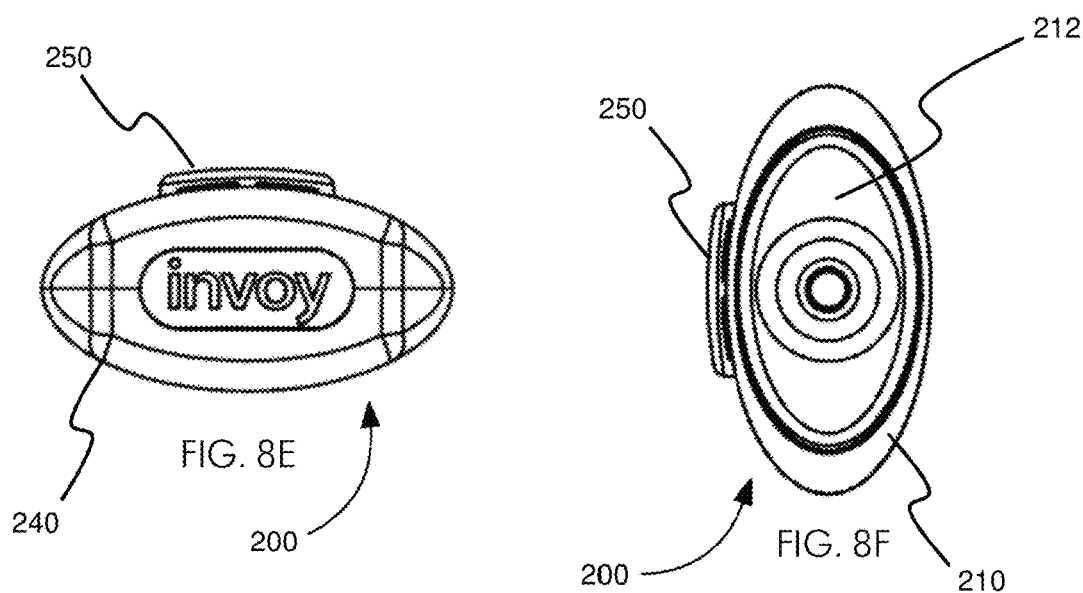

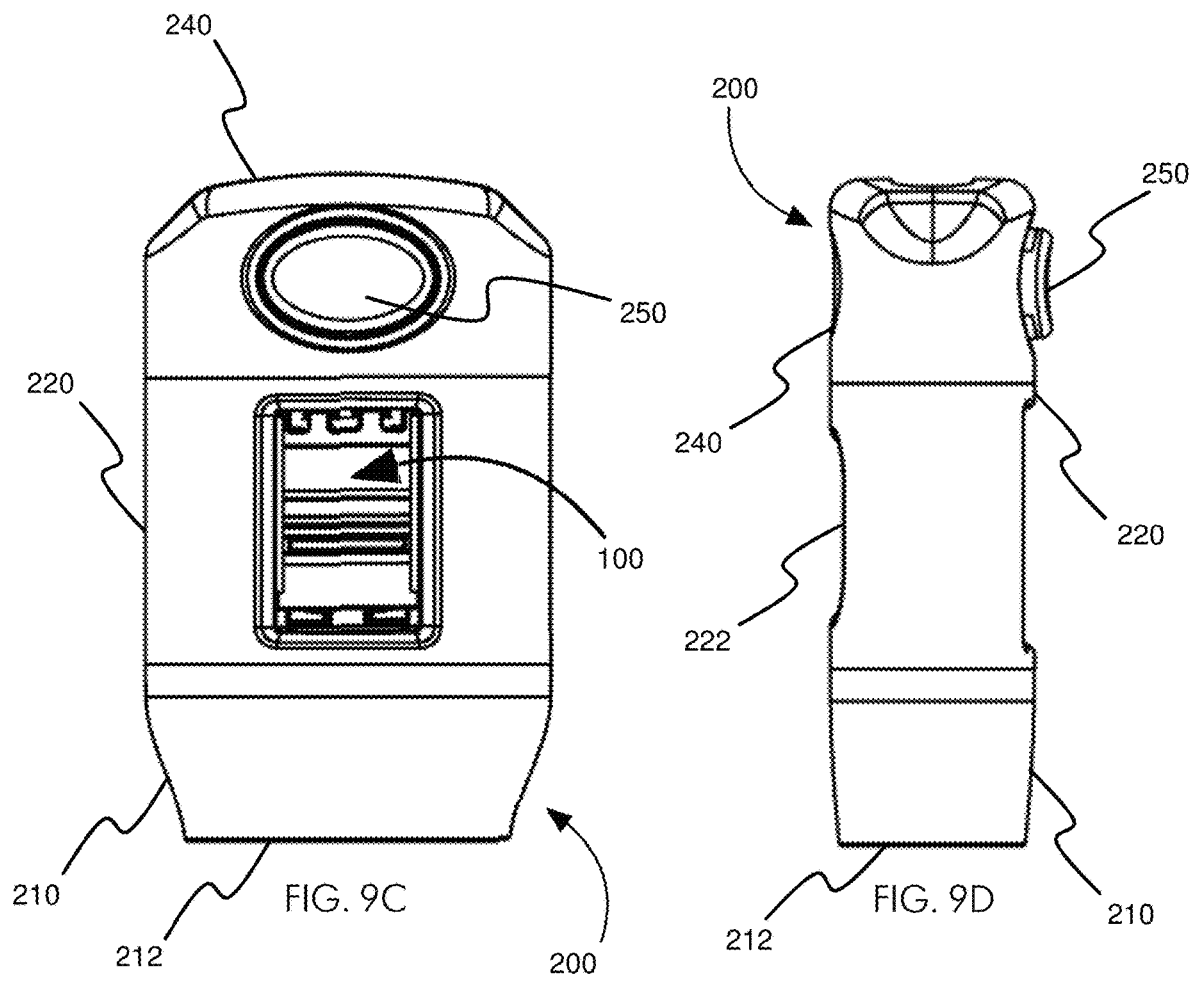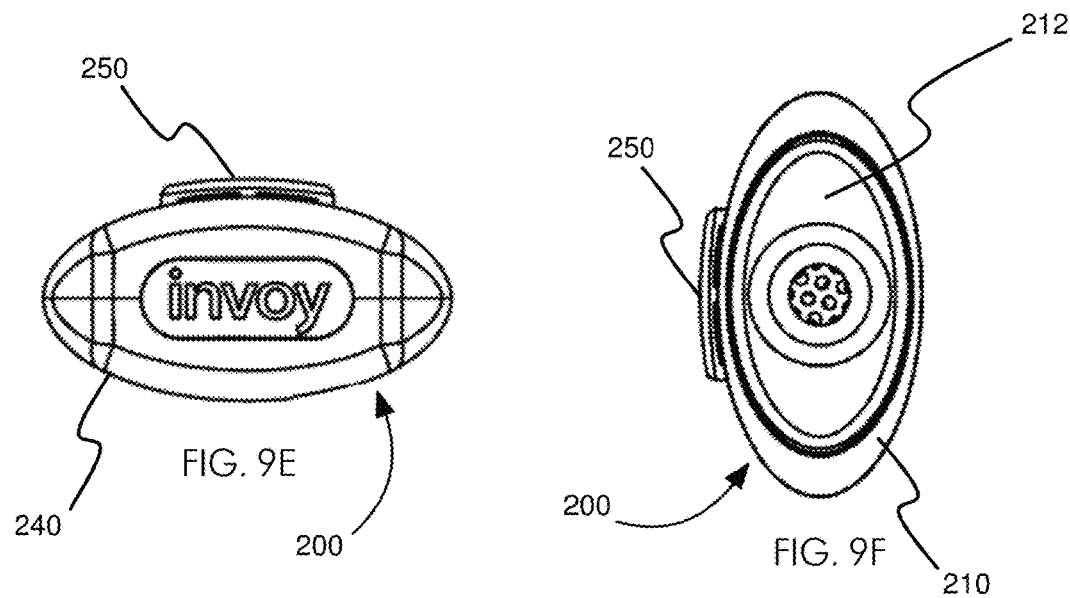

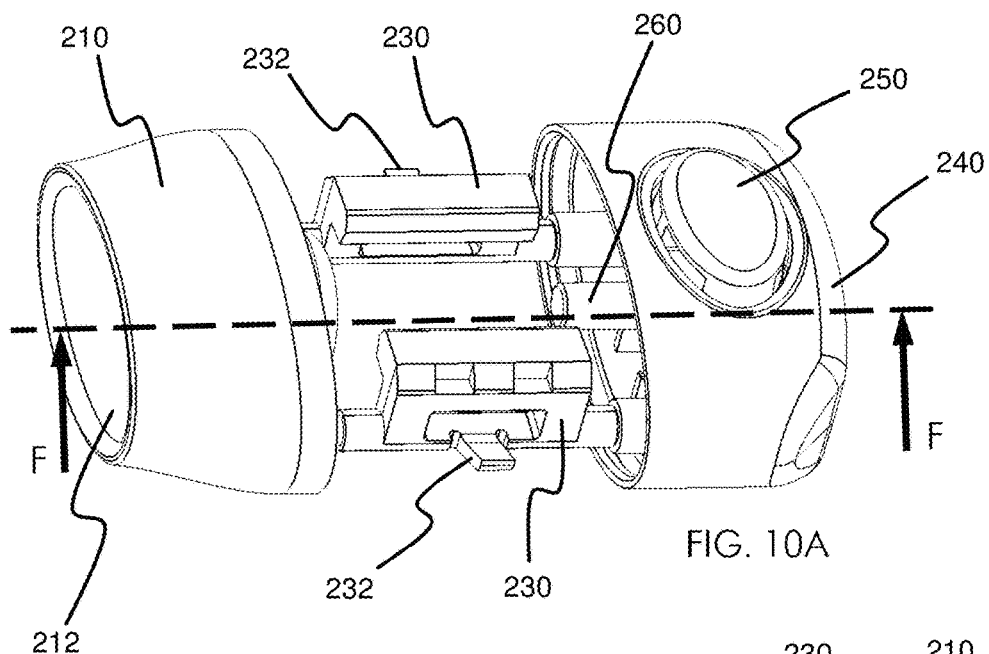
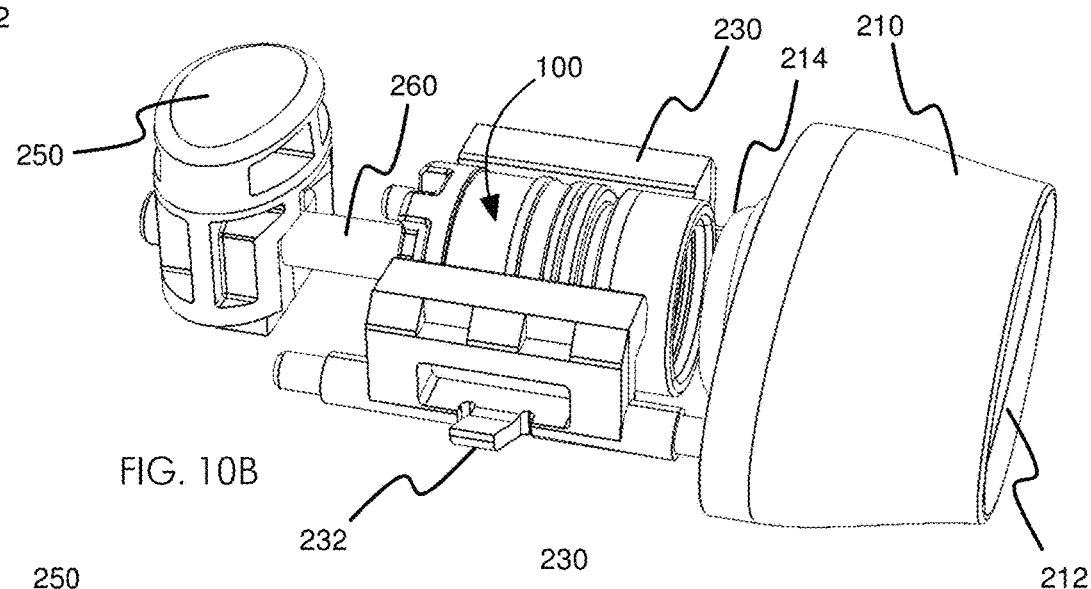
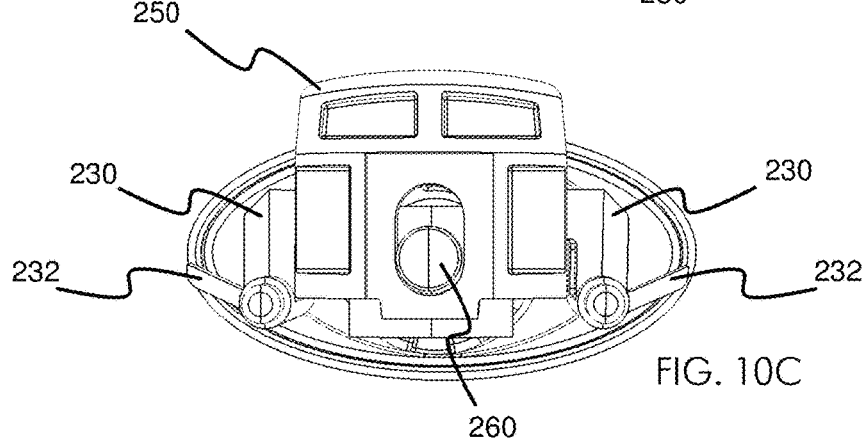

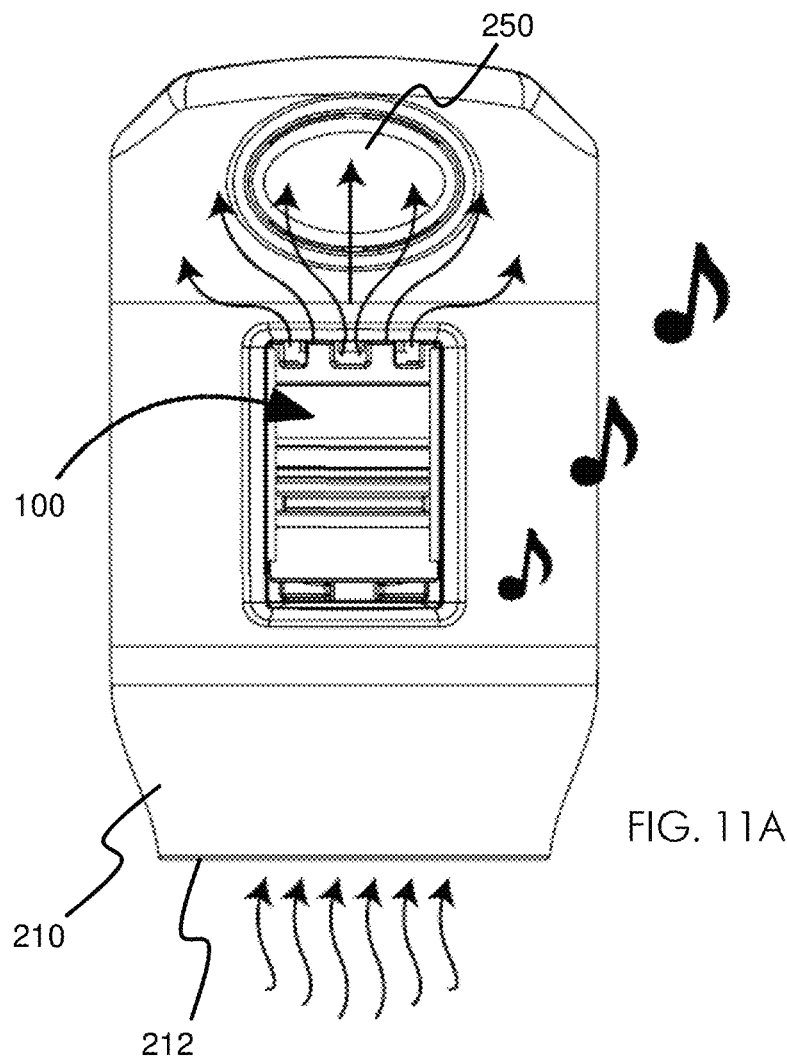
FIG. 11A
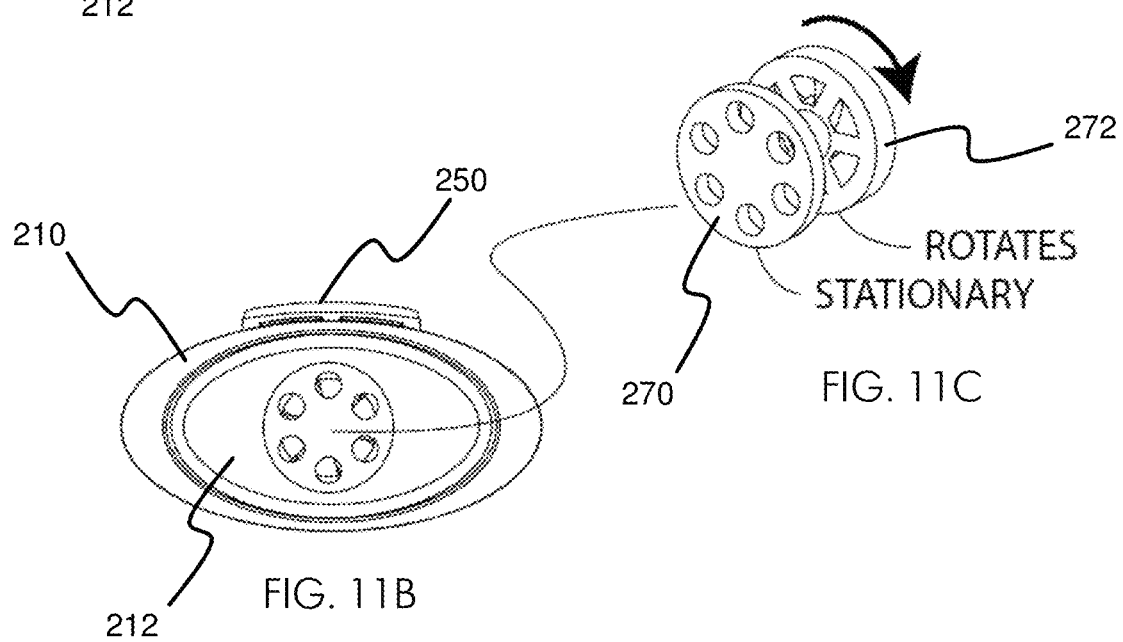
FIG. 11B
FIG. 11C

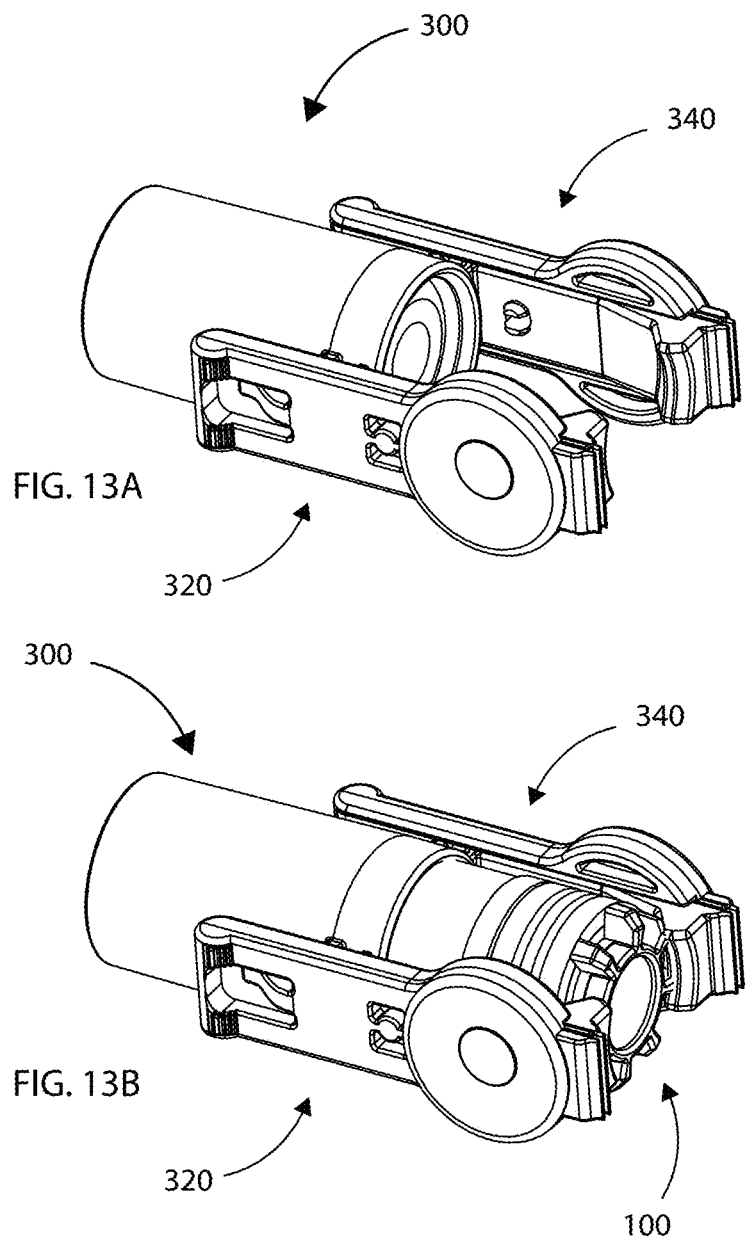

FRIT MOLDED WITH
POROUS / REACTIVE
BEAD BLEND

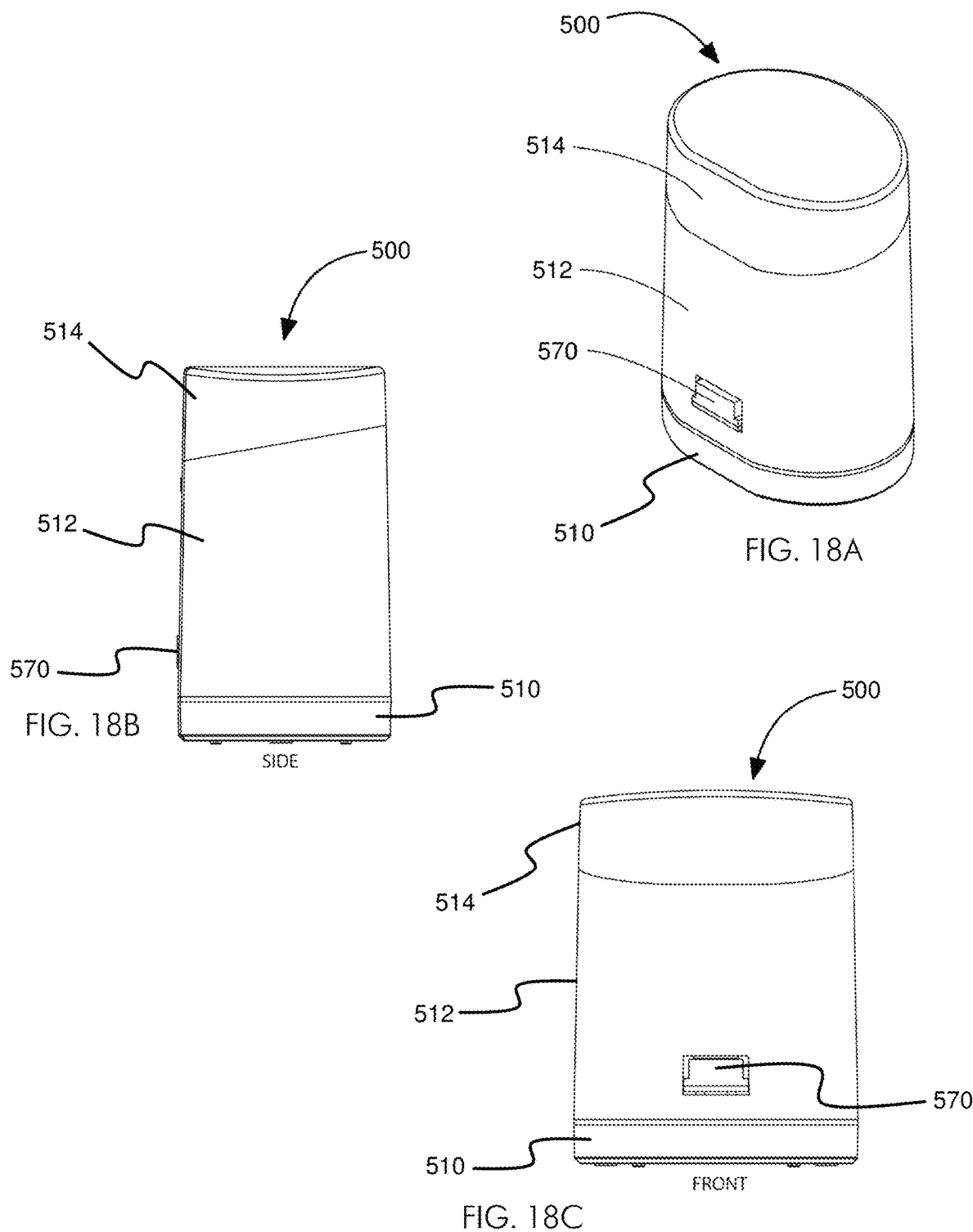

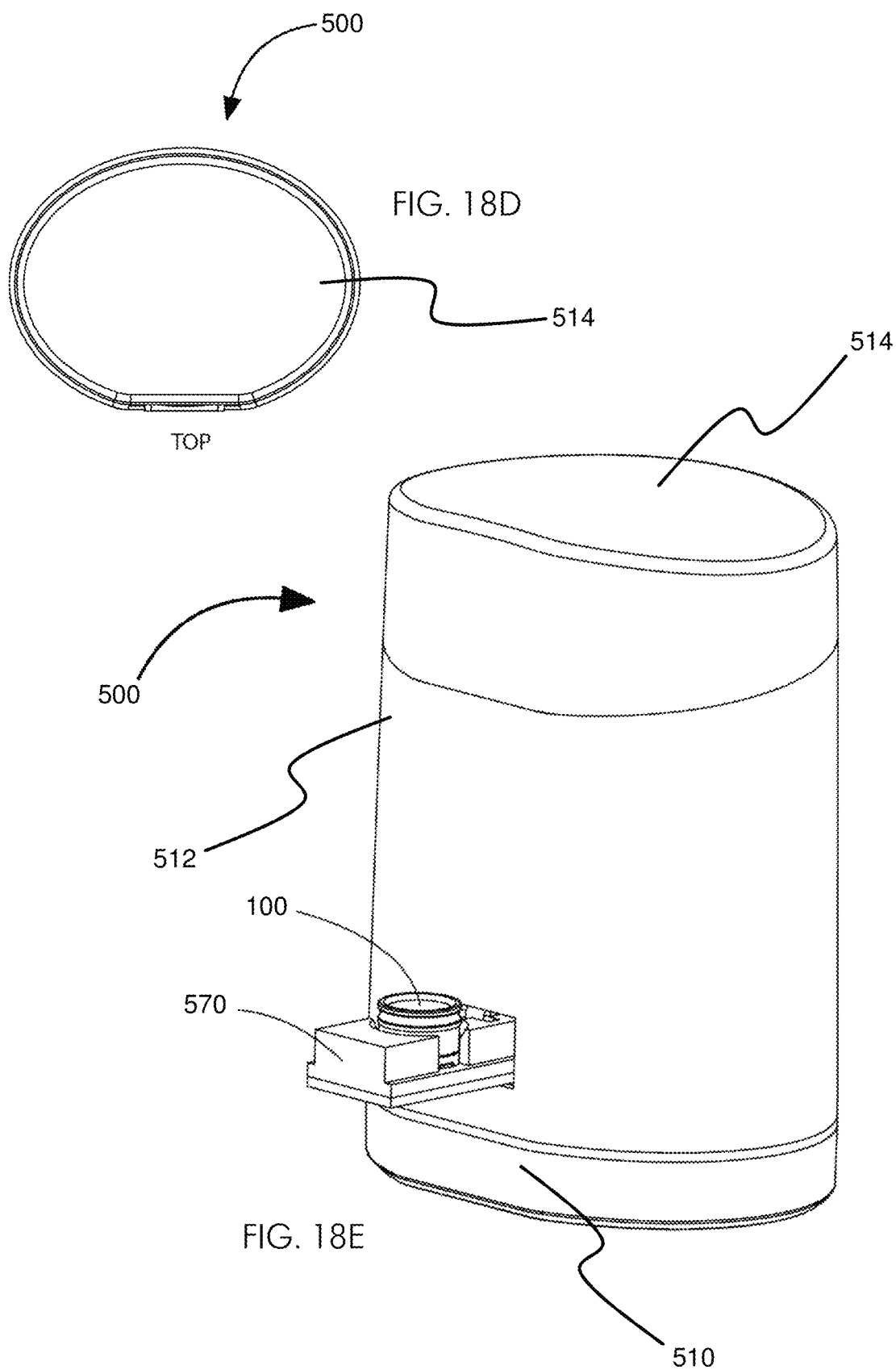

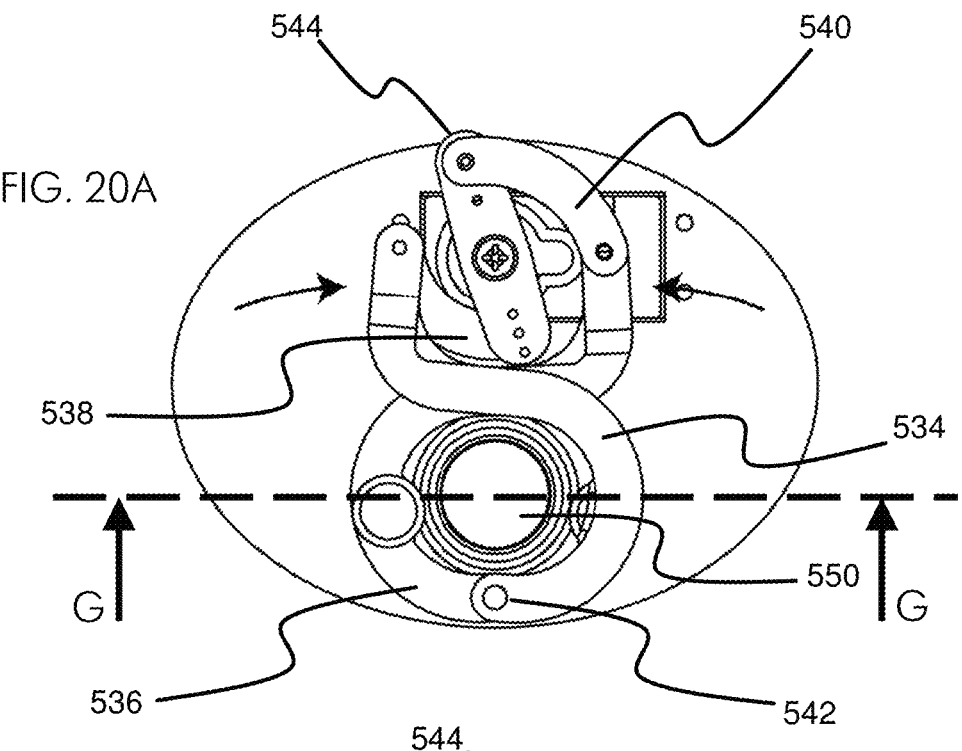
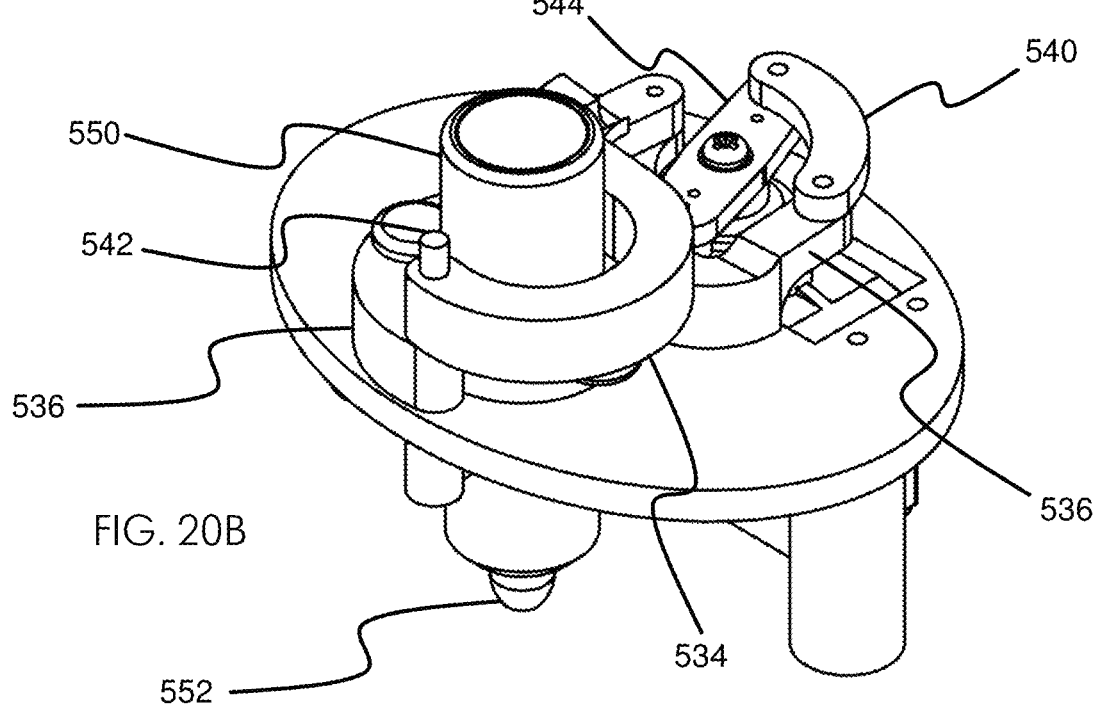

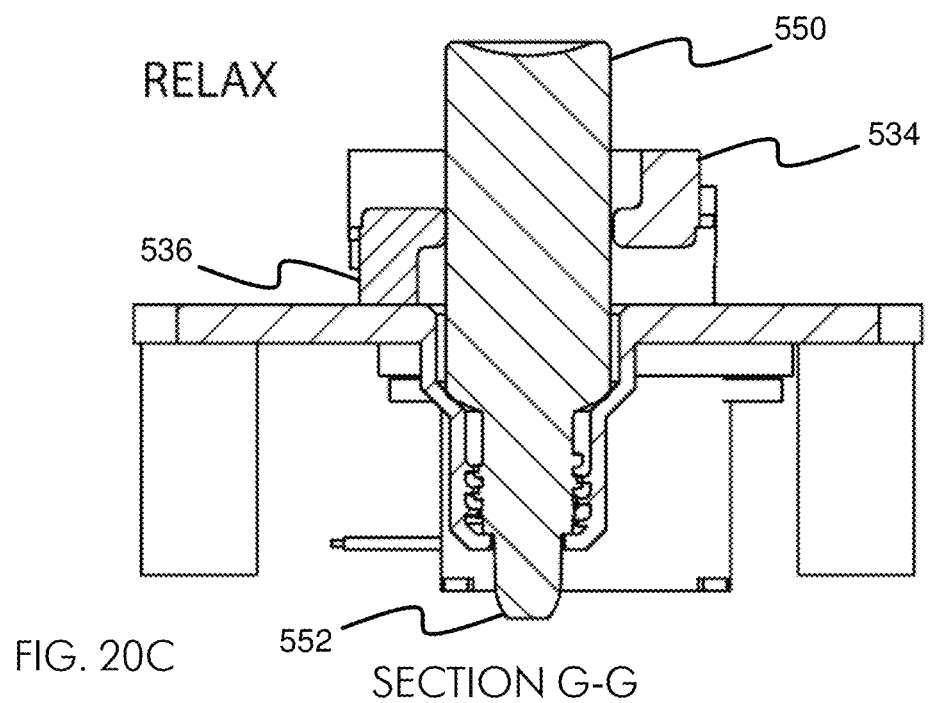
FIG. 20C SECTION G-G
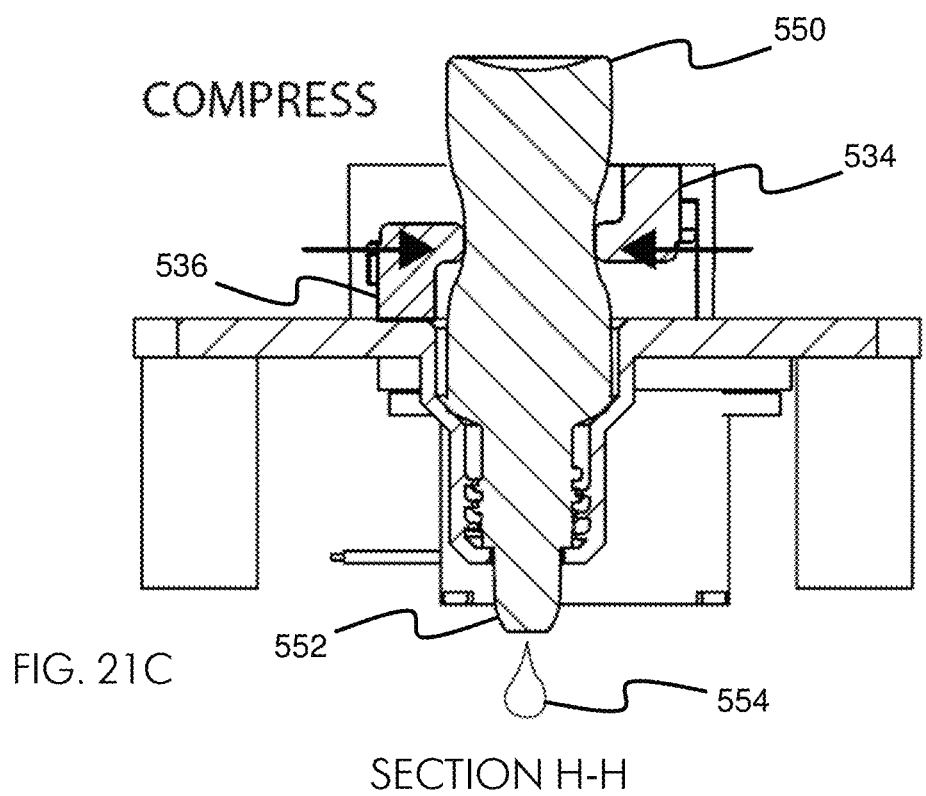
FIG. 21C SECTION H-H

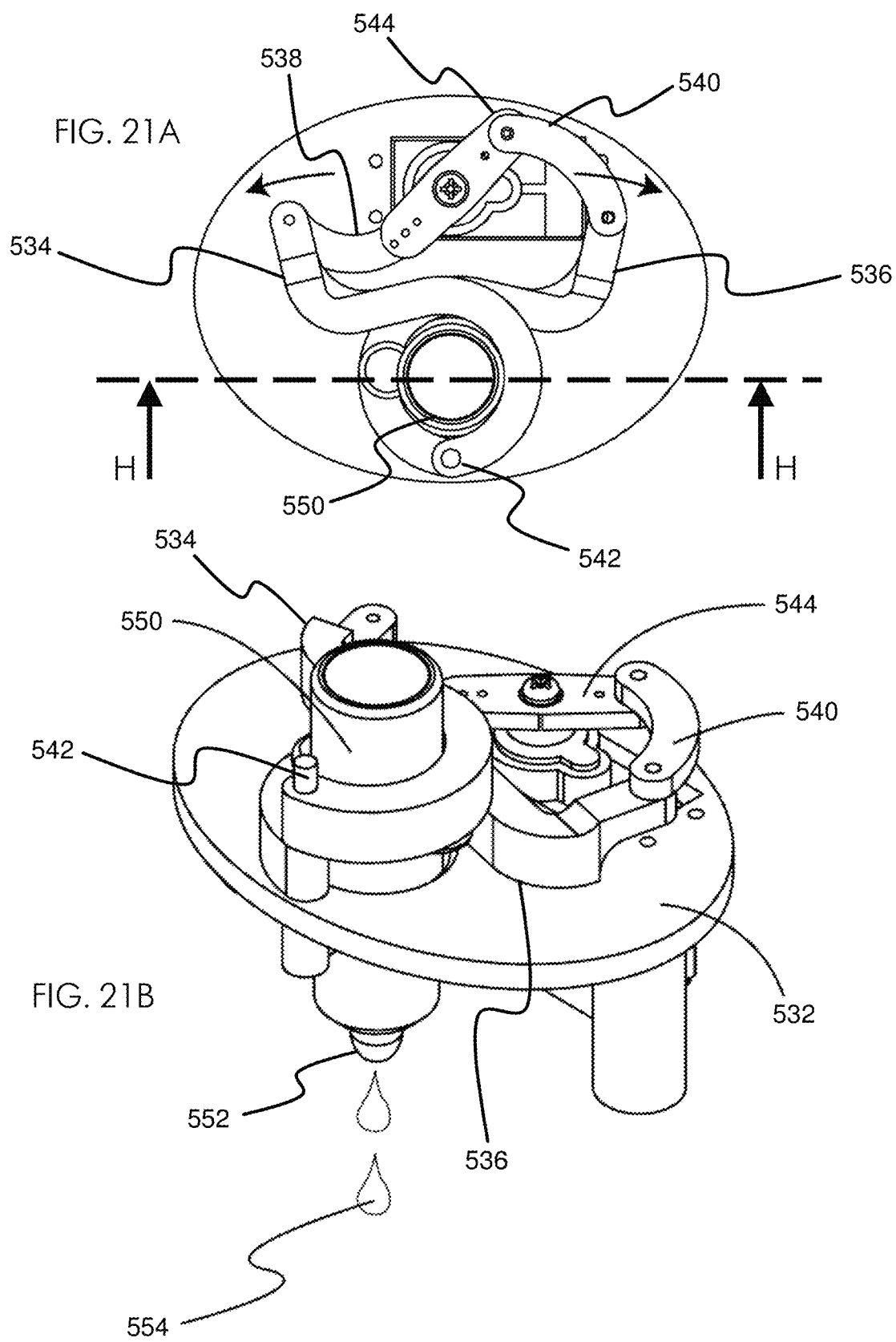

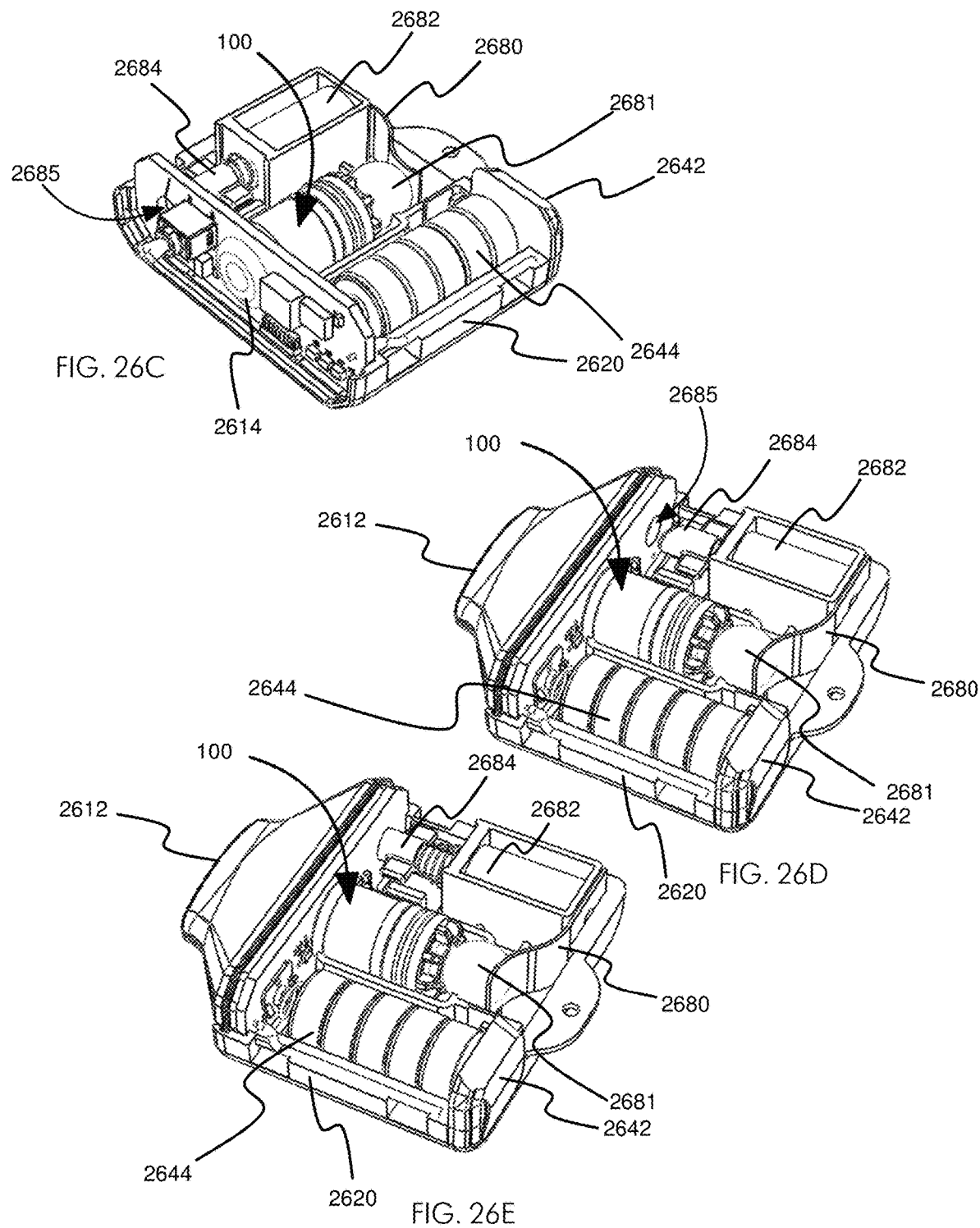

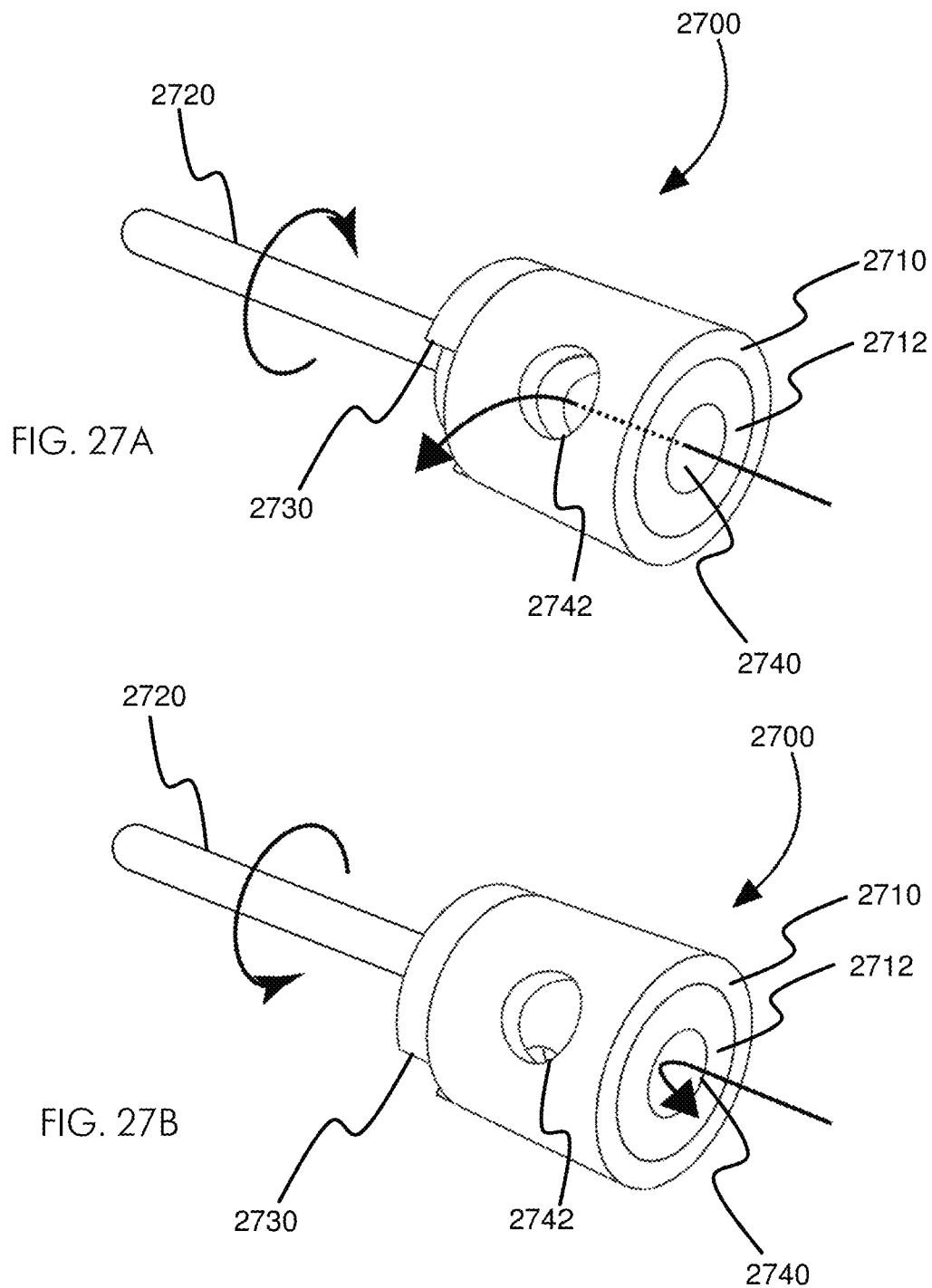

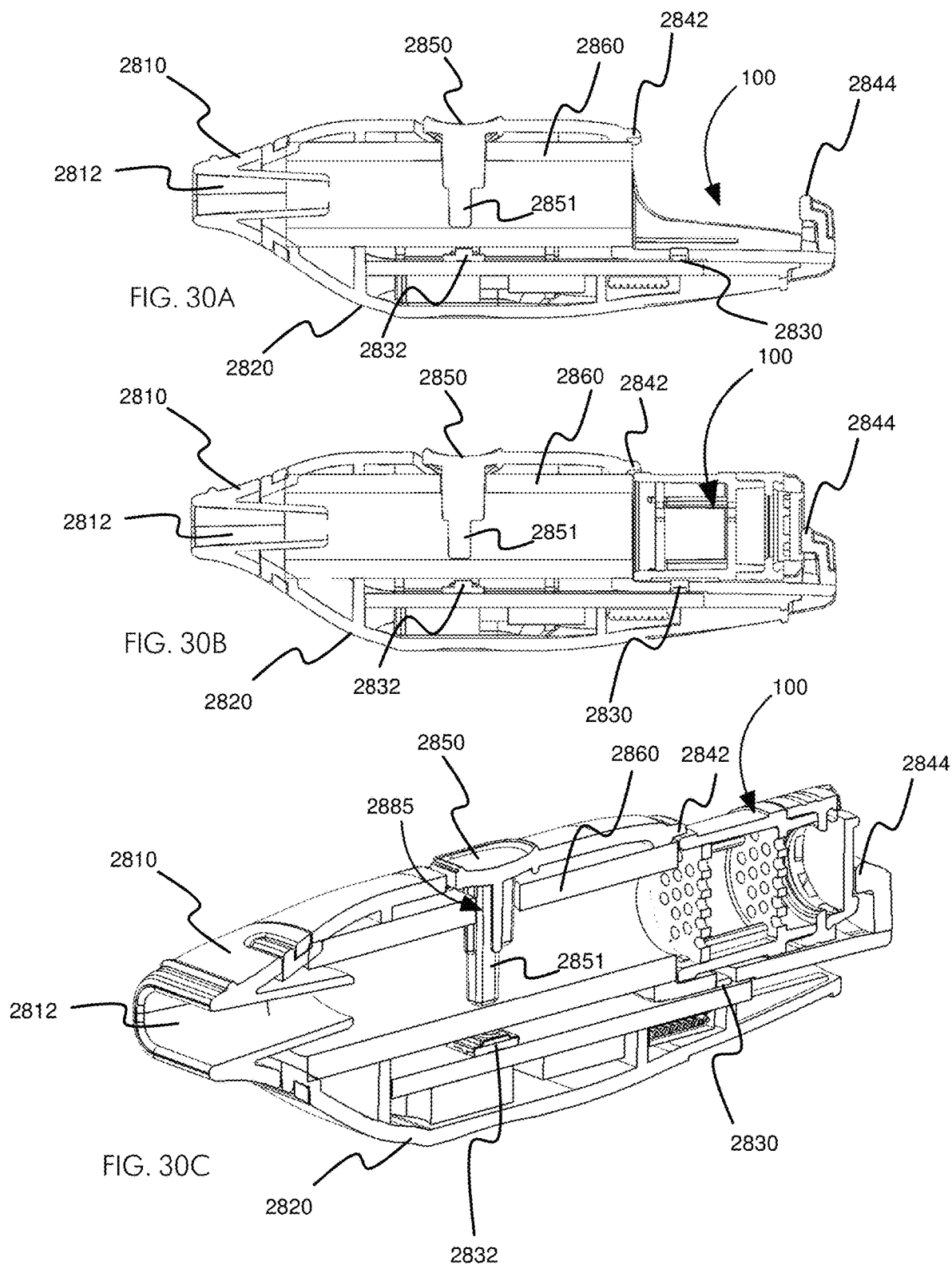

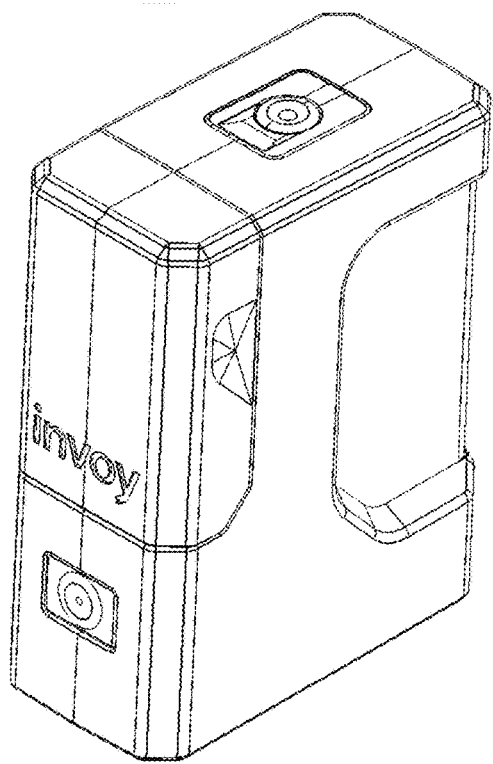
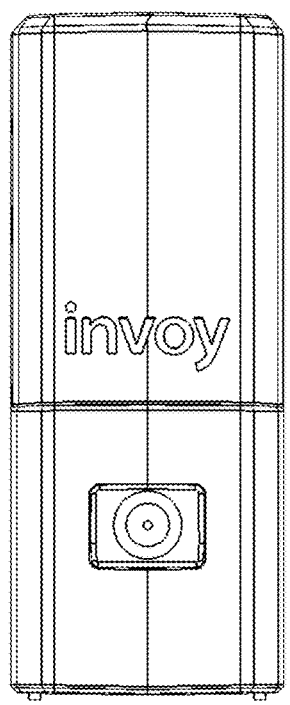
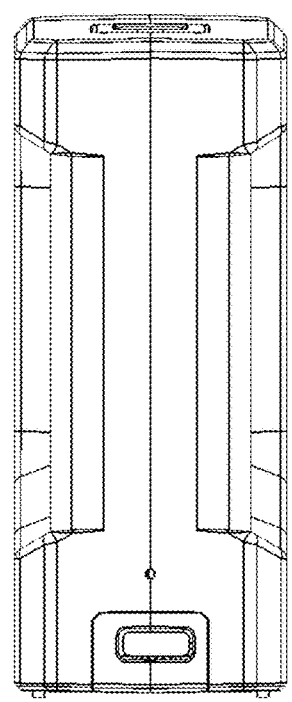
FIG. 31A
FIG. 31B
FIG. 31C
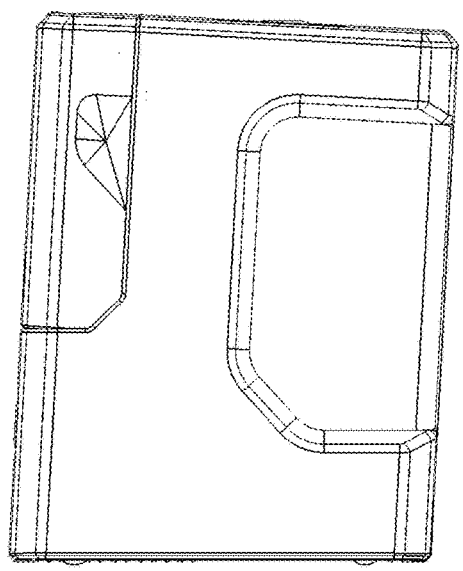
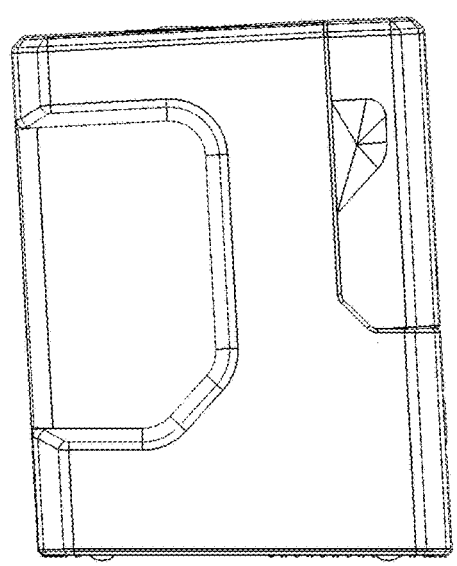
FIG. 31D
FIG. 31E

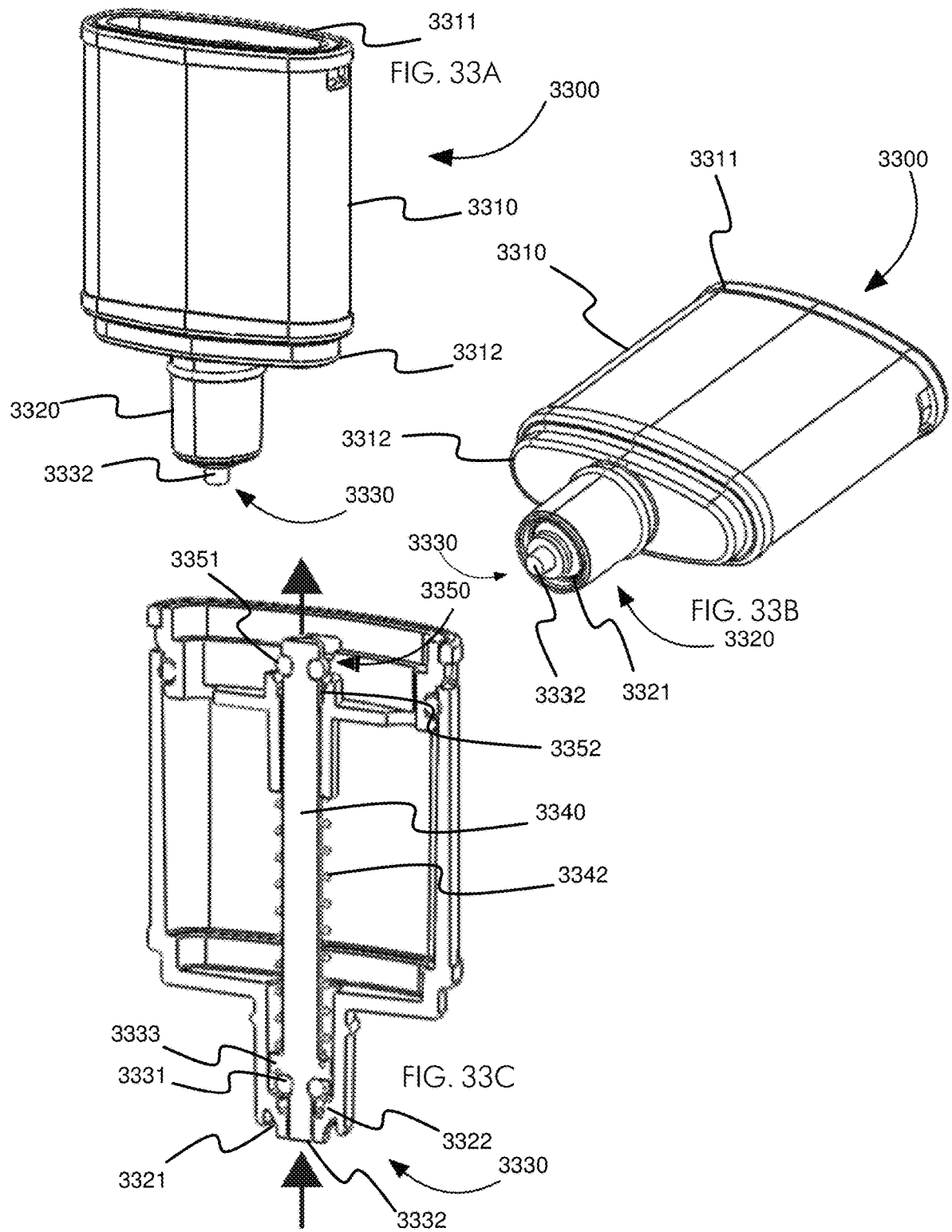

EXTRACTING AN ANALYE FROM A BREATH SAMPLE USING A SOLID POROUS STRUCTURE CONTAINING A REACTIVE MATERIAL

PRIORITY CLAIM

This application claims the benefit of U.S. Provisional Patent Appl. No. 62/675,109, filed May 22, 2018, the disclosure of which is hereby incorporated herein by reference.

BACKGROUND

Field

The present disclosure relates to apparatuses, systems, and methods for sensing or measuring chemical components or constituents (e.g., analytes) in the breath of a patient or "subject," and preferably endogenous analytes in breath, and correspondingly, to devices and methods for regulating the flow of the breath sample during the pre-measurement capture process and/or during such sensing or measurement.

Description of the Related Art

The importance or benefits of measuring the presence or concentration of chemical constituents in the body to aid in assessing a patient or subject's physiological or pathophysiological state is well known in the medical and diagnostic communities. Standard approaches to chemically-based diagnostic screening and analysis typically involve blood tests and urine tests.

Blood tests of course require that blood be drawn. Patients associate this procedure with pain, a factor that can have adverse implications for patient compliance in home-based assessments. In clinical settings, the need to draw blood typically requires trained personnel to draw the blood, carefully and properly label it, handle it and the like. It is typically necessary to transport the sample to a laboratory, often off site, for analysis. Given the logistics and economics, the lab analysis usually is carried out in bulk on large numbers of samples, thus requiring bulk handling and logistics considerations and introducing delay into the time required to obtain results. It is then typically necessary for follow-up analysis by the physician or clinician to assess the lab results and further communicate with the patient. In large part because of these logistics and delays, it is usually necessary for the patient or subject to return for a follow up visit, thus taking additional clinical time and causing additional expense.

Urine tests involve similar drawbacks. Such tests can be messy, unsanitary, and introduce issues with respect to labeling, handling and contamination avoidance. They also usually involve lab analysis, with associated delays and expense. As with blood, urine tests, it is typically necessary to transport the samples to an off-site laboratory for analysis. Given the logistics, the lab analysis usually is carried out in bulk on large numbers of samples, thus again involving delay and expense.

There are many instances in which it is desirable to sense the presence and/or quantity or concentration of an analyte in a gas. "Analyte" as the term is used herein is used broadly to mean the chemical component or constituent that is sought to be sensed using devices and methods according to various aspects of the invention. An analyte may be or comprise an element, compound or other molecule, an ion or molecular fragment, or other substance that may be contained within a fluid. In some instances, embodiments and methods, there may be more than one analyte present, and an objective is to sense multiple analytes. "Gas" as the term is used herein also is used broadly and according to its common meaning to include not only pure gas phases but also vapors, non-liquid fluid phases, gaseous colloidal suspensions, solid phase particulate matter or liquid phase droplets entrained or suspended in gases or vapors, and the like. "Sense" and "sensing" as the terms are used herein are used broadly to mean detecting the presence of one or more analytes, or to measure the amount or concentration of the one or more analytes.

The use of breath as a source of chemical analysis can overcome many of these drawbacks. The presence of these analytes in breath and their associated correlations with physiological or pathophysiological states offer the substantial theoretical or potential benefit of providing information about the underlying or correlated physiological or pathophysiological state of the subject, in some cases enabling one to screen, diagnose and/or treat a patient or subject easily and cost effectively. Breath analysis can avoid painful invasive techniques such as with blood tests, and messy and cumbersome techniques such as urine analysis. Moreover, in many applications test results can be obtained promptly, e.g., during a single typical patient exam or office visit, and cost effectively.

As is well known in the field of pulmonology, breath, and particularly breath exhalations, comprise a range of chemical components, or analytes. An "analyte" is a chemical component or constituent that is a candidate for sensing, detection or measurement. Breath composition varies somewhat from subject to subject, and within a given subject, from time to time, depending on such factors as physical condition (e.g., weight, body composition), diet (e.g., general diet, recent intake of food, liquids, etc.), exertion level (e.g., resting metabolic rate versus under stress or exercise), and pathology (e.g., diseased state). Approximately 200 to 300 analytes can be found in human breath.

Certain breath analytes have been correlated with specific physiological or pathophysiological states. Such correlations are particularly useful for "endogenous" analytes (i.e., those that are produced by the body), as opposed to "exogenous" analytes (i.e., those that are present in breath strictly as a result of inhalation, ingestion or consumption and subsequent exhalation by the subject). Examples are set forth in Table 1.

TABLE 1

| Candidate Analyte | Illustrative Pathophysiology/Physical State |
| --- | --- |
| Acetone | Lipid metabolism (e.g., epilepsy management, nutritional monitoring, weight loss therapy, early warning of diabetic ketoacidosis), environmental monitoring, acetone toxicity, congestive heart failure, malnutrition, exercise, management of eating disorders |
| Ethanol Acetaldehyde | Alcohol toxicity, bacterial growth |
| Ammonia | Liver or renal failure, protein metabolism, dialysis monitoring, early detection of chronic kidney disease, acute kidney disease detection and management |
| Oxygen and Carbon Dioxide | Resting metabolic rate, respiratory quotient, oxygen uptake |
| Isoprene | Lung injury, cholesterol synthesis, smoking damage |

TABLE 1-continued

| Candidate Analyte | Illustrative Pathophysiology/Physical State |
|---|---|
| Pentane | Lipid peroxidation (breast cancer, transplant rejection), oxidative tissue damage, asthma, smoking damage, chronic obstructive pulmonary disease ("COPD") |
| Ethane | Smoking damage, lipid peroxidation, asthma, COPD |
| Alkanes | Lung disease, cancer metabolic markers |
| Benzene | Cancer metabolic monitors |
| Carbon-13 | *H. pylori* infection |
| Methanol | Ingestion, bacterial flora |
| Leukotrienes | Present in breath condensate, cancer markers |
| Hydrogen peroxide | Present in breath condensate |
| Isoprostane | Present in breath condensate, cancer markers |
| Peroxynitrite | Present in breath condensate |
| Cytokines | Present in breath condensate |
| Glycans | Glucose measurement, metabolic anomalies (e.g., collected from cellular debris) |
| Carbon monoxide | Inflammation in airway (asthma, bronchiectasis), lung disease |
| Chloroform | |
| Dichlorobenzene | Compromised pulmonary function |
| Trimethyl amine | Uremia |
| Dimethyl amine | Uremia |
| Diethyl amine | Intestinal bacteria |
| Methanethiol | Intestinal bacteria |
| Methylethylketone | Lipid metabolism |
| O-toluidine | Cancer marker |
| Pentane sulfides | Lipid peroxidation |
| Hydrogen sulfide | Dental disease, ovulation |
| Sulfated hydrocarbon | Cirrhosis |
| Cannabis | Drug concentration |
| G-HBA | Drug testing |
| Nitric oxide | Inflammation, lung disease |
| Propane | Protein oxidation, lung disease |
| Butane | Protein oxidation, lung disease |
| Other Ketones (other than acetone) | Lipid metabolism |
| Ethyl mercaptane | Cirrhosis |
| Dimethyl sulfide | Cirrhosis |
| Candidate Analyte | Illustrative Pathophysiology/Physical State |
| Dimethyl disulfide | Cirrhosis |
| Carbon disulfide | Schizophrenia |
| 3-heptanone | Propionic acidaemia |
| 7-methyl tridecane | Lung cancer |
| Nonane | Breast cancer |
| 5-methyl tridecane | Breast cancer |
| 3-methyl undecane | Breast cancer |
| 6-methyl pentadecane | Breast cancer |
| 3-methyl propanone | Breast cancer |
| 3-methyl nonadecane | Breast cancer |
| 4-methyl dodecane | Breast cancer |
| 2-methyl octane | Breast cancer |
| Trichloroethane | |
| 2-butanone | |
| Ethyl benzene | |
| Xylene (M, P, O) | |
| Styrene | |
| Tetrachloroethene | |
| Toluene | |
| Ethylene | |
| Hydrogen | |

The inherent relative advantage of breath analysis over other techniques, together with the relatively wide array of analytes and analyte correlations, illustrate that the potential benefits breath analysis offers are substantial.

Notwithstanding these potential benefits, however, with the exception of breath ethanol devices used for law enforcement, there has been a paucity of breath analyzers on the commercial market, particularly in medically-related applications. This lack of commercialization is attributable in large measure to the relatively substantial technical and practical challenges associated with the technology. Principal among them is the requirement for sensitivity. Analytes of interest, particularly endogenous analytes, often are present in extremely low concentrations, e.g., of only parts per million ("ppm") or parts per billion ("ppb"). In addition, the requirements for discrimination or selectivity is of critical concern. As noted herein above, breath typically includes a large number, sometimes hundreds, of chemical components in a complex matrix. Breath also usually has considerable moisture content. Chemical sensing regimes conducive for breath ammonia measurement, for example, are preferably sensitive to 50 ppb in the presence of 3 to 6% water vapor with 3 to 5% carbon dioxide. Successfully and reliably sensing a particular analyte in such a heterogeneous and chemically-reactive environment presents substantial challenges.

Most publicly-known breath analysis devices and methods involve using a single breath, and more specifically a single exhalation, as the breath sample to identify or measure a single analyte. The sample is collected and analyzed to determine whether the analyte is present, and in some cases, to measure its concentration. The breath analysis system introduced by Abbott Laboratories, e.g., in U.S. Pat. Nos. 4,970,172, 5,071,769, and 5,174,959, provides an illustrative example. There, Abbott used a single exhalation from a patient to detect the presence of acetone to obtain information about fat metabolism.

Notwithstanding the potential benefits of breath analysis, particularly portable breath analysis devices for home or field use, commercial offerings of such devices have been available only recently, and the accuracy and reliability in such settings have left much room for improvement. Practical breath analysis devices must operate accurately and reliably in the context of their use, e.g., in patient homes, clinics, etc., in varying environments, (temperatures, humidity, etc.), with various types of patients, over the life of the devices.

The use of multiple breaths is substantially lesser known and studied. Published reports generally have been limited to the determination of the production rate of carbon dioxide and the consumption rate of oxygen. This technique was developed due to the presence of these two analytes (oxygen and carbon dioxide) in the ambient atmosphere.

These approaches have been limited and relatively deficient, however, for example, in that the breath sample or samples are collected in bulk, so that the analyte of interest is mixed in with other constituents. This often dilutes the analyte and increases the difficulty of discriminating the desired analyte. These approaches also limit the flexibility of the breath analysis to undertake more specialized or complex analyses.

Additionally, such approaches are relatively deficient because the instrumentation used for single breath analysis usually is different from and sometimes inadequate for multiple breath analyte measurement.

Yet another challenge to breath analysis involves the fluid mechanical properties of the breath sample as it travels through the measurement device.

There is considerable advantage in providing breath analysis devices that can accurately and reliably sense or measure breath analytes in a clinical or patient home setting. Thus, there is a need for small or portable, cost effective devices and components.

In many instances, there is a need or it is desirable to make the analysis for an analyte in the field, or otherwise to make such assessment without a requirement for expensive and cumbersome support equipment such as would be available in a hospital, laboratory or test facility. It is often desirable to do so in some cases with a largely self-contained device, preferably portable, and often preferably easy to use. It also is necessary or desirable in some instances to have the capability to sense the analyte in the fluid stream in real time or near real time. In addition, and as a general matter, it is highly desirable to accomplish such sensing accurately and reliably.

The background matrix of breath presents numerous challenges to sensing systems, which necessitate complex processing steps and which further preclude system integration into a form factor suitable for portable usage by layman end-users. For example, breath contains high levels of humidity and moisture, which may interfere with the sensor or cause condensation within the portable device, amongst other concerns. Also, the flow rate or pressure of breath as it is collected from a user typically varies quite considerably. Flow rate variations are known to impact, often significantly, the response of chemical sensors. Breath, especially when directly collected from a user, is typically at or near core body temperature, which may be considerably different than the ambient temperature. Additionally, body temperature may vary from user to user or from day to day, even for a single user. Devising a breath analyzer thus is a non-trivial task, made all the more difficult to extent one tries to design and portable and field-amenable device.

Notably, the measurement of endogenous analytes in breath presents different challenges and requires different techniques and devices than the measurement of exogenous analytes. Endogenous analytes are those that are produced by the body, excluding the lumen of the gastrointestinal tract, whereas exogenous analytes are those that are present in breath as a result of the outside influence or as a result of user consumption. However, many analytes are produced endogenously and can also be exogenously introduced. For example, ammonia is produced endogenously through the metabolism of amino acids, but can also be introduced exogenously from the environment such as ammonia-containing household cleaning supplies. The term "endogenous" is used according to its common meaning within the field. Endogenous analytes are produced by natural or unnatural means within the human body, its tissues or organs, typically excluding the lumen of the gastrointestinal tract.

There are a number of significant challenges to measuring endogenous analytes in breath. Endogenous analytes typically have significantly lower concentrations in the breath, often on the order of parts per million ("ppm"), parts per billion ("ppb"), or less. Additionally, measurement of endogenous analytes requires discrimination of the analyte in a complex matrix of background gases. Instead of typical atmospheric gas composition (e.g., primarily nitrogen), exhaled breath has high humidity content and larger carbon dioxide concentration. This leads to unique challenges in chemical sensitivity, selectivity and stability. For example, chemistries conducive for breath ammonia measurement are preferably sensitive to 50 ppb in the presence of 3 to 6% water vapor with 3 to 5% carbon dioxide.

Because of the historical difficulty in even detecting endogenous breath analytes, other challenges have not been extensively investigated. Examples of such challenges include: (a) correlating the analytes to health or disease states, (b) measuring these analytes given characteristics of human exhalation, e.g., flow rate and expiratory pressure, (c) measuring these analytes sensitively and selectively, and (d) doing all these in a portable, cost effective package that can be implemented in medical or home settings.

Colorimetric devices are one method for measuring a reaction involving a breath analyte. Colorimetric approaches to endogenous breath analysis have historically been plagued with lengthy response times, and expensive components. Often such analysis has to be performed in a laboratory. Thus there remains a need for a breath analyzer that can measure endogenous breath components present in relatively low concentrations, such as acetone, accurately and quickly, without a long wait period for results, in addition to being inexpensive and useable by the layperson. It is also preferable if the breath analyzer is capable of measuring multiple analytes.

The above-noted problems are not necessarily addressed by all of the disclosed embodiments. For example, some problems may be addressed by some embodiments, while other problems are addressed by other embodiments. Thus, the foregoing description should not be relied upon to limit the scope of protection.

BRIEF DESCRIPTION OF THE DRAWINGS

FIGS. 1A-1D show various views of an embodiment of a sample capture cartridge. FIG. 1A shows a side view of an embodiment of a sample capture cartridge. FIG. 1B shows a top view of the sample capture cartridge of FIG. 1A. FIG. 1C shows a cut-away view of a side view of the sample capture cartridge of FIG. 1A. FIG. 1D shows a bottom view of an embodiment of the sample capture cartridge of FIG. 1A.

FIG. 3 shows a bottom-biased three-quarter view of an embodiment of a sample capture cartridge and an air flow path there through.

FIGS. 4A-4J show various view of an embodiment of a cartridge lens cap.

FIG. 4A shows a top-biased three-quarter view of an embodiment of a cartridge lens cap.

FIG. 4B shows a bottom-biased three-quarter view of an embodiment of a cartridge lens cap.

FIG. 4C shows a bottom-biased three-quarter view of another embodiment of a cartridge lens cap. FIG. 4D shows a top view of the cartridge lens cap of FIG. 4A. FIG. 4E shows a side view of the cartridge lens cap of FIG. 4A. FIG. 4F shows a cut-away view of the cartridge lens cap of FIG. 4E. FIG. 4G shows a bottom view of the cartridge lens cap of FIG. 4A. FIG. 4H shows a cartridge lens cap having an upper portion and a lower portion, the upper and lower portions being decoupled from each other. FIG. 4I shows the cartridge lens cap of FIG. 4H having the upper and lower portions being coupled together. FIG. 4J shows the cartridge lens cap of FIGS. 4H-4I with a porous bowl held between the two portions.

FIGS. 5A-5F show various views of an embodiment of a bowl. FIG. 5A shows a side view of an embodiment of a porous bowl. FIG. 5B shows a cut away view of a side view of the porous bowl of FIG. 5A. FIG. 5C shows a top-biased cut-away view of the porous bowl of FIG. 5A. FIG. 5D shows a top-biased cut-away view of another embodiment of a porous bowl. FIG. 5E shows a top view of the porous bowl of FIG. 5A. FIG. 5F shows a bottom view of the porous bowl of FIG. 5A.

FIGS. 6A-6C show various views of an embodiment of a cartridge desiccant canister. FIG. 6A shows a top view of an embodiment of a cartridge desiccant canister. FIG. 6B shows a bottom view of the cartridge desiccant canister of FIG. 6A. FIG. 6C shows a cut-away view of a side view of the cartridge desiccant canister of FIG. 6A.

FIG. 7A-7C show various views of an embodiment of a desiccant retainer. FIG. 7A shows a top view of an embodiment of a desiccant retainer. FIG. 7B shows a bottom view of the desiccant retainer of FIG. 7A. FIG. 7C shows a cut-away view of a side view of the desiccant retainer of FIG. 7A.

FIGS. 8A-8F show various views of an embodiment a sample collection whistle. FIGS. 8A-8B show various views of a sample capture cartridge being loaded into an embodiment of a sample collection whistle. FIG. 8C shows a top view of an embodiment of a sample collection whistle. FIG. 8D shows a side view of the sample collection whistle of FIG. 8C. FIG. 8E shows a rear view of the sample collection whistle of FIG. 8C. FIG. 8F shows a front view of the sample collection whistle of FIG. 8C.

FIGS. 9A-9F show various views of an embodiment of a sample capture cartridge loaded into a sample collection whistle. FIGS. 9A-9B show various views of an embodiment of a sample capture cartridge after being loaded into an embodiment of a sample collection whistle. FIG. 9C shows a top view of an embodiment of a sample capture cartridge loaded into an embodiment of a sample collection whistle. FIG. 9D shows a side view of the sample capture cartridge loaded into the sample collection whistle of FIG. 9C. FIG. 9E shows a rear view of the sample capture cartridge loaded into the sample collection whistle of FIG. 9C. FIG. 9F shows a front view of the sample capture cartridge loaded into the sample collection whistle of FIG. 9C.

FIGS. 10A-10D show various views of the internal components of the sample collection whistle of FIG. 8C. FIGS. 10A & 10B show a top-biased three-quarter view of the internal components of the sample collection whistle of FIG. 8C. FIG. 10C shows a rear view of the internal components of the sample collection whistle of FIG. 8C. FIG. 10D shows a side cut-away view of the sample collection whistle of FIG. 8C.

FIGS. 11A-11C show various views of an embodiment of a sample collection whistle configured to make sound during use. FIG. 11A shows a top view of an embodiment of a sample collection whistle configured to make sound during use. FIG. 11B shows a front view of an embodiment of a sample collection whistle configured to make sound during use. FIG. 11C shows various internal noise making components of the sample collection whistle configured to make sound during use of FIG. 11B.

FIGS. 13A-13B show various views in a folded usable configuration of the one piece breather of FIGS. 12A-12B, which may be used to collect samples. FIG. 13A shows the one piece breather of FIGS. 12A-12B, folded and ready for use. FIG. 13B shows the one piece breather of FIGS. 12A-12B, folded and ready for use and into which an embodiment of a sample capture cartridge has been loaded.

FIG. 14A shows the one piece breather of FIG. 13B having breather wings in a relaxed position. FIG. 14B shows the one piece breather of FIG. 13B having breather wings in a sample collection position. FIG. 14C shows the one piece breather of FIG. 13B having breather wings in a cartridge ejection position.

FIGS. 18A-18E show various views of an embodiment of a base unit. FIG. 18A shows a top-biased front three-quarters view of an embodiment of a base unit. FIG. 18B shows a side view of an embodiment of a base unit. FIG. 18C shows a front view of an embodiment of a base unit. FIG. 18D shows a top view of an embodiment of a base unit. FIG. 18E shows a top-biased front three-quarters view of an embodiment of a base unit having a cartridge tray in an extended position.

FIG. 19A shows a top-biased three-quarters view of the internal components of an embodiment of a base unit. FIG. 19B shows a front view of the internal components of an embodiment of a base unit. FIG. 19C shows a side view of the internal components of a base unit.

FIGS. 20A-20C show various views of an embodiment of a dispensing mechanism. FIG. 20A shows a top view of an embodiment of a dispensing mechanism in a relaxed configuration. FIG. 20B shows a top-biased three-quarters view of an embodiment of a dispensing mechanism in a relaxed configuration. FIG. 20C shows a front cut-away view of an embodiment of a dispending mechanism in a relaxed configuration.

FIGS. 21A-21C show various views of an embodiment of a dispensing mechanism. FIG. 21A shows a top view of an embodiment of a dispensing mechanism in an actuated configuration. FIG. 20B shows a top-biased three-quarters view of an embodiment of a dispensing mechanism in an actuated configuration. FIG. 20C shows a front cut-away view of an embodiment of a dispending mechanism in an actuated configuration.

FIG. 22A shows a side view of an embodiment of a drip-resistant dropper tip. FIG. 22B shows a top-biased three-quarters view of a drip-resistant dropper tip. FIG. 22C shows a bottom-biased three-quarters view of a drip-resistant dropper tip.

FIG. 24A shows a front view of an embodiment of a base unit. FIG. 24B shows a front-side view of an embodiment of a base unit. FIG. 24C shows a front-side view of an embodiment of a base unit having a cartridge tray in an extended position.

FIGS. 26A-26E show various views of an embodiment of a sample capture cartridge loaded into a sample collection whistle. FIGS. 26A-26B show top three-quarters view of a sample collection whistle, with FIG. 26A being front-biased and FIG. 26B being rear-biased. FIGS. 26C-26E show various views of the internal components of the sample collection whistle of FIGS. 26A-26B. FIG. 26C shows a front-biased view of the internal components of the sample collection whistle. FIG. 26D shows the internal components of the sample collection whistle in a flow-permitting configuration. FIG. 26E shows the internal components of the sample collection whistle in a flow-blocking configuration.

FIGS. 27A-27B show an embodiment of a rotary valve that may be used in connection with various sample collection whistles disclosed herein. FIG. 27A shows the rotary valve in a flow-permitting configuration. FIG. 27B shows the rotary valve in a flow-blocking configuration.

FIG. 28A shows a sample collection whistle from a front-biased three-quarters view. FIG. 28B shows a sample collection whistle from a right side view. FIG. 28C shows a sample collection whistle from a top view.

FIG. 29A shows a sample capture cartridge loaded into the sample collection whistle from a front-biased three-quarters view. FIG. 29B shows a sample capture cartridge loaded into the sample collection whistle from a right side view. FIG. 29C shows a sample capture cartridge loaded into the sample collection whistle from a top view.

FIGS. 30A-30C show cross-sectional views of the sample collection whistle of FIGS. 28A-28C and 29A-29C. FIG. 30A shows a right side cross-sectional view of the sample collection whistle of FIG. 28C taken along line J-J. FIG. 30B shows a right side cross-sectional view of the sample collection whistle of FIG. 29C taken along line K-K. FIG. 30C shows a right-front biased three-quarters view of the sample collection whistle of FIG. 29C taken along line L-L.

FIGS. 31A-31E show various views of an embodiment of a base unit. FIG. 31A shows a top-right biased three-quarters view of the base unit. FIG. 31B shows a front view of the base unit. FIG. 31C shows a rear view of the base unit. FIG. 31C shows a right side view of the base unit. FIG. 31D shows a left side view of the base unit.

FIGS. 33A-33C show various views of an embodiment of a developer tank. FIG. 33A shows a side view of the developer tank. FIG. 33B shows a bottom-biased three-quarters view of the developer tank. FIG. 33C shows a cross-sectional view of the developer tank.

FIG. 34A shows the nozzle in a closed position. FIG. 34B shows the nozzle in an open position.

FIG. 35A shows the bleed valve in a closed position. FIG. 35B shows the bleed valve in an open position.

DETAILED DESCRIPTION OF SPECIFIC EMBODIMENTS

Sample Collection Cartridge

Figure 1A:
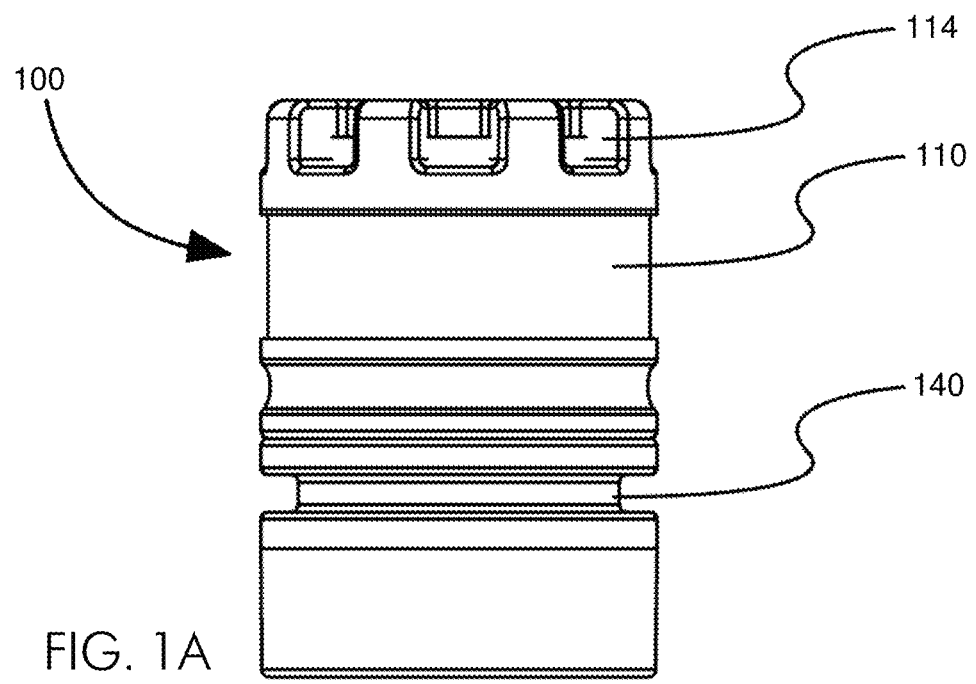

FIG. 1A illustrates an embodiment of a sample capture cartridge 100 that may be used to collect a fluid sample, e.g., to collect a fluid sample according to any of the number of methods disclosed herein. The sample capture cartridge 100, as shown in FIG. 1A, includes a cartridge lens cap 110 that has a number of lens cap vents 114 and fits on a cartridge desiccant canister 140, e.g., fits securely on the cartridge desiccant canister 140. The sample capture cartridge 100 may have a diameter of between about 5-30 mm, between about 5.5-28 mm, between about 6-26 mm, between about 6.5-24 mm, between about 7-22 mm, between about 7.5-20 mm, between about 8-18 mm, between about 8.5-16 mm, between about 9-14 mm, between about 9.5-12 mm, or any other diameter that advantageously facilitates use and collection of samples as disclosed herein. The sample capture cartridge 100 may have a combined height, including at least both the cartridge lens cap 110 and the cartridge desiccant canister 140, of between about 6-40 mm, between about 7-38 mm, between about 8-36 mm, between about 9-34 mm, between about 10-32 mm, between about 11-30 mm, between about 12-28 mm, between about 13-26 mm, between about 14-24 mm, between about 15-22 mm, between about 16-20 mm, or any other combined height that facilitates use and collection of samples as disclosed herein.

Figure 1B:
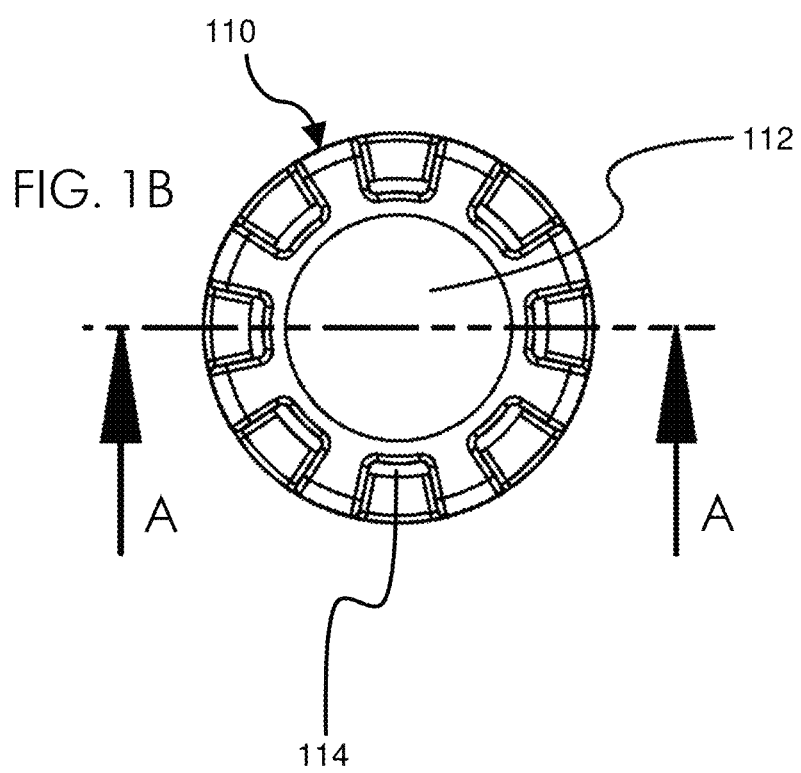

FIG. 1B illustrates a top view of the sample capture cartridge 100 of FIG. 1A, showing the cartridge lens cap 110 surrounded by several, e.g., eight, lens cap vents 114. Various embodiments of a cartridge lens cap 110 are discussed in more detail in connection with FIGS. 4A-4G.

FIG. 1C illustrates a sectional view of the sample capture cartridge 100 of FIG. 1A taken along line A-A. Additional detail regarding the interaction of the various pieces of the sample capture cartridge 100 is provided herein. Generally, the quantity of silica 120 resides in the interior of the porous bowl 130. The porous bowl 130 containing the quantity of silica 120 is fit into the cartridge lens cap 110 such that the edges of the porous bowl 130 prevent the silica 120 from falling out of the lens cap vents 114 of the cartridge lens cap 110. The cartridge lens cap 110 (already containing the porous bowl 130 containing the silica 120) is fitted onto the cartridge desiccant canister 140. The cartridge desiccant canister 140 contains a quantity of desiccant 150 held in place, under a ported upper surface, by a cartridge desiccant retainer 160, which also has at least one port. Therefore, the sample capture cartridge 100 defines a continuous flow path therethrough. As will be understood with reference to FIG. 1C and FIG. 3, in at least one embodiment, the continuous flow path proceeds from the base of the sample capture cartridge 100, into the bottom opening of the cartridge desiccant canister 140, through the ports of the cartridge desiccant retainer 160, through the desiccant 150 (held between the cartridge desiccant retainer 160 and the cartridge desiccant canister 140) through the ports in the cartridge desiccant canister 140, through the canister cavity 144, through the base of the porous bowl 130, through the silica 120, through the sides of the porous bowl 130, and out through the lens cap vents 114. Of course, one of ordinary skill in the art will understand that various modifications to this flow path may be made.

FIG. 1D illustrates the sample capture cartridge 100 shown in FIGS. 1A and 1C from the bottom. The cartridge desiccant canister 140 may be seen, as well as the cartridge desiccant retainer 160 holding in a quantity of desiccant 150. Additionally, a desiccant retainer notch 162 may be seen.

The cartridge lens cap 110 is shaped generally like a cylinder and includes a lens cap window 112 and at least one lens cap vent 114. In some embodiments, the cartridge lens cap 110 may have shapes other than a cylinder. For example, the cartridge lens cap 110 may be have four side, five sides, six sides, seven sides eight sides, or any other number of sides. Circular cartridge lens caps 110 may advantageously simplify the manufacturing process, but one of ordinary skill in the art will easily understand that a cartridge lens cap 110 having other numbers of sides may be used. The cartridge lens cap 110 may have a diameter of between about 5-30 mm, between about 5.5-28 mm, between about 6-26 mm, between about 6.5-24 mm, between about 7-22 mm, between about 7.5-20 mm, between about 8-18 mm, between about 8.5-16 mm, between about 9-14 mm, between about 9.5-12 mm, or any other diameter that advantageously facilitates use and collection of samples as disclosed herein. The cartridge lens cap 110 may have a height of between about 3-26 mm, between about 4-24 mm, between about 5-22 mm, between about 6-20 mm, between about 7-18 mm, between about 8-16 mm, between about 9-14 mm, between about 10-12 mm, between about 26-30 mm, or any other height that advantageously facilitates use and collection of samples as disclosed herein.

Figure 2A:
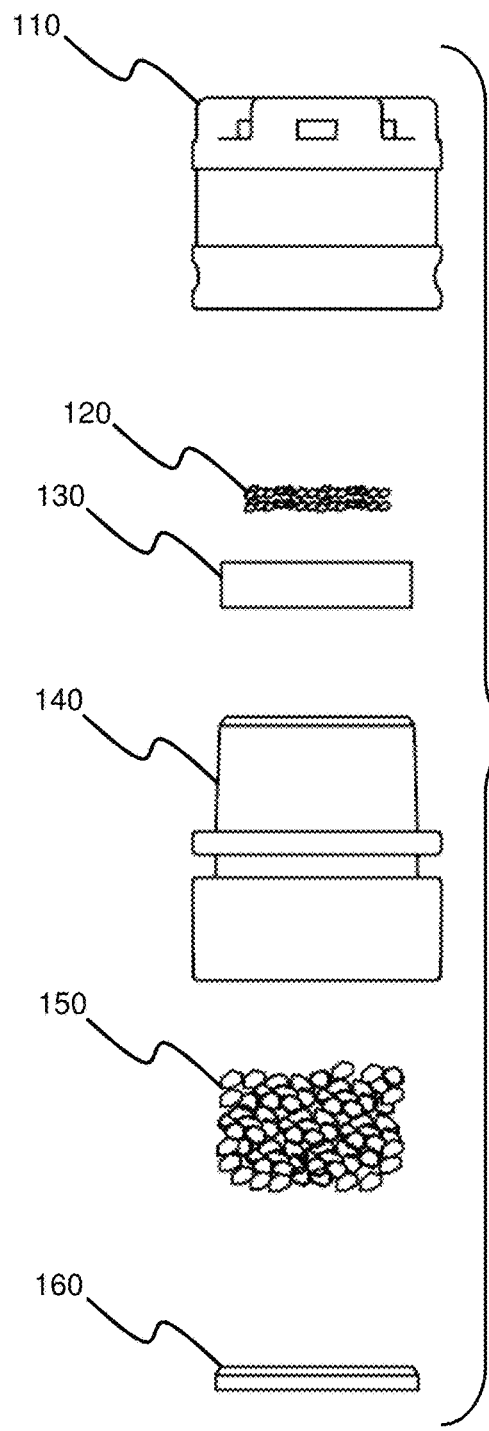
FIGS. 2A-2B show exploded views of an embodiment of a sample capture cartridge.
Figure 2B:
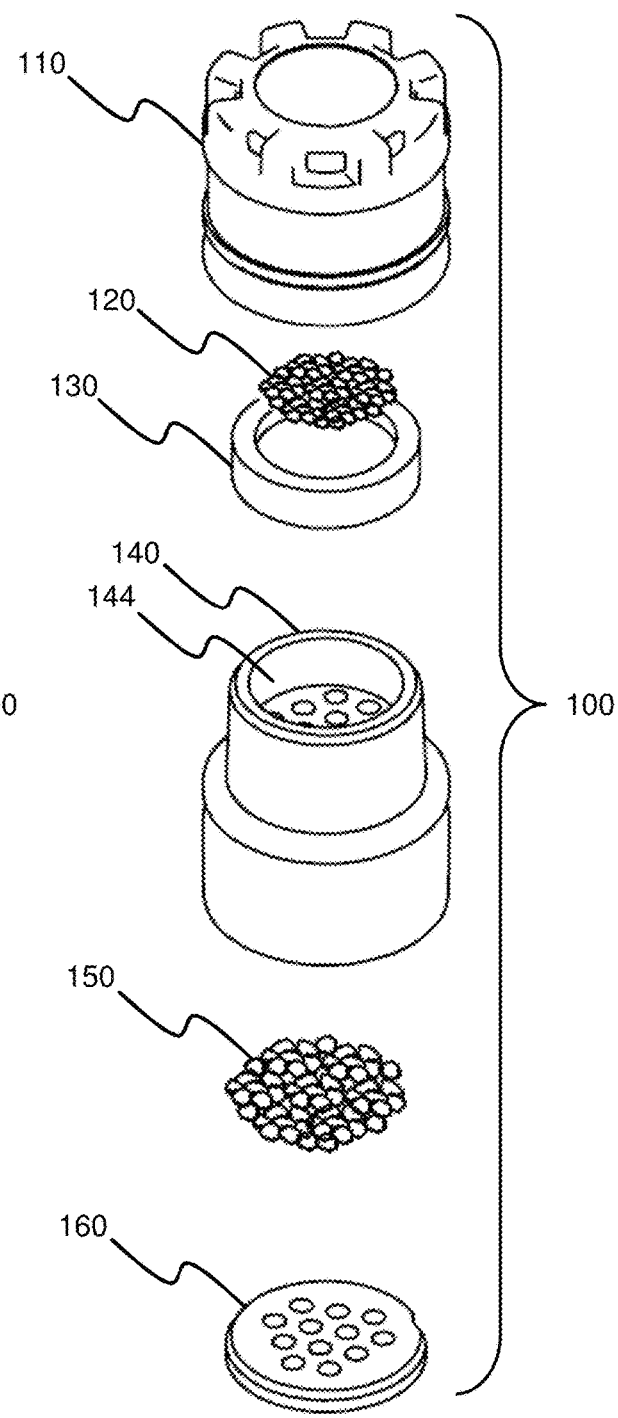

FIGS. 2A-2B illustrate exploded views of an embodiment of a sample capture cartridge 100, e.g., the sample capture cartridge 100 of FIG. 1A. The sample capture cartridge 100 of FIGS. 2A-2B includes a cartridge lens cap 110, a quantity of silica 120, a porous bowl 130, a cartridge desiccant canister 140, a quantity of desiccant 150 and a cartridge desiccant retainer 160. FIG. 1C illustrates how these components may fit together.

Figure 4A:
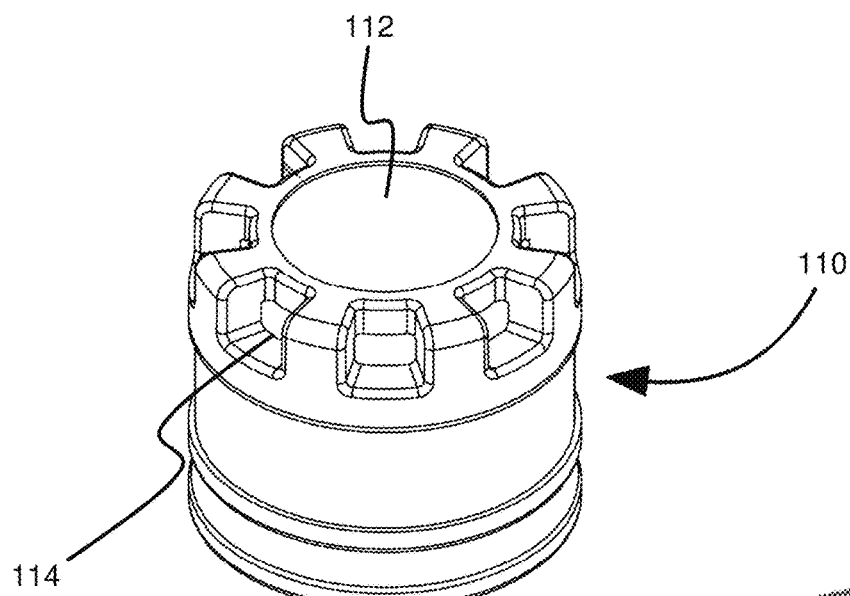
Figure 4B:
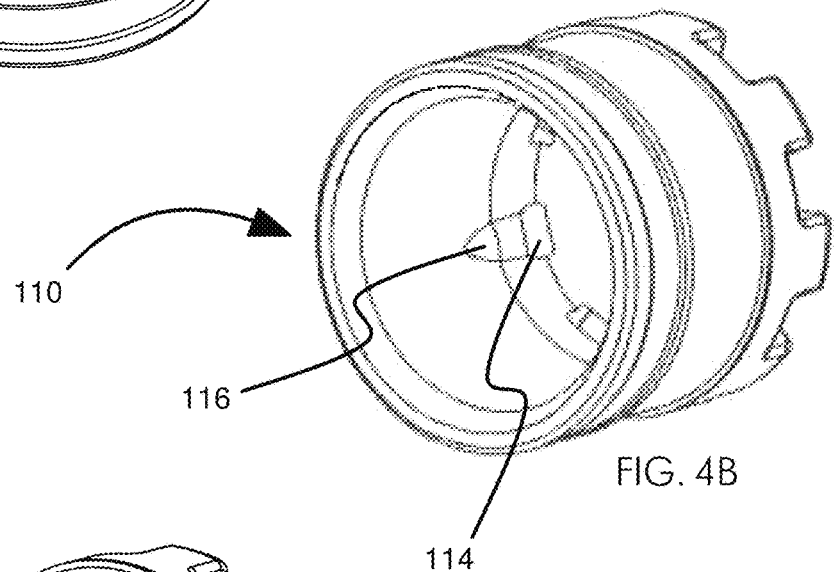
Figure 4C:
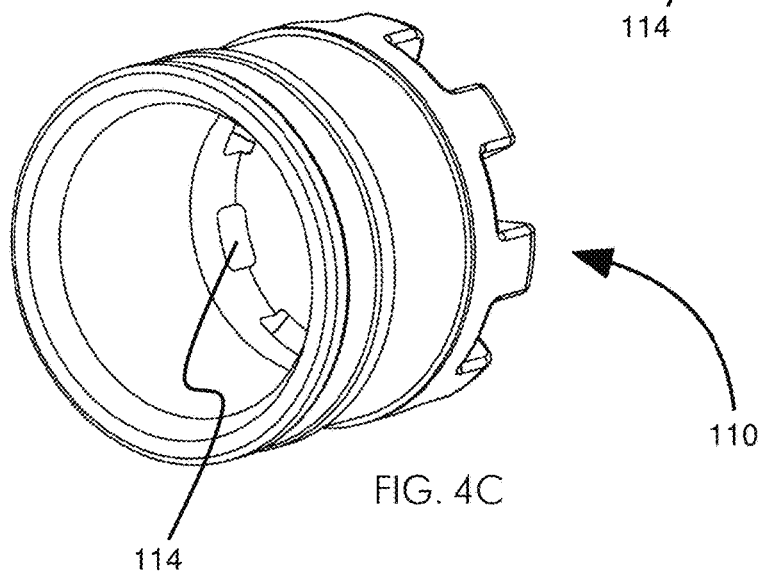

FIGS. 4A-4G illustrate various views of an embodiment of a cartridge lens cap 110. FIG. 4A shows an embodiment of a cartridge lens cap 110 having a lens cap window 112 surrounded by eight lens cap vents 114. FIG. 4B shows an embodiment of a cartridge lens cap 110 from the bottom such that at least three of the lens cap vents 114 and an undercut 116 may be seen. FIG. 4C shows an embodiment of a cartridge lens cap 110 from the bottom such that at least three of the lens cap vents 114 may be seen. FIG. 4D shows a top view of an embodiment of a cartridge lens cap 110 having a lens cap window 112 surrounded by eight lens cap vents 114. FIG. 4E shows a side view of an embodiment of a cartridge lens cap 110 having a lens cap window 112 and several lens cap vents 114. FIG. 4F shows a side view cut away of the cartridge lens cap 110 of FIG. 4E taken alone line B-B and having a lens cap window 112 and several lens cap vents 114. FIG. 4G shows a bottom view of an embodiment of a cartridge lens cap 110 having a lens cap window 112 and eight lens cap vents 114.

One of ordinary skill in the art will understand that various features of the cartridge lens cap 110 may be changed. For example, certain features of the cartridge lens cap 110 that may be changed include, but are not limited to: the size, shape, and number of the lens cap vents 114; the size, shape, and thickness of the lens cap window 112; the diameter of the cartridge lens cap 110; and the height of the cartridge lens cap 110. The embodiment of the cartridge lens cap 110 shown in FIGS. 4A-4G includes eight lens cap vents 114. Other numbers of vents may be used. In some embodiments, the cartridge lens cap 110 has at least 1 vent, at least 2 vents, at least 3 vents, at least 4 vents, at least 5 vents, at least 6 vents, at least 7 vents, at least 8 vents, at least 9 vents, at least 10 vents, at least 11 vents, at least 12 vents, between 12 and 20, or any number of vents that advantageously facilitates sample collection as disclosed herein.

In some embodiments, each lens cap vent 114 is formed in a generally radial fashion (e.g., the sides of each lens cap vent 114 are not parallel), as shown in FIGS. 4A & 4D. In some embodiments, each lens cap vent 114 is between about 15 and 25 degrees wide. In other embodiments, each lens cap vent 114 is less than about 5 degrees wide, less than about 10 degrees wide, less than about 15 degrees wide, less than about 20 degrees wide, less than about 25 degrees wide, less than about 30 degrees wide, less than about 40 degrees wide, less than about 50 degrees wide, less than about 60 degrees wide, less than about 70 degrees wide, less than about 80 degrees wide, less than about 90 degrees wide, or any other degree of width that advantageously facilitates sample collection as disclosed herein. In some embodiments, each lens cap vent 114 is formed as a notch in the corner of the cartridge lens cap 110 (e.g., the sides of each lens cap vent 114 are parallel, or substantially parallel).

In some embodiments each lens cap vent 114 has three sides (e.g., is a trapezoidal cut or void in the edge of the cartridge lens cap 110). In other embodiments, each lens cap vent 114 has only two sides (e.g., is a v-shaped cut or void in the edge of the cartridge lens cap 110).

In some embodiments, such as the embodiment shown in FIG. 4D, the lens cap vents 114 are spaced evenly around the edge of the cartridge lens cap 110 (e.g., about every 45 degrees). In other embodiments, the lens cap vents 114 are grouped in patterns. In some embodiments, the lens cap vents 114 are arranged in patterns so as to facilitate spiral outflow of fluid from the interior of cartridge lens cap 110 of the sample capture cartridge 100 (as is disclosed herein). In some embodiments, the lens cap vents 114 are arranged in patterns so as to facilitate turbulent outflow of fluid from the interior of cartridge lens cap 110 of the sample capture cartridge 100 (as is disclosed herein).

In some embodiments, the lens cap vents 114 are formed at a substantially right angle with respect to the lens cap window 112, as shown in FIG. 4F. In some embodiments, the lens cap vents 114 are cut or formed obliquely in the edge of the cartridge lens cap 110 (rather than radially) to facilitate spiral outflow of fluid from the interior of the cartridge lens cap 110 of the sample capture cartridge 100. In some embodiments, the lens cap vents 114 are cut or formed obliquely in the edge of the cartridge lens cap 110 (rather than radially) to facilitate turbulent outflow of fluid from the interior of the cartridge lens cap 110 of the sample capture cartridge 100.

In some embodiments, such as the embodiment shown in FIG. 4F, the lens cap vents 114 have a vertical depth (e.g., from the top of the cartridge lens cap 110 to the base of each lens cap vent 114. Along with other features of the cartridge lens cap 110, the depth of the lens cap vents 114 may define the size of the various lens cap vents 114. In some embodiments, the depth of the lens cap vents 114 is about 1 mm. In some embodiments, the depth of the lens cap vents 114 is in the range of between about 0.01-4 mm, between about 0.05-3.8 mm, between about 0.1-3.6 mm, between about 0.15-3.4 mm, between about 0.2-3.2 mm, between about 0.25-3 mm, between about 0.30-2.8 mm, between about 0.35-2.6 mm, between about 0.40-2.4 mm, between about 0.45-2.2 mm, between about 0.5-2 mm, between about 0.55-1.8 mm, between about 0.6-1.6 mm, between about 0.65-1.4 mm, between about 0.7-1.2 mm, between about 0.75-1, or any other depth that advantageously facilitates airflow through the sample capture cartridge 100 and/or analysis of a sample through the lens cap window 112 as disclosed herein.

As shown in FIGS. 4A, 4D, 4F, and 4G, the top of the cartridge lens cap 110 may include a lens cap window 112. The lens cap window 112 may be approximately in the center of the top of the cartridge lens cap 110. As is discussed herein, the lens cap window 112 may be used in an optical analysis of a sample (e.g., a photosensor measures a change in light reflectance of a substance held behind the lens cap window 112). For example, various embodiments of base units may use photosensors or optical sensors to sense or detect one or more optical characteristics through the lens cap window 112 (e.g., an optical characteristic of the silica 120 or a blended bowl). As such, in some embodiments, the lens cap window 112 may have a high degree of transparency. As used herein, transparency is the amount of light that passes through a barrier (e.g., the lens cap window 112)—that is to say the total amount of light subtracting the amount of light reflected by the barrier and subtracting the amount of light absorbed by the barrier.

In some embodiments, the lens cap window 112 has a transparency to the wavelength of light being measured (e.g., some materials have different transparencies to different wavelengths of light) of at least about 60%, at least about 65% at least about 70% at least about 75%, at least about 80%, at least about 82.5%, at least about 85%, at least about 86%, at least about 87%, at least about 88%, at least about 89%, at least about 90%, at least about 92%, at least about 93%, at least about 94%, at least about 95%, at least about 96%, at least about 97%, at least about 98%, at least about 99%, or any of amount of transmittance that advantageously facilitates analysis of a sample through the lens cap window 112 as disclosed herein. Of course, a lens cap window 112 having a transmission of less than about 60% may be used; however, one of ordinary skill in the art will understand that other parameters of the system may need to be adjusted to compensate for the losses due to reflectance and absorbance by the lens cap window 112.

As shown in FIG. 1B, the lens cap window 112 may be circular. The lens cap window 112 may have other shapes. For example, the lens cap window 112 may have the same number of sides as the cartridge lens cap 110 of which it is a part (e.g., a four-sided cartridge lens cap 110 may have a four-sided lens cap window 112, and an eight-sided cartridge lens cap 110 may have an eight-sided lens cap window 112). In some embodiments, the lens cap window 112 forms the entire top of the cartridge lens cap 110 (e.g., the at least one lens cap vent 114 is cut into or formed in an edge of the lens cap window 112 that forms the top of the cartridge lens cap 110).

As shown in FIG. 4F, the lens cap window 112 has a thickness. In some embodiments, the thickness of the lens cap window 112 is less than the depth (from top to bottom) of the lens cap vents 114: in that way, the thickness of the lens cap window 112 and the vertical depth of the lens cap vents 114 defines the thickness of the lens cap vents 114 (e.g., the size of the lens cap vents 114 may be defined by the width of each lens cap vent 114, the vertical depth of each lens cap vent 114, the radial depth of each lens cap vent 114, and the thickness of the lens cap window 112). In some embodiments, the thickness of the lens cap window 112 is about 1 mm. In some embodiments, the thickness of the lens cap window 112 is in the range of between about 0.5-3 mm, between about 0.55-2.8 mm, between about 0.6-2.6 mm, between about 0.65-2.4 mm, between about 0.7-2.2 mm, between about 0.75-2 mm, between about 0.8-1.8 mm, between about 0.85-1.6 mm, between about 0.9-1.4 mm, between about 0.95-1.2 mm, or any other thickness that advantageously facilitates airflow through the sample capture cartridge 100 and/or analysis of a sample through the lens cap window 112 as disclosed herein.

As best seen in FIGS. 4D, 4F and 4F, in some embodiments, the lens cap vents 114 are cut radially into the top of the cartridge lens cap 110 deeper than the thickness of the side wall of the cartridge lens cap 110. In some embodiments, the lens cap vents 114 are cut into or formed in only the sidewall of the cartridge lens cap 110 (e.g., they do not extend into the top of the cartridge lens cap 110). In such embodiments, the top of the cartridge lens cap 110 may approximately resemble a disk set on a crenulated cylinder (e.g., in this case, the lens cap vents 114 would exit only to the "side of the cartridge lens cap 110 rather than also forming an exit on/from the top of the cartridge lens cap 110). In some embodiments, the entire top of the cartridge lens cap 110 is formed out of the lens cap window 112. In some embodiments, the top of the cartridge lens cap 110 is a solid disc (e.g., no lens cap vent 114 is cut/formed into the top, but is rather cut/formed into the side of the cartridge lens cap 110) and the lens cap window 112 is only in the center of the top of the cartridge lens cap 110.

The cartridge lens cap 110 may be configured to accept and hold the porous bowl 130. To hold the porous bowl 130, the cartridge lens cap 110 may have a retention or holding feature on its inner wall. In some embodiments, the cartridge lens cap 110 may have a continuous or partial ledge or step on its inner wall. For example, the cartridge lens cap 110 may have a continuous ramped step (e.g., ramped from the bottom, and flat on the top) that is spaced a distance from the inner surface of the top of the cartridge lens cap 110 substantially equal to the height of the porous bowl 130. Such a continuous ramped step may have a maximum width of about 0.13 mm. In other embodiments, a continuous ramped step may have a maximum width in the range of about 0.05-0.5 mm. In some embodiments, the retention or holding feature may not extend around the entirety of the cartridge lens cap 110. In some embodiments, as shown in FIG. 4B, the retention or holding feature may comprise one or more undercuts 116. The undercuts 116 may be present with or without a continuous or discontinuous ramped step. The undercut 116, as shown in FIG. 4B, may be a partial conical surface with a flat upper surface facing the top of the cartridge lens cap 110. Undercuts 116 may augment or replace a continuous or partial smaller retention or holding feature. In some embodiments, the cartridge lens cap 110 has no retention or holding feature and retains the porous bowl 130 through friction. In other embodiments, the porous bowl 130 is held within the cartridge lens cap 110 by the top surface of the cartridge desiccant canister 140 pushing up against the bottom of the porous bowl 130 which holds the top surface of the porous bowl 130 against the inner surface of the top of the cartridge lens cap 110.

FIGS. 4H-4J illustrate various views of an embodiment of a two-part cartridge lens cap 110. The two-part cartridge lens cap 110 may be similar in structure and function to the other various embodiments of cartridge lens caps 110 disclosed herein, such as the cartridge lens cap 110 of FIGS. 4A-4G. While some features of the two-part cartridge lens cap 110 may be the same or identical to those other cartridge lens caps 110 disclosed herein, they need not be the same or even similar. Like other embodiments of the cartridge lens cap 110 disclosed herein, the two-part cartridge lens cap 110 may include a lens cap window 112 and at least one lens cap vent 114.

The cartridge lens cap 110 shown in FIGS. 4H-4J includes a cartridge lens cap upper portion 111 and a cartridge lens cap lower portion 113. The cartridge lens cap upper portion 111 may have an engagement portion that couples the cartridge lens cap upper portion 111 to the cartridge lens cap lower portion 113. As shown in FIGS. 4H-4J, the engagement portion may comprise a foot 117 on the cartridge lens cap upper portion 111 and an undercut 118 on the cartridge lens cap lower portion 113, in the wall, e.g., the inner lateral wall, of the cartridge lens cap lower portion 113. Other different types of engagement or coupling portions may be used, including, but not limited to, threads, friction fit, etc.

In some embodiments, the engagement portion of the cartridge lens cap 110 includes foot 117 extending downwards from the cartridge lens cap upper portion 111 and extending around the cartridge lens cap upper portion 111. In some embodiments, the foot 117 extends substantially the entire way around the cartridge lens cap upper portion 111, e.g., a distance of about 360°. In some embodiments, the foot 117 extends around the cartridge lens cap upper portion 111 less than about 360°. In some embodiments, the foot 117 comprises a plurality of distinct feet, e.g., multiple downward protrusions, rather than a single ring. In some embodiments, the foot 117 comprises a number of feet 117 between about 3-18, between about 4-16, between about 5-14, between about 6-12, and between about 7-10.

In some embodiments, the cartridge lens cap upper portion 111 comprises an upper portion mating surface 170 surrounding the foot 117. The upper portion mating surface 170 may be a substantially level or flat surface configured to mate with, e.g., closely mate with, a corresponding surface on the cartridge lens cap lower portion 113.

In some embodiments, the undercut 118 of the cartridge lens cap lower portion 113 is a mirror image or negative of the foot 117 of the cartridge lens cap upper portion 111. In this way, the foot 117 may "snap" into the undercut 118 of the cartridge lens cap lower portion 113. In embodiments in which the cartridge lens cap upper portion 111 has more than one foot 117, the undercut 118 of the cartridge lens cap lower portion 113 may include protrusions in the undercut 118 to index the cartridge lens cap upper portion 111 with respect to the cartridge lens cap lower portion 113. In this way, exacting alignment of the cartridge lens cap upper portion 111 with respect to the cartridge lens cap lower portion 113 may be reproducibly achieved.

In some embodiments, the cartridge lens cap lower portion 113 comprises a lower portion mating surface 180 on its uppermost surface. The lower portion mating surface 180 may be a substantially level or flat surface configured to mate with, e.g., closely mate with, a corresponding surface on the cartridge lens cap upper portion 111. For example, the lower portion mating surface 180 of the cartridge lens cap lower portion 113 may be configured to mate with the upper portion mating surface 170 of the cartridge lens cap upper portion 111. In some embodiments, the lower portion mating surface 180 may be configured to substantially sealingly mate with the upper portion mating surface 170 of the cartridge lens cap upper portion 111 when the cartridge lens cap upper portion 111 and the cartridge lens cap lower portion 113 are engaged (e.g., when the foot 117 engages the undercut 118).

In some embodiments, the cartridge lens cap lower portion 113 includes a shelf 115 extending radially inward below the undercut 118. The shelf 115 may serve as a surface against which the foot 117 of the cartridge lens cap upper portion 111 may abut when fully in place in the undercut 118. In some embodiments, the shelf 115 extends radially inward past the innermost surface of the foot 117. In this way, the shelf 115 may also support a porous bowl 130, holding the porous bowl 130 in the cartridge lens cap 110 between the cartridge lens cap upper portion 111 and the cartridge lens cap lower portion 113.

FIG. 4I shows a cartridge lens cap upper portion 111 engaged with a cartridge lens cap lower portion 113, such that the foot 117 has fully engaged the undercut 118 and is abutting the shelf 115. FIG. 4J shows an assembled cartridge lens cap 110, including cartridge lens cap upper portion 111, a cartridge lens cap lower portion 113, and a porous bowl 130 held between the two. As can be seen, the shelf 115 of the cartridge lens cap lower portion 113 supports the porous bowl 130 and holds it securely within the cartridge lens cap upper portion 111.

A two-piece cartridge lens cap 110 may facilitate manufacture. In some embodiments, the cartridge lens cap 110 is manufactured by first placing a quantity of silica 120 in a porous bowl 130, which is placed on a stable and/or flat surface. A cartridge lens cap upper portion 111 is then placed in friction fit over the porous bowl 130. As can be seen in FIG. 4J, when the porous bowl 130 is fully in place within the cartridge lens cap upper portion 111, the bottom of the porous bowl 130 and the base of the foot 117 are substantially aligned. Therefore, the cartridge lens cap upper portion 111 can be installed over the porous bowl 130 with some force without risking damage to the porous bowl 130. The cartridge lens cap upper portion 111 may hold the porous bowl 130 by friction, e.g., the inner lateral walls of the cartridge lens cap upper portion 111 may engage the outer lateral walls of the porous bowl 130 such that the porous bowl 130 will not easily slide out of the cartridge lens cap upper portion 111 once installed. After the porous bowl 130 is installed in the cartridge lens cap upper portion 111, the cartridge lens cap upper portion 111 and the cartridge lens cap lower portion 113 may be engaged. As the porous bowl 130 is securely engaged with the cartridge lens cap upper portion 111, the construct of the cartridge lens cap upper portion 111 and the porous bowl 130 may be introduced to the cartridge lens cap lower portion 113 right-side-up (as shown in FIG. 4J) or upside-down. The construct of the porous bowl 130 and the cartridge lens cap upper portion 111 may simply be snapped into place within the cartridge lens cap lower portion 113 to complete the two-piece 110.

FIGS. 5A-5F illustrate various views of an embodiment of a porous bowl 130 that may be used in conjunction with the various systems and methods disclosed herein. FIG. 5A illustrates an embodiment of a porous bowl 130 from the side. FIG. 5B illustrates a side view cut-away of the porous bowl 130 of FIG. 5A taken along line C-C and showing the porous bowl's 130 bowl wall 132 and bowl base 134. FIG. 5C shows a top-biased three-quarters view of an embodiment of a porous bowl 130. FIG. 5D shows a top-biased three-quarters view of another embodiment of a porous bowl 130. FIG. 5E shows a top view of an embodiment of a porous bowl 130. FIG. 5F shows a bottom view of an embodiment of a porous bowl 130.

In some embodiments, the porous bowl 130 may be configured in a bowl shape. However, reference to this element as a bowl should not limit the scope of this disclosure. The porous element or member (e.g., bowl) may have any of a number of other shapes. For example the porous element or member (e.g., the porous bowl) may be a disc, a frit, a molded solid, a solid, a molded shape, a slice, etc.

The porous bowl 130 may be formed to match an inner surface of a cartridge lens cap 110. For example, the porous bowl 130 shown in FIGS. 5A-5F is configured to fit within a cartridge lens cap 110 having a substantially right angle where the side-wall(s) (e.g., the cylindrical side wall) of the cartridge lens cap 110 meet the top surface of the cartridge lens cap 110. The porous bowl 130 and the cartridge lens cap 110 may be configured to closely match (e.g., the porous bowl 130 is a negative of an internal surface of the cartridge lens cap 110) so that the porous bowl 130 prevents a substance or material (e.g., silica 120) contained within the porous bowl 130 from exiting the porous bowl 130 and cartridge lens cap 110 through the lens cap vents 114. In some embodiments, the porous bowl 130 may have rounded corners (e.g., a rounded external corner(s) matching a rounded internal corner(s) on an interior surface of the cartridge lens cap 110). While the porous bowl 130 is described with reference to the accompanying figures, one of ordinary skill in the art will understand that various features of the porous bowl 130 may be changed.

The porous bowl 130 may have a diameter, most simply seen in FIG. 5F. The diameter of the porous bowl 130 may be selected to closely match an internal diameter of the cartridge lens cap 110. It may be desirable that the porous bowl 130 fit snugly, tightly, immovably, or fixedly within the cartridge lens cap 110. The diameter of the porous bowl 130 may be between about 8-9 mm. In other embodiments, the diameter of the porous bowl 130 is between about 5-30 mm, between about 5.5-28 mm, between about 6-26 mm, between about 6.5-24 mm, between about 7-22 mm, between about 7.5-20 mm, between about 8-18 mm, between about 8.5-16 mm, between about 9-14 mm, between about 9.5-12 mm, or any other diameter that advantageously facilitates use and collection of samples as disclosed herein.

The porous bowl 130 may have a height, most simply seen in FIGS. 5A-5B. The bowl's height may be from the underside of the bowl base 134 to the top of the bowl wall 132. In some embodiments, the height of the porous bowl 130 is about 2 mm. In other embodiments, the height of the porous bowl 130 is between about 0.5-3 mm, between about 0.55-2.8 mm, between about 0.6-2.6 mm, between about 0.65-2.4 mm, between about 0.7-2.2 mm, between about 0.75-2 mm, between about 0.8-1.8 mm, between about 0.85-1.6 mm, between about 0.9-1.4 mm, between about 0.95-1.2 mm, or any other height that advantageously facilitates use and collection of samples as disclosed herein.

The porous bowl 130 may have a bowl depth, most simply seen in FIG. 5B. The bowl depth may be from the top side of the bowl base 134 to the top of the bowl wall 132. In some embodiments, the bowl depth is about 0.8 mm. In other embodiments, the bowl depth is in the range of between about 0.01-2.8 mm, between about 0.05-2.6 mm, between about 0.1-2.4 mm, between about 0.15-2.2 mm, between about 0.2-2 mm, between about 0.25-1.8 mm, between about 0.30-1.6 mm, between about 0.35-1.4 mm, between about 0.40-1.2 mm, between about 0.45-1 mm, or any other depth that advantageously facilitates airflow through the sample capture cartridge 100 and/or analysis of a sample through the lens cap window 112 as disclosed herein.

As will be explained in more detail herein, the porous bowl 130 may contain a reactant that collects and/or reacts with a sample and that experiences a physical change that may by assessed or measured through the lens cap window 112. Thus, it is desirable that the porous bowl 130 permit fluid flow therethrough. One of ordinary skill in the art will understand that the pore size of the porous bowl 130 is dependent on at least two factors, including, but not limited to: 1) the necessary fluid flow rate through the porous bowl 130 (e.g., through the sample capture cartridge 100) (it will be easily understood that in some embodiments the porous bowl 130 is the individually greatest restriction to fluid flow through the sample capture cartridge 100) and 2) the particle size that must be held by the porous bowl 130 (e.g., the particle size of the silica 120 material). Stated differently, fluid flow rate through the sample capture cartridge 100 may be limited by the porous bowl 130 and, more specifically, by the pore size of the porous bowl 130. Additionally, the material contained within the porous bowl 130 may have a quite small particle size, and it may be desirable to have a pore size of the porous bowl 130 that prevents all or substantially all of the material contained within the porous bowl 130 from passing through the bowl base 134 or bowl wall 132 of the porous bowl 130 (e.g., it may be desirable to avoid the porous bowl 130 acting like a sieve to the material it contains).

In some embodiments, the porous bowl 130 has a pore size of about 130 μm. In some embodiments, the porous bowl 130 has a pore size less than about 250 μm. In some embodiments, the porous bowl 130 has a pore size in the range of between about 5-400 μm, between about 10-380 μm, between about 15-360 μm, between about 20-340 μm, between about 25-320 μm, between about 30-300 μm, between about 35-280 μm, between about 40-260 μm, between about 45-240 μm, between about 50-220 μm, between about 55-200 μm, between about 60-180 μm, between about 65-175 μm, between about 70-170 μm, between about 75-165 μm, between about 80-160 μm, between about 85-155 μm, between about 90-150 μm, between about 95-145 μm, between about 100-140 μm, between about 105-135 μm, between about 110-130 μm, between about 115-125 μm, or any other pore size that both strikes an advantageous balance between retaining any particle(s) within the porous bowl 130 (e.g., preventing exit of the substance intended to be held within the bowl) and allowing the desired fluid flow rate through the porous bowl 130.

In some embodiments, the porous bowl 130 has dimensions and pore size that permits a flow rate through the porous bowl 130 of between about 300-750 ml/min (e.g., the flow rate may be due to or under the pressure of a user blowing into a device holding the sample capture cartridge and directing the breath into and through the cartridge). In some embodiments, the porous bowl 130 is configured to permit a flow rate through the porous bowl 130 of between about 50-7000 ml/min, between about 75-6750 ml/min, between about 100-6500 ml/min, between about 125-6250 ml/min, between about 150-6000 ml/min, between about 175-5750 ml/min, between about 200-5500 ml/min, between about 225-5250 ml/min, between about 250-5000 ml/min, between about 275-4750 ml/min, between about 300-4500 ml/min, between about 325-4250 ml/min, between about 350-4000 ml/min, between about 375-3750 ml/min, between about 400-3500 ml/min, between about 425-3250 ml/min, between about 450-3000 ml/min, between about 475-2750 ml/min, between about 500-2500 ml/min, between about 525-2250 ml/min, between about 550-2000 ml/min, between about 575-1750 ml/min, between about 600-1500 ml/min, between 625-1250 ml/min, between about 650-1000 ml/min, between about 675-750 ml/min, or any other flow rate that facilitates collection of sample from a fluid flowing through the sample capture cartridge 100 as disclosed herein. In some embodiments, the porous bowl 130 is configured to permit a flow rate through the porous bowl 130 of between about 7000-10000 ml/min.

In some embodiments, the porous bowl 130 is configured to hold a material (e.g., silica beads) having an average particle size of about 80 μm. In some embodiments, the porous bowl 130 is configured to hold a material having an average particle size of greater than about 40 μm, greater than about 45 μm, greater than about 50 μm, greater than about 55 μm, greater than about 60 μm, greater than about 65 μm, greater than about 70 μm, greater than about 75 μm, greater than about 80 μm, greater than about 85 μm, greater than about 90 μm, greater than about 95 μm, greater than about 100 μm, greater than about 110 μm, greater than about 120 μm, greater than about 130 μm, greater than about 140 μm, greater than about 150 μm, greater than about 160 μm, greater than about 170 μm, greater than about 180 μm, greater than about 190 µm, greater than about 200 µm, greater than about 220 µm, greater than about 240 µm, greater than about 260 µm, greater than about 280 µm, greater than about 300 µm, greater than about 320 µm, greater than about 340 µm, greater than about 360 µm, greater than about 380 µm, greater than about 400, or any other size of particle that advantageously facilitates sample capture and analysis as disclosed herein. In some embodiments, the pore size of the porous bowl 130 is larger (e.g., only slightly larger) than the particle size of the material to be contained within the porous bowl 130. In some embodiments, the pore size of the porous bowl 130 is smaller than the particle size of the material to be contained within the porous bowl 130.

The material held within the porous bowl 130 may be an unreactive base material or substrate, such as silica, silica gel, silica wool, glass, nitrocellulous, a sodium silicate derivate, or metal oxide, to which a reactant has been attached to cause the base material to become functionalized. The base material may be in the form of particles of various configurations (e.g., beads), although this need not be the case. In some embodiments the material contained within the porous bowl 130 is silica 120. The silica 120 may be functionalized with an amine (e.g., aminated). For example, an amine (which may later react with a sample of interest, e.g., an analyte of interest) may be bound to the surface of the silica beads or particles.

In some embodiments, the particles comprising the silica 120 are substantially round or spherical and have a particle size (e.g., an average particle size) of about 50 µm. In some embodiments the particles comprising the silica 120 have a particle size (e.g., an average particle size of less than about 300 µm, less than about 280 µm, less than about 260 µm, less than about 240 µm, less than about 220 µm, less than about 200 µm, less than about 180 µm, less than about 160 µm, less than about 140 µm, less than about 120 µm, less than about 100 µm, less than about 90 µm, less than about 80 µm, less than about 70 µm, less than about 60 µm, less than about 50 µm, less than about 40 µm, less than about 30 µm, less than about 20, or any other diameter that advantageously facilitates sample flow through the silica 120 and interaction of the silica 120 with the analyte of interest contained within the fluid sample. In some embodiments, the particles comprising the silica 120 have a particle size (e.g., an average particle size in the range of between about 37-53 µm, between about 53-88 µm, or between about 88-105 µm.

In some embodiments, the quantity of silica 120 may fill the porous bowl 130 more than about 50%, more than about 55%, more than about 60%, more than about 60%, more than about 70%, more than about 75%, more than about 80%, more than about 85%, more than about 90%, more than about 95%, or any other amount that facilitates capture/collection and analysis of a sample as disclosed herein.

In some embodiments, the volume of silica 120 contained within the porous bowl 130 is less than about 5 ml, less than about 4.5 ml, less than about 4 ml, less than about 3.5 ml, less than about 3 ml, less than about 2.5 ml, less than about 2 ml, less than about 1.5 ml, less than about 1.4 ml, less than about 1.3 ml, less than about 1.2 ml, less than about 1.1 ml, less than about 1 ml, less than about 0.9 ml, less than about 0.8 ml, less than about 0.7 ml, less than about 0.6 ml, less than about 0.5 ml, less than about 0.4 ml, less than about 0.3 ml, less than about 0.2 ml, less than about 0.1 ml, or any other volume that facilitates capture/collection and analysis of a sample as disclosed herein.

In some embodiments, rather than using silica beads or particles, other chemistry substrates or base materials are used, such as sodium silicate derivates and/or silica/quartz wool. For example, a 4"×1" strip of silica wool can put in a solution of 1.6 ml APTES+3.2 ml propanol+3.2 ml sulfuric acid and heated to 80° C. for 2 hours and then 110° C. for 1 hour. The result is silica wool conjugated with primary amine. These substrates may have different geometries, such as planar, sheets, etc. (e.g., they may be cut or formed into disks that can be place in the porous bowl 130).

FIGS. 6A-6C illustrate various views of an embodiment of a cartridge desiccant canister 140. FIG. 6A shows an embodiment of a cartridge desiccant canister 140 from the top, such that the inside of the canister cavity 144 and the several canister sample ports 142 may be seen. FIG. 6B shows an embodiment of a cartridge desiccant canister 140 from the bottom. FIG. 6C illustrates a side view cut-away of the cartridge desiccant canister 140 of FIG. 6B taken along line D-D and showing the canister cavity 144 and cross-sections of various canister sample ports 142. The canister sample ports 142 direct sample fluid from the opening into the canister cavity 144 and towards the porous bowl 130 and the silica 120 it contains. Therefore, the canister sample ports 142 may advantageously have characteristics (e.g., shape, size, direction, etc.) that promote thorough and efficient mixing of the sample fluid with the silica 120 contained within the porous bowl 130. In some embodiments, such efficient mixing is achieved by inducing turbulent flow of the sample fluid. In some embodiments, the canister sample ports 142 are shaped, arranged, and oriented to increase the turbulence of fluid flow and/or mixing of the sample fluid with the silica 120 contained in the porous bowl 130.

In some embodiments, as shown in FIGS. 6A and 6B, the cartridge desiccant canister 140 may have 12 individual canister sample ports 142. In some embodiments, the cartridge desiccant canister 140 may have different numbers of canister sample ports 142. For example, the cartridge desiccant canister 140 may have one canister sample port 142. The cartridge desiccant canister 140 may have less than about 2 canister sample ports 142, less than about 4 canister sample ports 142, less than about 6 canister sample ports 142, less than about 8 canister sample ports 142, less than about 10 canister sample ports 142, less than about 15 canister sample ports 142, less than about 20 canister sample ports 142, less than about 25 canister sample ports 142, less than about 30 canister sample ports 142, less than about 35 canister sample ports 142, less than about 40 canister sample ports 142, less than about 45 canister sample ports 142, less than about 50 canister sample ports 142, or any other number of canister sample ports 142 that promotes fluid flow through the sample capture cartridge 100 and efficient mixing of the fluid (e.g., the fluid containing the sample with the silica 120 contained in the porous bowl 130).

With continued reference to FIGS. 6A and 6B, the canister sample ports 142 may be round. However, the canister sample ports 142 may have other shapes. In some embodiments, the canister sample ports 142 are triangular, rectangular, pentagonal, or hexagonal. Any shape of canister sample ports 142 may be used that advantageously promotes fluid flow through the sample capture cartridge 100 and efficient mixing of the fluid (e.g., the fluid containing the sample with the silica 120 contained in the porous bowl 130). In some embodiments, connected shapes are used as canister sample ports 142, e.g., "plus" (e.g., "+") shaped holes, linear shaped holes (e.g., "−"), etc. In some embodiments, the canister sample ports 142 are distributed evenly across the surface defining the bottom of the canister cavity 144. In some embodiments, the canister sample ports 142 are oriented more toward the center of the surface defining the bottom of the canister cavity 144 (e.g., increase in concentration closer to the center of the cartridge desiccant canister 140).

As can be seen in FIG. 6C, the canister sample ports 142 may be oriented substantially vertically through the cartridge desiccant canister 140. That is to say that the canister sample ports 142 may extend through the cartridge desiccant canister 140 at approximately a right angle to the portion of the cartridge desiccant canister 140 that forms the bottom of the canister cavity 144. In some embodiments, the canister sample ports 142 extend through the cartridge desiccant canister 140 at an angle. In some embodiments the canister sample ports 142 extend through the cartridge desiccant canister 140 at an angle of less than about 2 degrees off perpendicular, less than about 4 degrees off perpendicular, less than about 6 degrees off perpendicular, less than about 8 degrees off perpendicular, less than about 10 degrees off perpendicular, less than about 15 degrees off perpendicular, less than about 20 degrees off perpendicular, less than about 25 degrees off perpendicular, less than about 30 degrees off perpendicular, less than about 35 degrees off perpendicular, less than about 40 degrees of perpendicular, less than about 45 degrees off perpendicular, or any other angle that advantageously promotes fluid flow through the sample capture cartridge 100 and efficient mixing of the fluid (e.g., the fluid containing the sample with the silica 120 contained in the porous bowl 130). In some embodiments, angled canister sample ports 142 may advantageously promote helical or spiral fluid flow through the canister cavity 144 and improve turbulent flow and/or missing of the sample fluid with the silica 120.

Some embodiments of the cartridge desiccant canister 140 may include a cartridge desiccant canister 140 to prevent moisture transfer to the porous bowl 130. The canister cavity 144 of the cartridge desiccant canister 140 may have a depth of about 3.9 mm. In some embodiments the canister cavity 144 of the cartridge desiccant canister 140 has a depth less than about 12 mm, less than about 11 mm, less than about 10 mm, less than about 9 mm, less than about 8 mm, less than about 7 mm, less than about 6 mm, less than about 5 mm, less than about 4 mm, less than about 3 mm, less than about 2 mm, less than about 1 mm, or any other depth that inhibits or minimizes moisture transfer to the porous bowl 130.

In some embodiments, such as shown in FIG. 6C, nothing is contained in the canister cavity 144 (e.g., it is empty space). The absence of any material in the canister cavity 144 may advantageously promote direct transfer of fluid flow from the canister sample ports 142 to the porous bowl 130, through the bowl base 134 and into the silica 120 contained within the porous bowl 130. That is, an empty canister cavity 144 may allow better fluid flow and mixing to occur in the silica 120 because the fluid flow leaving the canister sample ports 142 is not impeded by a material. However, an additional layer of material to absorb excess moisture (e.g., when analyzing particularly moist samples) may be desirable. In some embodiments, an absorbent material is placed in the canister cavity 144 (e.g., cotton or other fibers in a loose agglomeration).

As shown in FIGS. 1C, and 2A-2B, the cartridge desiccant canister 140 may contain a material to condition a sample-containing fluid before it exits the canister sample ports 142 and enters the porous bowl 130 to react with the functionalized silica 120. In some embodiments, the cartridge desiccant canister 140 contains a quantity of desiccant 150. In some embodiments, the cartridge desiccant canister 140 contains an absorbent disk.

In some embodiments the cartridge desiccant canister 140 contains a volume of desiccant 150 that may be measured in desiccant particles. In some embodiments, the cartridge desiccant canister 140 contains about 20-40 desiccant particles. In some embodiments, the cartridge desiccant canister 140 contains between about 5-200 desiccant particles, between about 10-270 desiccant particles, between about 15-240 desiccant particles, between about 20-210 desiccant particles, between about 25-180 desiccant particles, between about 30-150 desiccant particles, between about 35-120 desiccant particles, between about 40-190 desiccant particles, between about 45-160 desiccant particles, between about 50-130 desiccant particles, between about 55-100 desiccant particles, between about 60-70 desiccant particles, or any other number of desiccant particles that advantageously conditions a fluid sample prior to its interaction with the silica 120 contained within the porous bowl 130.

In some embodiments the cartridge desiccant canister 140 contains a quantity of desiccant 150 that may be measured in mass, e.g., milligrams. In some embodiments, the cartridge desiccant canister 140 contains a mass of desiccant 150 in the range of between about 50-1800 mg, between about 60-1750 mg, between about 70-1700 mg, between about 80-1650 mg, between about 90-1600 mg, between about 100-1550 mg, between about 110-1500 mg, between about 120-1450 mg, between about 130-1400 mg, between about 140-1350 mg, between about 150-1300 mg, between about 160-1250 mg, between about 170-1200 mg, between about 180-1150 mg, between about 190-1100 mg, between about 200-1050 mg, between about 210-1000 mg, between about 220-950 mg, between about 230-900 mg, between about 240-850 mg, between about 250-800 mg, between about 260-750 mg, between about 270-700 mg, between about 280-650 mg, between about 290-600 mg, between about 300-550 mg, between about 310-500 mg, between about 320-450 mg, between about 330-400 mg, or between about 340-350 mg. In some embodiments, the cartridge desiccant canister 140 contains a mass of desiccant 150 in the range of between about 160-180 mg, between about 540-560 mg, or any other mass of desiccant 150 that advantageously conditions a fluid sample prior to its interaction with the silica 120 contained within the porous bowl 130.

In some embodiments, the cartridge desiccant canister 140 may contain at least one absorbent disk in addition to or in place of the desiccant 150. The absorbent disk may be a cotton pad. In some embodiments, an absorbent disk is placed above the desiccant 150 (e.g., between the desiccant 150 and the canister sample ports 142). In some embodiments, an absorbent disk is placed below the desiccant 150 (e.g., between the desiccant 150 and the cartridge desiccant retainer 160). In still other embodiments, a first absorbent disk is placed above the desiccant 150 (e.g., between the desiccant 150 and the canister sample ports 142) and a second absorbent disc is placed below the desiccant 150 (e.g., between the desiccant 150 and the cartridge desiccant retainer 160). Any materials held within the cartridge desiccant canister 140 may be held in place by a cartridge desiccant retainer 160.

FIGS. 7A-7C illustrate various views of an embodiment of a cartridge desiccant retainer 160. FIG. 7A shows a top view of an embodiment of a cartridge desiccant retainer 160. FIG. 7B shows a bottom view of an embodiment of a cartridge desiccant retainer 160. FIG. 7C shows a side cut-away view of the cartridge desiccant retainer 160 of FIG. 7A, taken along line E-E. The cartridge desiccant retainer 160 generally has a diameter, a thickness, and a plurality of desiccant retainer ports 164. In some embodiments, the cartridge desiccant retainer 160 also includes a desiccant retainer bevel 166 and/or a desiccant retainer notch 162.

The diameter of the cartridge desiccant retainer 160 may be just smaller than an inner diameter of the cartridge desiccant canister 140. In some embodiments, the diameter of the cartridge desiccant retainer 160 is between about 8-9 mm. In other embodiments, the diameter of the cartridge desiccant retainer 160 is between about 5-30 mm, between about 5.5-28 mm, between about 6-26 mm, between about 6.5-24 mm, between about 7-22 mm, between about 7.5-20 mm, between about 8-18 mm, between about 8.5-16 mm, between about 9-14 mm, between about 9.5-12 mm, or any other diameter that advantageously facilitates use and collection of samples as disclosed herein.

In some embodiments, the thickness of the cartridge desiccant retainer 160 is about 1 mm. In other embodiments, the thickness of the cartridge desiccant retainer 160 is between about 0.2-3 mm thick, between about 0.3-2.8 mm thick, between about 0.4-2.6 mm thick, between about 0.5-2.4 mm thick, between about 0.6-2.2 mm thick, between about 0.7-2 mm thick, between about 0.8-1.8 mm thick, between about 0.9-1.6 mm thick, between about 1-1.4 mm thick, between about 1.1-1.2 mm thick, or any other thickness that advantageously facilitates use and collection of samples as disclosed herein.

In some embodiments, the cartridge desiccant retainer 160 may be snap fit into the cartridge desiccant canister 140. As can be seen with reference to FIG. 6C, the cartridge desiccant canister 140 may include a raised ridge on its inner surface to hold the cartridge desiccant retainer 160 in place. The desiccant retainer bevel 166 may facilitate the cartridge desiccant retainer 160 slipping unidirectionally past the raised ridge on the inner surface of the cartridge desiccant canister 140. In other embodiments, the cartridge desiccant retainer 160 may be threaded into the cartridge desiccant canister 140. In yet other embodiments, any other type of fixation may be used to hold the cartridge desiccant retainer 160 inside the cartridge desiccant canister 140, e.g., glue, epoxy, friction, welding, bonding, etc.

As can be seen with reference to FIG. 7A-7B, the cartridge desiccant retainer 160 may have 12 individual desiccant retainer notches 162. In some embodiments, the cartridge desiccant retainer 160 may have different numbers of desiccant retainer ports 164. For example, the cartridge desiccant canister 140 may have one desiccant retainer port 164. The cartridge desiccant canister 140 may have less than about 2 desiccant retainer ports 164, less than about 4 desiccant retainer ports 164, less than about 6 desiccant retainer ports 164, less than about 8 desiccant retainer ports 164, less than about 10 desiccant retainer ports 164, less than about 15 desiccant retainer ports 164, less than about 20 desiccant retainer ports 164, less than about 25 desiccant retainer ports 164, less than about 30 desiccant retainer ports 164, less than about 35 desiccant retainer ports 164, less than about 40 desiccant retainer ports 164, less than about 45 desiccant retainer ports 164, less than about 50 desiccant retainer ports 164, or any other number of desiccant retainer ports 164 that promotes fluid flow through the sample capture cartridge 100 and efficient mixing of the fluid (e.g., the fluid containing the sample with the silica 120 contained in the porous bowl 130).

With continued reference to FIGS. 7A and 7B, the desiccant retainer ports 164 may be round. However, the desiccant retainer ports 164 may have other shapes. In some embodiments, the desiccant retainer ports 164 are triangular, rectangular, pentagonal, or hexagonal. Any shape of desiccant retainer ports 164 may be used that advantageously promotes fluid flow through the sample capture cartridge 100 and efficient mixing of the fluid (e.g., the fluid containing the sample with the silica 120 contained in the porous bowl 130). In some embodiments, connected shapes are used as desiccant retainer ports 164, e.g., "plus" (e.g., "+") shaped holes, linear shaped holes (e.g., "−"), etc. In some embodiments, the desiccant retainer ports 164 are distributed evenly across the cartridge desiccant retainer 160. In some embodiments, the desiccant retainer ports 164 are oriented more toward the center of the cartridge desiccant retainer 160 (e.g., increase in concentration closer to the center of the cartridge desiccant retainer 160).

As can be seen in FIG. 7C, the desiccant retainer ports 164 may be oriented substantially vertically through the cartridge desiccant retainer 160. That is to say that the desiccant retainer ports 164 may extend through the cartridge desiccant retainer 160 at approximately a right angle to the either the top surface of the cartridge desiccant retainer 160 or the bottom surface of the cartridge desiccant retainer 160. In some embodiments, the desiccant retainer ports 164 extend through the cartridge desiccant retainer 160 at an angle. In some embodiments the desiccant retainer ports 164 extend through the cartridge desiccant retainer 160 at an angle of less than about 2 degrees off perpendicular, less than about 4 degrees off perpendicular, less than about 6 degrees off perpendicular, less than about 8 degrees off perpendicular, less than about 10 degrees off perpendicular, less than about 15 degrees off perpendicular, less than about 20 degrees off perpendicular, less than about 25 degrees off perpendicular, less than about 30 degrees off perpendicular, less than about 35 degrees off perpendicular, less than about 40 degrees of perpendicular, less than about 45 degrees off perpendicular, or any other angle that advantageously promotes fluid flow through the sample capture cartridge 100 and efficient mixing of the fluid (e.g., the fluid containing the sample with the silica 120 contained in the porous bowl 130). In some embodiments, angled desiccant retainer ports 164 may advantageously promote helical or spiral fluid flow through the canister cavity 144 and improve turbulent flow and/or missing of the sample fluid with the silica 120. In some embodiments, the canister cavity 144 may include a number of baffles, fins, vanes, wings, or other such structures on (e.g., attached to) an interior surface of the canister cavity 144 to promote turbulent, helical, spiral, or other mixing flow patterns. For example, the canister cavity 144 may have 4 baffles. In some embodiments, the canister cavity 144 includes between about 1 and 16 baffles, between about 2 and 14 baffles, between about 3 and 12 baffles, between about 4 and 10 baffles, between about 5 and 8 baffles, or any other number of baffles that advantageously facilitates turbulent, helical, spiral, or other mixing patterns.

With reference to both FIG. 7A and FIG. 6A, desiccant retainer ports 164 in the cartridge desiccant retainer 160 are arranged in substantially the same pattern as the canister sample ports 142 in the cartridge desiccant canister 140 (e.g., the cartridge desiccant retainer 160 has the same number of desiccant retainer ports 164 as the cartridge desiccant canister 140 has canister sample ports 142). The cartridge desiccant retainer 160 may be installed into the cartridge desiccant canister 140 so that the desiccant retainer ports 164 of the cartridge desiccant retainer 160 are intentionally substantially aligned (e.g., aligned within 5 degrees) with the canister sample ports 142 of the cartridge desiccant canister 140. Alignment of the desiccant retainer ports 164 with the canister sample ports 142 may be facilitated by mechanical alignment, e.g., embodiments in which the cartridge desiccant retainer 160 is installed into the cartridge desiccant canister 140 using threads. In some embodiments, the cartridge desiccant retainer 160 may be installed into the cartridge desiccant canister 140 so that the desiccant retainer ports 164 of the cartridge desiccant retainer 160 are intentionally misaligned (e.g., more than 10 degrees off) with the canister sample ports 142 of the cartridge desiccant canister 140. Misalignment of the desiccant retainer ports 164 of the cartridge desiccant retainer 160 and the canister sample ports 142 of the cartridge desiccant canister 140 may advantageously improve turbulent mixing/flow of the sample-containing fluid and/or more complete sample conditioning due to increased contact of the sample-containing fluid with one or more sample-conditioning substances (e.g., desiccant and/or absorbent pad(s)) within the cartridge desiccant canister 140.

In some embodiments, the cartridge desiccant retainer 160 has a different number of desiccant retainer ports 164 than the cartridge desiccant canister 140 has canister sample ports 142. In some embodiments, the desiccant retainer ports 164 of the cartridge desiccant retainer 160 are arranged in a different pattern than the canister sample ports 142 of the cartridge desiccant canister 140. In some embodiments, the desiccant retainer ports 164 of the cartridge desiccant retainer 160 have a different shape(s) than the canister sample ports 142 of the cartridge desiccant canister 140 (e.g., the desiccant retainer port 164 may be a single "+" shaped hole, while the cartridge desiccant canister 140 contains multiple circular canister sample ports 142). Some or all of these features may advantageously contribute to a turbulent flow pattern through part or all of the sample capture cartridge 100. One of ordinary skill in the art will readily understand that various combinations of features, such as described herein, may be used to achieve a desired fluid flow path and mixing profile.

Turning to FIG. 1C, the cartridge lens cap 110 may be formed separately and fit onto the cartridge desiccant canister 140. In some embodiments, the cartridge lens cap 110 is removably attached/attachable to the cartridge desiccant canister 140. For example, the cartridge lens cap 110 may be attached to the cartridge desiccant canister 140 using threads, friction, clips, detents, springs, j-hooks, etc. In other embodiments, the cartridge lens cap 110 is fixedly attached/attachable to the cartridge desiccant canister 140. For example, the cartridge lens cap 110 may be attached to the cartridge desiccant canister 140 using epoxies, glues, welding (e.g., friction welding, and/or other types of welding), cements, locking threads, clips, co-melting plastics, etc.

In some embodiments, the cartridge desiccant canister 140 is formed out of a softer material (e.g., polymer or plastic) to facilitate the cartridge lens cap 110 slipping over the top of the cartridge desiccant canister 140. In some embodiments, the inner wall of the cartridge lens cap 110 and the outer wall of the upper portion of the cartridge desiccant canister 140 have an angle (are slightly sloped or conical) to facilitate simple and quick fitment of the cartridge lens cap 110 to the cartridge desiccant canister 140. In some embodiments, the outer wall of the cartridge desiccant canister 140 has an angle of about 92 degrees to the horizontal. In some embodiments, the outer wall of the cartridge desiccant canister 140 has an angle of less than about 100 degrees, less than about 99 degrees, less than about 98 degrees, less than about 98 degrees, less than about 97 degrees, less than about 96 degrees, less than about 95 degrees, less than about 94 degrees, less than about 93 degrees, less than about 92 degrees, less than about 91 degrees, or any other angle that facilitate application and/or removal of the cartridge lens cap 110 from the sample capture cartridge 100.

Blended Bowl

Turning again to FIGS. 1C, 2A-2B, and 5A-5F, in some embodiments, the porous bowl 130 may be a bowl made of a porous plastic material that permits air flow therethrough, such as, but not limited to, a porous polyethylene, porous polypropylene, porous polyvinylidene fluoride, porous polytetrafluoroethylene, porous ethyl vinyl acetate, porous polycarbondates, porous nylons, porous polyurethanes, porous polyethersulfones. In some embodiments, the porous bowl 130 may be a bowl made of a porous polymer fiber material that permits air flow therethrough, such as, but not limited to, polyethylene/polyester polymer fibers (e.g., bicomponent polyethylene sheath with polyester core fibers (PE/PET)), and/or polyester/polyester polymer fibers (e.g., bicomponent polyester sheath and polyester core fibers (PET/PET)). In some embodiments, the porous bowl 130 is constructed out of a hydrophobic material.

As shown in FIG. 1C, the porous bowl 130 may contain a quantity of a material, e.g., silica beads 120. The silica 120 itself may be unreactive to the sample, but the silica 120 may be functionalized with a reactive moiety, receptor, reactor, etc. The functionalized silica 120 may then absorb or react with an analyte of interest in a sample passed through the porous bowl 130 of the sample capture cartridge 100.

In embodiments in which the porous bowl 130 contains a quantity of a functionalized material (e.g., functionalized silica particles) used to capture an analyte of interest from a fluid sample, mixing may be particularly important (e.g., mixing of the sample with and through the silica 120 contained within the porous bowl 130). Mixing is one reason, among many potential reasons, that turbulent flow through the sample capture cartridge 100 may be desirable. For example, without proper mixing, there may be "hot spots" of analyte accumulation within the silica 120 contained within the porous bowl 130. That is to say, without sufficient mixing, the analyte of interest will react only with the functionalized silica 120 that is reasonably close to the fluid sample's path of least resistance through the sample capture cartridge 100. Sufficient mixing may allow an even reaction between the analyte of interest and the functionalized silica 120 contained within the porous bowl 130. When the reaction between the analyte of interest contained in the fluid sample and the functionalized silica 120 is even, the sample may advantageously be analyzed more accurately. For example, in embodiments in which the reaction ultimately causes a change in color of the silica 120 contained within the porous bowl 130, sufficient mixing may produce an even medium color throughout the silica 120, but insufficient mixing may produce spots of deep or dark color in some, higher flow, locations in the silica 120 and little to no color in other, lower flow, locations, in the silica 120.

The reaction of the analyte with the functionalized silica 120 may produce a measurable change in a parameter of the silica 120. In some embodiments the measurable change is a change in a color of the functionalized silica 120 (e.g., the functionalized silica 120 may change color, may deepen in hue, may change in intensity, etc.). In some embodiments the measurable change is a change in temperature. In some embodiments, the measurable change is a change in volume. Any other measurable change may be used.

In some embodiments, no change is experienced or observed directly after the analyte of interest in the sample is passed through the sample capture cartridge 100. In some embodiments, after the analyte of interest has been captured or separated from the rest of the sample, another substance, an interactant subsystem, such as a developer solution, may be added to the system to bring about or induce the measurable change. The interactant subsystem may be, or include sodium nitroprusside, dinitrophenylhydrazine, sodium dichromate, pararosaniline, bromophenol blue, dischloroisocyanourate, sodium salicylate, sodium dichromate, crystal violet, benzyl mercaptan, or combinations thereof.

In some embodiments, the silica particles (or particles of another base material or substrate such as those mentioned above) may be functionalized with an interactant that supports a single-step reaction which produces a measurable color change without the need to introduce a developer solution. In single-step cartridges for measuring acetone, the interactant may include a complex including one or more metal ions and one or more primary amine molecules bound to the metal ions. The primary amine molecules may be amino acid molecules with a primary amine side chain (e.g. lysine, arginine), and the carboxylic acid group of the amino acid molecules may be bound to the metal ions. The complex including the metal ions and primary amine molecules may be further immobilized to a base material, such as silica beads. Other interactant compositions that support single-step reactions are known in the art.

In some embodiments, the porous bowl 130 is manufactured to integrally and/or substantially homogeneously contain the functionalized base material (e.g., functionalized silica particles) to create a blended bowl or structure. In such embodiments, the porous bowl 130 may retain its "bowl" shape. Or, the porous bowl 130 may be formed as a disc, puck or other shape (e.g., as it no longer needs to contain a volume of silica 120 within the porous bowl 130).

The blended bowl may be formed of a porous reactive media comprising a polymeric infrastructure and a resin incorporating a reactive chemistry configured to react with or bind to the analyte of interest in the fluid sample (e.g., breath sample) being evaluated. The blended bowl may be synthesized utilizing a blended resin in a substantially round or spherical configuration of the polymeric material (including but not limited to polyethylene) and functionalized reactive beads (e.g., functionalized silica 120 beads, as disclosed herein). In some embodiments, the porous bowl may be formed out of a functionalized fused silica wool.

A blended bowl or structure may advantageously be formed out of resin particles and functionalized or reactive particles in a mixture that is about 50% resin particles. In some embodiments, a blended bowl may be formed out of resin particles and functionalized or reactive particles in a mixture that is less than about 50% functionalized or reactive particles, less than about 45% functionalized or reactive particles, less than about 40% functionalized or reactive particles, less than about 35% functionalized or reactive particles, less than about 30% functionalized or reactive particles, less than about 25% functionalized or reactive particles, less than about 20% functionalized or reactive particles, less than about 15% functionalized or reactive particles, less than about 10% functionalized or reactive particles, less than about 5% functionalized or reactive particles, less than about, or any other percentage that advantageously facilitates sufficient capture of an analyte of interest by the functionalized or reactive particles held by the blended bowl.

In some embodiments, a blended bowl incorporates a quantity of desiccant in addition to the quantity of functionalized or reactive particles. In some embodiments, a blended bowl may be formed out of resin particles and functionalized or reactive particles as discussed here, with a quantity of desiccant in a mixture that is less than about 50% desiccant, less than about 45% desiccant, less than about 40% desiccant, less than about 35% desiccant, less than about 30% desiccant, less than about 25% desiccant, less than about 20% desiccant, less than about 15% desiccant, less than about 10% desiccant, less than about 5% desiccant, less than about 2.5% desiccant, or any other percentage that advantageously facilitates removal of excess moisture from a fluid sample.

Resin particles and functionalized or reactive particles may be formed into a blended bowl, disc, or frit using a sintering process. The sintering process may involve a die tool (e.g., a floating die) to manufacture the blended bowl at temperatures in the range of about 110-400° C., e.g., generally above the true melting point of the polymeric material. Alternative sintering techniques, e.g., known as selective laser sintering (SLS), may be used to form the blended bowl. For example, SLS may use a laser (e.g., operated in continuous mode) at variable ranges of speed and power to obtain the appropriate energy density per unit time in the fabrication of pore sizes and reactant dispersions throughout the blended bowl. Thermal treatment at higher temperatures may allow for aminated reactive beads to assiduously coagulate within the polymeric infrastructure via covalent bonding and grafting at the interface.

In some embodiments, a blended bowl may be inserted into the cartridge lens cap 110. In some embodiments a blended bowl may be mechanically coupled (e.g., directly coupled) to the underside of the lens cap window 112, which may advantageously provide a degree of surface area augmentation.

In some embodiments, the blended bowl or structure is configured such as the porous bowl 130, as disclosed herein. The blended bowl may be installed in the cartridge lens cap 110 such as shown in FIG. 1C, e.g., with the "bowl" facing upwards (e.g., facing the lens cap window 112 of the cartridge lens cap 110). Alternatively, the blended bowl may be installed in the cartridge lens cap 110 opposite that shown in FIG. 1C, e.g., with the "bowl" facing downwards (e.g., the bowl base 134 of the porous bowl 130 facing the lens cap window 112 of the cartridge lens cap 110). For example, the blended bowl may have a bowl-like (e.g., such as shown in FIGS. 5C-5D) configuration such that the outer edges, including but not limited to the bowl wall 132 and the bowl base 134. Such bowl-like configurations may offer an advantageously increased (e.g., a maximum) surface area available for adhesion (e.g., secure adhesion) to the inside surface of the lens cap window 112 of the cartridge lens cap 110. In some embodiments, the cavity depth is influenced by the flow path of the fluid sample during sample collection (e.g., containing an analyte of interest) through the overall sample capture cartridge 100 (e.g., into the cartridge desiccant canister 140, through the cartridge desiccant retainer 160, through the desiccant 150, through the ports in the upper surface of the cartridge desiccant canister 140, through the canister cavity 144, etc.) to the outward surface of the blended bowl.

A blended bowl or structure as discussed herein may advantageously simplify, linearize, shorten, etc. the procedure or process for manufacturing a sample capture cartridge 100 as disclosed herein. For example, a blended bowl may eliminate the need for a reactive/functionalized silica 120 (e.g., silica 120 contained within the porous bowl 130); consequently at least some equipment (e.g., dispensing equipment for the silica 120) may be eliminated or removed from the production line. Furthermore, a production line for producing various embodiments of the sample capture cartridge 100 disclosed herein may, for example, include a cartridge desiccant canister preparation station and a clamping station. Such a cartridge desiccant canister 140 preparation station may include a dispensing mechanism to consistently dispense a volume of desiccant 150 into the porous bowl 130 and a separate clamping station to append the cartridge lens cap 110 to the cartridge desiccant canister 140. A secondary clamping station may be used to mechanically couple the blended bowl with the cartridge lens cap 110 (e.g., to the underside of the lens cap window 112) and subsequently couple the packed cartridge lens cap 110 (e.g., the cartridge lens cap 110 containing the blended bowl) to the cartridge desiccant canister 140 (which may be already pack with desiccant 150, absorbent pads, and/or a cartridge desiccant retainer 160). Such simplification of the production line may advantageously facilitate mass production of sample capture cartridges 100.

A blended bowl or structure, as disclosed herein, may confer additional potential benefits on a sample capture cartridge 100. For example a blended bowl may serve to reduce airflow resistance. In some embodiments, a blended bowl reduces airflow resistance by comparison to a porous bowl 130 containing a quantity of silica 120 more than about 4%. In some embodiments, a blended bowl reduces airflow resistance by more than about 1%, more than about 2%, more than about 3%, more than about 4%, more than about 5%, more than about 6%, more than about 7%, more than about 8%, more than about 9%, more than about 10%, more than about 12.5%, more than about 15%, more than about 17.5%, more than about 20%, or any other reduction in airflow resistance that may beneficially facilitate sample collection and analysis as disclosed herein.

In some embodiments, a blended bowl or structure facilitates analysis of the change resulting from interaction between the functionalized/reactive particles and the analyte of interest. For example, the blended bowl may be placed directly under the lens cap window 112, thereby reducing the distance between any analysis system (e.g., a photoanalysis system) and the collected analyte of interest. For example, the blended bowl prevents any movement of loose silica 120 contained within the bowl (e.g., silica 120 contained within the porous bowl 130). As no silica 120 may move within the porous bowl 130, turbulent mixing of the fluid sample with the silica 120 may be less critical. Additionally, when a blended bowl is used, movement of the sample capture cartridge 100 between sample collection and sample analysis may be less important (e.g., movement will, generally, not alter the position of the reactive/functionalized particles). As such, colorimetric changes may be analyzed more accurately when using a blended bowl.

In some embodiments, two separate disks, bowls, pucks, or other solid structures may be created and incorporated into the cartridge, one which contains the reactive material, and one which contains a desiccant. For example, a reactive disc or puck may be created as described above (e.g., by blending functionalized silica or other particles with resin particles), and a non-reactive desiccant disk or puck may be created by blending desiccant particles with resin particles using substantially the same process. These two solid, porous structures, each of which may have a cylindrical or puck-like configuration, may then be incorporated into the cartridge, with the desiccant structure positioned upstream from the reactive structure in the breath flow path (to remove moisture from the breath sample before it reaches the reactive structure). The two structures may optionally be fused or molded together to create a single porous piece (which may have a cylindrical configuration) that contains a desiccant layer and a reactive layer, in which case this multi-layer piece would be inserted into the cartridge with the desiccant layer positioned upstream from the reactive layer.

Mechanical Sample Collection Whistle

FIGS. 8A-8B illustrate an embodiment of a sample capture cartridge 100, disclosed herein, being placed (e.g., snapped into) in an embodiment of a sample collection whistle 200 (e.g., a device for collecting a sample, a reusable handheld analyte sample collection device, an analyte collector, a handheld breath collector, etc.) prior to collection of a sample. While the sample collection whistle 200 is discussed in additional detail herein, FIG. 8A shows the sample capture cartridge 100 being loaded into the sample collection whistle 200 from a front-top three-quarters view. In much the same way, FIG. 8B shows the sample capture cartridge 100 being loaded into the sample collection whistle 200 from a rear-top three-quarters view.

Figure 9A:
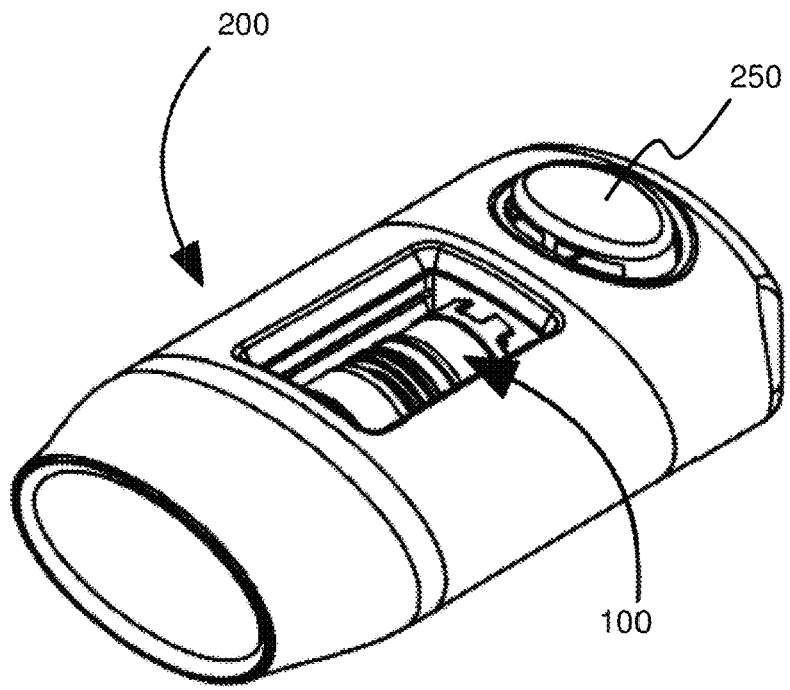
Figure 9B:
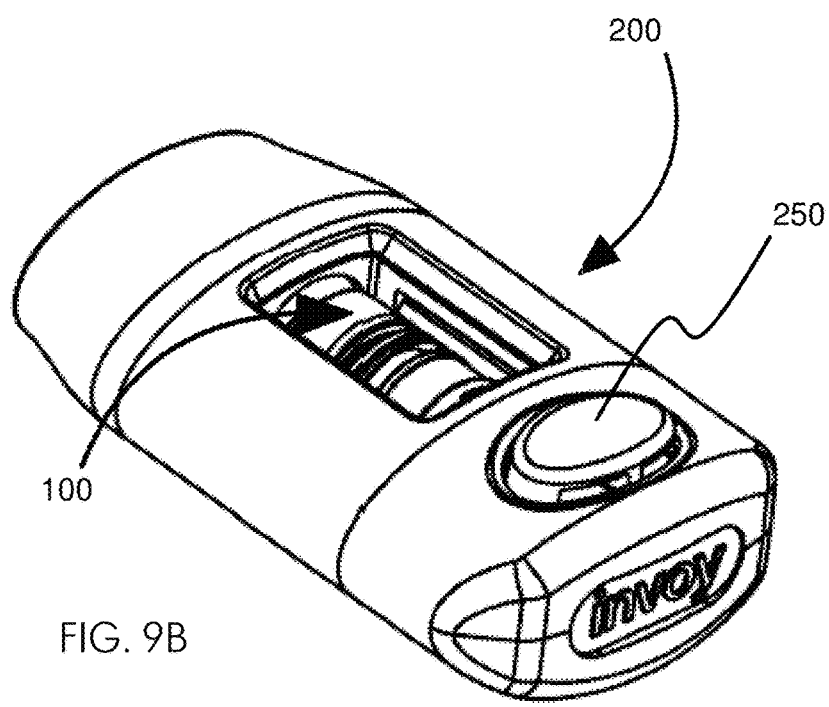

FIGS. 9A-9B illustrate an embodiment of a sample capture cartridge 100, disclosed herein, after being placed (e.g., snapped into) an embodiment of a sample collection whistle 200 (as shown in FIGS. 9A-9B, a sample may or may not have already been collected).

FIGS. 8C-8F illustrate the sample collection whistle 200 of FIGS. 8A-8B, prior to loading of a sample capture cartridge 100. FIG. 8C shows the sample collection whistle 200 from the top. FIG. 8D shows the sample collection whistle 200 from the side (e.g., the left side). FIG. 8E shows the sample collection whistle 200 from the rear. FIG. 8F shows the sample collection whistle 200 from the front. As can be seen, the sample collection whistle 200 generally has three main body pieces, including a whistle mouthpiece 210, a whistle core 220, and a whistle back 240. Some embodiments of the sample collection whistles disclosed herein do not include any sensors or other electronics. For example, the sample collection whistles may not include any sensors or other electronics for analyzing a sample collection cartridge or other sample collection module to measure or analyze the concentration of an analyte.

Some embodiments of the sample collection whistles disclosed herein are portable, small, or hand-held devices. In some embodiments, the sample collection whistle is less than about 10 cm long. In some embodiments, the sample collection whistle is shorter than about 20 cm, shorter than about 19.5 cm, shorter than about 19 cm, shorter than about 18.5 cm, shorter than about 18 cm, shorter than about 17.5 cm, shorter than about 17 cm, shorter than about 16.5 cm, shorter than about 16 cm, shorter than about 15.5 cm, shorter than about 15 cm, shorter than about 14.5 cm, shorter than about 14 cm, shorter than about 13.5 cm, shorter than about 13 cm, shorter than about 12.5 cm, shorter than about 12 cm, shorter than about 11.5 cm, shorter than about 11 cm, shorter than about 10.5 cm, shorter than about 10 cm, shorter than about 9.5 cm, shorter than about 9 cm, shorter than about 8.5 cm, shorter than about 8 cm, shorter than about 7.5 cm, shorter than about 7 cm, shorter than about 6.5 cm, shorter than about 6 cm, shorter than about 5.5 cm, shorter than about 5 cm, shorter than about 4.5 cm, shorter than about 4 cm, shorter than about 3.5 cm, shorter than about 3 cm, shorter than about 2.5 cm, or shorter than about 2 cm. In some embodiments, the sample collection whistle weighs less than about 300 grams, less than about 280 grams, less than about 260 grams, less than about 240 grams, less than about 220 grams, less than about 200 grams, less than about 180 grams, less than about 160 grams, less than about 140 grams, less than about 120 grams, less than about 100 grams, less than about 80 grams, less than about 60 grams, or less than about 40 grams.

In some embodiments, the sample collection whistle 200 includes a whistle sample inlet 212. A whistle sample inlet 212 may be seen clearly in FIG. 8F. As discussed in additional detail herein, when a sample is being taken, the fluid sample (e.g., breath) is inserted (e.g., blown) into the sample collection whistle 200 through the whistle sample inlet 212 of the whistle mouthpiece 210 for collection by the sample capture cartridge 100.

In some embodiments, the sample collection whistle 200 (or any other sample collection whistle disclosed herein) is a hand-held collection device, e.g., it may easily fit in and be used while in a user's hand. In some embodiments, the sample collection whistle 200 is about 3 inches long. In some embodiments, the sample collection whistle 200 is between about 1-6 inches long, between about 1.5-5.5 inches long, between about 2-5 inches long, between about 2.5-4.5 inches long, between about 3-4 inches long, or any other length that advantageously accepts and holds a sample capture cartridge 100 as disclosed herein. In some embodiments, the sample collection whistle 200 is about 2.5 inches wide. In some embodiments, the sample collection whistle 200 is between about 1-5 inches wide, between about 1.5-4.5 inches wide, between about 2-4 inches wide, between about 2.5-3.5 inches wide, about 3 inches wide, or any other width that advantageously accepts and holds a sample capture cartridge 100 as disclosed herein. In some embodiments, the sample collection whistle 200 is about 1 inch thick. In some embodiments, the sample collection whistle 200 is between about 0.25-3 inches thick, between about 0.5-2.75 inches thick, between about 0.75-2.5 inches thick, between about 1-2.25 inches thick, between about 1.25-2 inches thick, between about 1.5-1.75 inches thick, or any other thickness that advantageously accepts and holds a sample capture cartridge 100 as disclosed herein.

In some embodiments, the sample collection whistle 200 is a purely mechanical device that contains no electrical components. For example, the sample collection whistle 200 may not contain any circuitry, sensors, etc. for analyzing a sample capture cartridge 100, a sample or analyte of interest contained within a sample capture cartridge 100 or for otherwise measuring any aspect of a sample. In some embodiments, the sample collection whistle 200 may include various electrical components, sensors, processors, actuators, circuitry, etc. In some embodiments, the sample collection whistle 200 may include electronics (sensors, etc.) for controlling a state of an aspect of the sample collection whistle 200 (e.g., a valve or other element, such as the whistle button 250, that may control, partially or fully, or influence flow of a fluid sample through a sample collection cartridge (e.g., during exhalation), but lacks circuitry for analyzing the sample collection cartridge or otherwise measuring a concentration of the analyte of interest. In some embodiments, the sample collection whistle 200 contains various electrical components including, without limitation, various sensors for analyzing a sample capture cartridge 100 or a sample or analyte of interest contained within or associated with a sample capture cartridge 100. For example, the sample collection whistle 200 may contain various processors and circuitry that automatically segment a sample. For example the sample collection whistle 200 may contain various sensors (e.g., optical sensors, or otherwise) that analyze the silica 120 (or blended bowl) contained beneath the cartridge lens cap 110 of the sample capture cartridge 100.

In some embodiments, the whistle core 220 includes a cartridge insertion window 224 and a cartridge ejection window 222. Generally, the cartridge insertion window 224 will have dimensions (e.g., a height and a width) that allow insertion of a sample capture cartridge 100 through the cartridge insertion window 224 and into the body of the whistle core 220 of the sample collection whistle 200. The cartridge ejection window 222 may have dimensions that do not allow passage of a sample capture cartridge 100 through the cartridge ejection window 222. In some embodiments, the cartridge ejection window 222 is used to facilitate ejection of a sample capture cartridge 100 after sample collection has been completed. For example, after sample collection, a user may insert at least a portion of their finger or at least a portion of a tool into the cartridge ejection window 222 to push the sample capture cartridge 100 out of the cartridge insertion window 224. FIG. 8D shows the placement of a cartridge insertion window 224 on the top of the whistle core 220 and the cartridge ejection window 222 on the bottom of the whistle core 220. Alternatively or in addition to the cartridge ejection window 222, the whistle core 220 may include a sample capture cartridge 100 ejection button that may be pressed to more conveniently eject the sample capture cartridge 100 from within the whistle core 220 of the sample collection whistle 200.

The whistle back 240 may include a whistle button 250. In some embodiments, the whistle button 250 is configured to move the sample capture cartridge 100 within the whistle core 220. In some embodiments, the whistle button 250 is configured to move the sample capture cartridge 100 anteriorly in the whistle core 220 (e.g., towards the whistle sample inlet 212 of the whistle mouthpiece 210). In some embodiments, the whistle button 250 is configured to move the sample capture cartridge 100 posteriorly in the whistle core 220 of the sample collection whistle 200 (e.g., away from the whistle sample inlet 212 of the whistle mouthpiece 210). In still other embodiments, the whistle button 250 is configured to move the sample capture cartridge 100 both anteriorly (e.g., towards the whistle sample inlet 212 of the whistle mouthpiece 210) and posteriorly (e.g., away from the whistle sample inlet 212 of the whistle mouthpiece 210) in the whistle core 220 of the sample collection whistle 200. Various embodiments of whistle button 250 are disclosed herein.

FIGS. 9C-9F illustrate the sample collection whistle 200 shown in FIGS. 8C-8F following insertion of a sample capture cartridge 100. FIG. 9C-9F illustrate the sample collection whistle 200 after insertion of the sample capture cartridge 100 from the same angles as the sample collection whistle 200 shown in FIGS. 8C-8F.

With reference to FIG. 9C, it can be seen that the cavity containing the sample capture cartridge 100 (e.g., after the sample capture cartridge 100 was placed in through the cartridge insertion window 224) may have dimensions, e.g., height, width, and/or depth, slightly larger than the sample capture cartridge 100. In some embodiments, at least one of the height, width, or depth, is larger than the corresponding dimension of the sample capture cartridge 100 by at least about 101%, at least about 102%, at least about 103%, at least about 104%, at least about 105%, at least about 106%, at least about 107%, at least about 108%, at least about 109%, at least about 110%, at least about lens cap window 112.5%, at least about 115%, at least about 117.5%, at least about 120%, or any other increase in size that advantageously facilitations acceptance and temporary retention of a sample capture cartridge 100 as disclosed herein.

With reference to FIG. 9F, the cartridge desiccant retainer 160 of the sample capture cartridge 100 may be seen through the whistle sample inlet 212 of the whistle mouthpiece 210 of the sample collection whistle 200.

After insertion of a sample capture cartridge 100 through the cartridge insertion window 224 and into the whistle core 220, some space may exist between the sample capture cartridge 100 and any surface of the sample collection whistle 200. As such, a fluid inserted through the whistle sample inlet 212 of the whistle mouthpiece 210 may escape from the sample collection whistle 200, e.g., from the gap between the sample capture cartridge 100 and the sample collection whistle 200. This is due to the principle of fluids following a path of least resistance. Even when the sample capture cartridge 100 is inserted more proximally in the sample collection whistle 200 (e.g., closer to the whistle sample inlet 212), the pressure of the fluid being inserted through the whistle sample inlet 212 may push the sample capture cartridge 100 distally in the whistle core 220 (e.g., towards the whistle back 240), thereby increasing the gap between the sample capture cartridge 100 and the whistle mouthpiece 210 and creating a space through which the fluid sample may escape.

The whistle button 250 may be actuated to force the sample capture cartridge 100 proximally within the whistle core 220 such that the base of the cartridge desiccant canister 140 of the sample capture cartridge 100 may seal or substantially seal against a surface or portion of the sample collection whistle 200 (e.g., a surface of the whistle mouthpiece 210). When the base of the cartridge desiccant canister 140 is forced against the surface, the gap between the sample capture cartridge 100 and the whistle core 220 may be substantially eliminated, thereby changing the path of least resistance to be through the sample capture cartridge 100, e.g., through the whistle sample inlet 212, and into the cartridge desiccant canister 140, through the cartridge desiccant retainer 160, through the desiccant 150, through the canister cavity 144, and through the porous bowl 130 and silica 120 (or the blended bowl) and out of lens cap vents 114 of the cartridge lens cap 110.

When the whistle button 250 is not being actuated, e.g., pushed, the gap between the sample capture cartridge 100 and the whistle core 220 may allow a substantial portion of the fluid sample to escape without passing through the sample capture cartridge 100. In some embodiments, when the whistle button 250 is not actuated, the percentage of the fluid sample that escapes the sample collection whistle 200 without passing through the sample capture cartridge 100 is at least about 50%, at least about 60%, at least about 70%, at least about 80%, at least about 85%, at least about 90%, at least about 91%, at least about 92%, at least about 93%, at least about 94%, at least about 95%, at least about 96%, at least about 97%, at least about 98%, or at least about 99%.

When the whistle button 250 is being actuated, e.g., pushed, the gap between the sample capture cartridge 100 and the whistle core 220 is closed and a substantial portion of the fluid sample is not permitted to escape and is forced through the sample capture cartridge 100. In some embodiments, when the whistle button 250 is actuated, the percentage of the fluid sample that passes through the sample capture cartridge 100 is at least about 50%, at least about 60%, at least about 70%, at least about 80%, at least about 85%, at least about 90%, at least about 91%, at least about 92%, at least about 93%, at least about 94%, at least about 95%, at least about 96%, at least about 97%, at least about 98%, or at least about 99%.

Figure 10D:
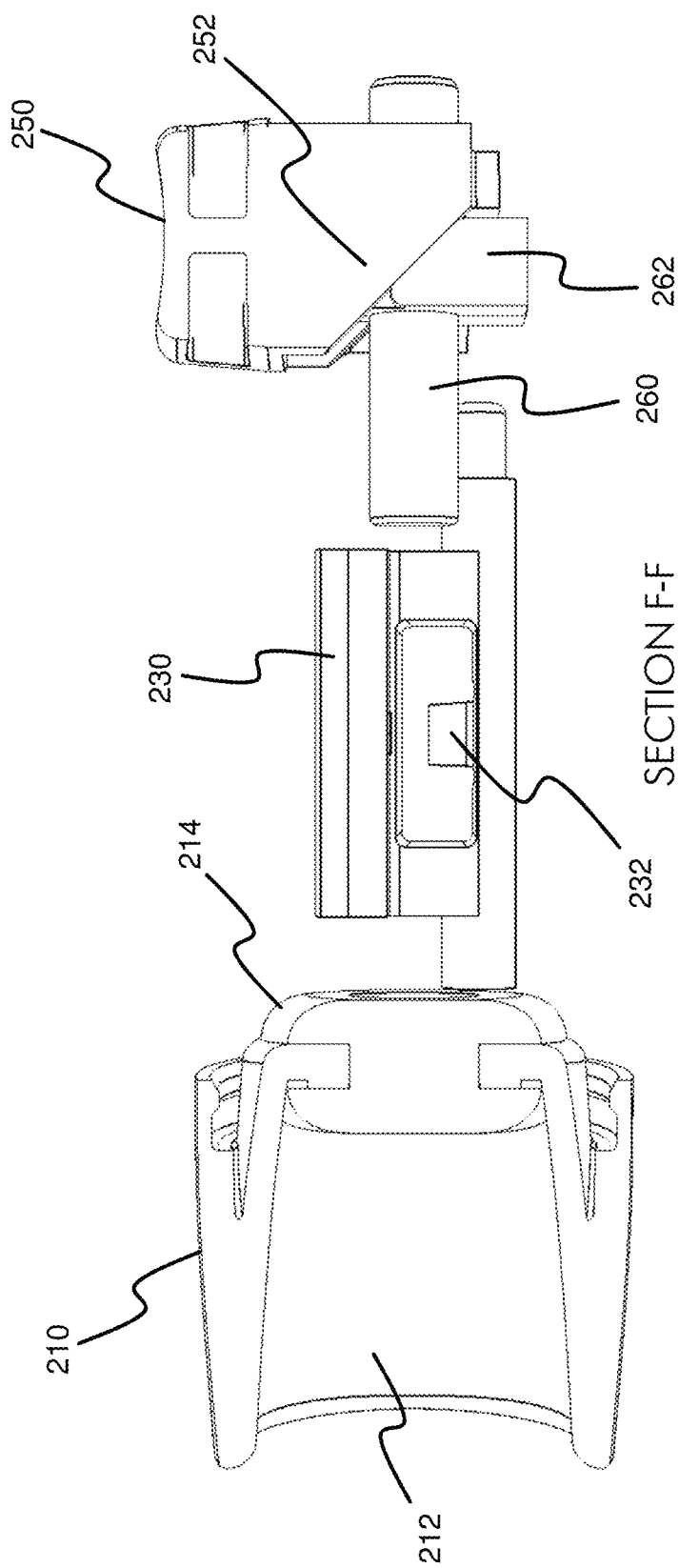

With reference to FIG. 10D, the whistle mouthpiece 210 may include a cartridge sealing grommet 214. For example the whistle mouthpiece 210 may hold a cartridge sealing grommet 214 against which the sample capture cartridge 100 is pushes when the whistle button 250 is actuated. In some embodiments, the cartridge sealing grommet 214 is a lower durometer material, such as a rubber, that is configured to advantageously form a tight seal with the cartridge desiccant canister 140 of the sample capture cartridge 100 (e.g., the cartridge sealing grommet 214 has a diameter that is larger than the diameter of the cartridge desiccant canister 140 of the sample capture cartridge 100 such that the entire perimeter of the lower surface or ring of the cartridge desiccant canister 140 may be effectively pressed into the cartridge sealing grommet 214). In such embodiments, when the whistle button 250 is actuated, the sample capture cartridge 100 is moved proximally in the whistle core 220 toward the whistle mouthpiece 210 such that the cartridge desiccant canister 140 of the sample capture cartridge 100 contacts and seals against the cartridge sealing grommet 214 of the whistle mouthpiece 210. Therefore, the fluid sample flows into the whistle sample inlet 212, through the cartridge sealing grommet 214 (e.g., through a central aperture of the cartridge sealing grommet 214) and into the various internal portions of the sample capture cartridge 100 and out of the lens cap vents 114 of the cartridge lens cap 110. The cartridge sealing grommet 214 of the whistle mouthpiece 210 may advantageously increase the percentage of the fluid sample that passes through the sample capture cartridge 100 (and reduce the percentage of the fluid sample that escapes through gaps or discontinuities in the system). For example, when the cartridge sealing grommet 214 is included in the whistle mouthpiece 210, when the whistle button 250 is actuated, the percentage of the fluid sample that passes through the sample capture cartridge 100 is at least about 90%, at least about 91%, at least about 92%, at least about 93%, at least about 94%, at least about 95%, at least about 96%, at least about 97%, at least about 98%, or at least about 99%.

The ability of the whistle button 250 of the sample collection whistle 200 to dictate how much of the fluid sample escapes the sample capture cartridge 100 and/or is forced through the sample capture cartridge 100 allows segmentation of a fluid sample. For example, a portion of a fluid sample (e.g., an initial portion of the fluid sample) may intentionally be vented by the sample collection whistle 200. Then, upon actuation of the whistle button 250, a later portion of the fluid sample may be forced through the sample capture cartridge 100 and an analyte of interest from that later portion of the fluid sample collected by the sample capture cartridge 100. Such sample segmentation may be advantageously applied to breath samples to separate a breath, e.g., to separate tidal volume from alveolar air. Tidal volume is the portion of a breath that is displaced in normal inhalations and exhalations when no extra effort is applied (e.g., sitting still, at rest, breathing normally without extra depth). Under normal circumstances, the tidal volume comprises a portion of dead-space, mixed air (including a mixture of dead-space and alveolar air), and alveolar air. The dead-space is air from at least one of the trachea, nasal cavity, and mouth. The mixed air includes some breath sourced from the deeper regions of the lung, including, for example, the alveoli, but it also contains some breath sourced from the dead-space. The final segment, alveolar air, is sourced substantially entirely from the deeper segments of the lungs, including the alveoli—this, third and final segment is generally appropriate for analyzing as an alveolar breath sample. Therefore, the whistle button 250 may be used to effectively separate a breath to collect substantially only alveolar air.

FIGS. 10A-10D illustrate various internal components of an embodiment of a sample collection whistle 200. FIG. 10A illustrates a top-biased side view of sample collection whistle 200. The sample collection whistle 200 shown in FIG. 10A is the same as the sample collection whistle 200 shown in FIG. 8C, except that the whistle core 220 is removed, showing the internal components covered by that portion. In addition to the whistle mouthpiece 210 (having a whistle sample inlet 212) and the cartridge sealing grommet 214 (having a whistle button 250), two whistle leaders 230 each having a leader fin 232, and the whistle pusher 260 may be seen. The sample collection whistle 200 shown in FIG. 10B is the same as the sample collection whistle 200 shown in FIG. 10A, except that the whistle back 240 is removed and a sample capture cartridge 100 is shown being held by the whistle leaders 230. The sample collection whistle 200 shown in FIG. 10C is the sample collection whistle 200 shown in FIG. 10B, except from a rear angle. Finally, the sample collection whistle 200 shown in FIG. 10D is a cross-sectional view of the sample collection whistle 200 shown in FIG. 10A, taken along line A-A, except that the whistle back 240 has been removed for easier viewing.

The whistle leaders 230 and their respective leader fin 232 may be held in sockets. On socket may be associated with or attached to (e.g., coupled to, fixed to, or otherwise part of) the whistle back 240 and one socket may be associated with or attached to (e.g., coupled to, fixed to, or otherwise part of) the whistle mouthpiece 210. The whistle leader 230 may be pivotable within the sockets. Each of leader fin 232 serves as a spring to bias the whistle leader 230 inwards. As might be seen most clearly from FIG. 10C, each leader fin 232 extend outwardly (e.g., laterally out) from the rotational axis of the whistle leader 230 and toward the inner wall of the sample collection whistle 200. More specifically, each leader fin 232 is configured to be in close approximation or in contact with an inner surface of the whistle core 220. In this way, when the sample collection whistle 200 is assembled, the leader fins 232 constantly push or bias the whistle leaders 230 inward. The whistle leaders 230 are dimensioned so that a sample capture cartridge 100 may be pushed between them (e.g., they may be shaped like inverted "L"s). When a sample capture cartridge 100 is pushed between the whistle leaders 230 the whistle leaders 230 push away from the center of the cartridge insertion window 224, against the leader fins 232, thereby allowing the sample capture cartridge 100 to pass between the whistle leaders 230. Once the sample capture cartridge 100 passes the whistle leaders 230 (e.g., the widest diameter of the sample capture cartridge 100 passes past the top of the whistle leaders 230), or "snaps" into place, the leader fins 232 push the whistle leaders 230 back out over the sample capture cartridge 100 to hold the sample capture cartridge 100 in place within the whistle core 220. In this way, the sample capture cartridge 100 may be simply and easily held in place during use (e.g., axially aligned with the whistle sample inlet 212 and/or the cartridge sealing grommet 214).

In much the same way, once a sample collection has been completed, the sample capture cartridge 100 may be pushed out of the whistle core 220 by applying pressure to the sample capture cartridge 100 through the cartridge ejection window 222. Upward pressure on the sample capture cartridge 100 pushes the sample capture cartridge 100 up and against the whistle leaders 230, which causes them to rotate outward, against the spring force of the leader fins 232. Upon application of sufficient pressure (which, in most cases may be relatively light) the spring force of the leader fins 232 may be overcome and the sample capture cartridge 100 may snap or pop past the whistle leaders 230 and out of the whistle core 220 of the sample collection whistle 200.

As can be seen in FIGS. 10A and 10D, the whistle pusher 260 may be a substantially cylindrical. The whistle pusher 260 may have a longitudinal axis. In some embodiments, the longitudinal axis of the whistle pusher 260 may substantially align with the axis of the cartridge sealing grommet 214 (e.g., the opening through the cartridge sealing grommet 214). In some embodiments, the longitudinal axis of the whistle pusher 260 may substantially align with the center of the sample capture cartridge 100 (e.g., the longitudinal axis of the sample capture cartridge 100). In some embodiments, the whistle pusher 260 may be aligned with the center of the cartridge lens cap 110 of the sample capture cartridge 100. In other words, the whistle pusher 260 may push on the sample capture cartridge 100 substantially at or near the center of the lens cap window 112 of the cartridge lens cap 110.

In some embodiments, the whistle pusher 260 has a substantially cylindrical shape. In some embodiments, the whistle pusher 260 has a diameter of about 5-6 mm. In some embodiments, the whistle pusher 260 has a diameter in the range of between about 2-35 mm, between about 2.5-30 mm, between about 3-25 mm, between about 3.5-20 mm, between about 4-15 mm, between about 4.5-10 mm, between about 5-8 mm, or any other diameter that advantageously facilitates moving a sample capture cartridge 100 proximally (e.g., towards the mouthpiece) in the sample collection whistle 200. Of course, the whistle pusher 260 may have any of a number of shapes other than cylindrical. For example, the whistle pusher 260 may be triangular, rectangular, pentagonal, or hexagonal. Indeed, any shape of whistle pusher 260 may be used that advantageously facilitates moving a sample capture cartridge 100 proximally (e.g., towards the mouthpiece) in the sample collection whistle 200.

In some embodiments, the whistle pusher 260 has a shape and/or a feature to protect the lens cap window 112 of the cartridge lens cap 110. Because some embodiments of the sample capture cartridge 100 optically analyze a material change through the lens cap window 112 it may be advantageous to protect the lens cap window 112 from scratches, marring, or any other damage that might change the transparency of the lens cap window 112, whether locally or otherwise. In some embodiments, the whistle pusher 260 terminates in a pad that protects the lens cap window 112, e.g., prevents the lens cap window 112 from being scratched or marred. Such a protective pad may be constructed out of felt, fibers, rubber, etc. The protective pad may be any material that has a lower durometer than the lens cap window 112 so that that it does not scratch, mar, or damage the lens cap window 112. In some embodiments, the whistle pusher 260 terminates in a cone or cylinder with an open center. Such a cone or cylinder may be configured to push against the top of the cartridge lens cap 110 without touching the center of the cartridge lens cap 110, e.g., where the lens cap window 112 is located.

With continued reference to FIG. 10D, the whistle pusher 260 may include a pusher ramp 262 and the whistle button 250 may include a corresponding button ramp 252. When the whistle button 250 is depressed (e.g., actuated), it travels into the sample collection whistle 200 in a direction that is substantially perpendicular to the longitudinal axis of the whistle pusher 260. As the whistle button 250 and the button ramp 252 move down, into the sample collection whistle 200, the button ramp 252 causes the pusher ramp 262 to slide along the interface between the button ramp 252 and the pusher ramp 262. As the pusher ramp 262 slides, the whistle pusher 260 is moved forward, e.g., proximally within the sample collection whistle 200. Of course, one of ordinary skill in the art will understand that the ramped interface that includes button ramp 252 and pusher ramp 262 is merely one way of actuating whistle pusher 260 to move a sample capture cartridge 100 (when in place) proximally in the sample collection whistle 200.

Noisemaker Sample Collection Whistle

Some embodiments of the sample collection whistle 200 disclosed herein contain various functionality to alert a user or a device monitoring the sample collection of one or more statuses of the sample collection whistle 200. For example, the sample collection whistle 200 may include functionality to facilitate segmentation of a fluid sample.

FIG. 11A shows an embodiment of a sample collection whistle 200 that is configured to make a noise when fluid passes through the sample collection whistle 200. FIG. 11B shows the sample collection whistle 200 of FIG. 11A from the front, and shows one embodiment of a noise maker that may be included in the sample collection whistle 200. FIG. 11C shows the embodiment of the noisemaker of FIG. 11B. As shown in FIG. 11C, one possible noise maker includes a stationary vane 270 attached to a rotating vane 272 that rotates when a fluid is pushed through at a sufficient rate. However, one of ordinary skill in the art will readily grasp that many different types of noise makers may be used.

In some embodiments, the sample collection whistle 200 includes a noise maker that makes a noise when fluid is pushed through (e.g., blown through) the whistle sample inlet 212 of the whistle mouthpiece 210 at a sufficient rate, regardless of whether a sample capture cartridge 100 is in place or not. In some embodiments, the noise made by the noise maker is a tone or a whistle. In some embodiments, the sample collection whistle 200 includes a noise maker that: makes a first noise when fluid is pushed through the whistle sample inlet 212 of the whistle mouthpiece 210 at a sufficient rate and a sample capture cartridge 100 is present, but the whistle button 250 is not actuated; and makes a second noise when fluid is pushed through the whistle sample inlet 212 of the whistle mouthpiece 210 at a sufficient rate and a sample capture cartridge 100 is present and the whistle button 250 is actuated. In some embodiments, the sample collection whistle 200 includes a noise maker that: makes a first noise when fluid is pushed through the whistle sample inlet 212 of the whistle mouthpiece 210 at a sufficient rate, but a sample capture cartridge 100 is not present; makes a second noise when fluid is pushed through the whistle sample inlet 212 of the whistle mouthpiece 210 at a sufficient rate and a sample capture cartridge 100 is present, but the whistle button 250 is not actuated; and makes a third noise when fluid is pushed through the whistle sample inlet 212 of the whistle mouthpiece 210 at a sufficient rate and a sample capture cartridge 100 is present and the whistle button 250 is actuated. In some embodiments, the sample collection whistle 200 includes a noise maker that: makes a first noise when fluid is pushed through the whistle sample inlet 212 of the whistle mouthpiece 210 at a sufficient rate, but the whistle button 250 is not actuated; and makes both the first noise and a second noise (e.g., a second noise different or distinct from the first noise) when fluid is pushed through the whistle sample inlet 212 of the whistle mouthpiece 210 at a sufficient rate and a sample capture cartridge 100 is present and the whistle button 250 is actuated.

In some embodiments, the sample capture cartridge 100 includes a noise maker that makes a noise when fluid is pushed through (e.g., blown through) the sample capture cartridge 100 and out of the lens cap vent 114 of the cartridge lens cap 110 at a sufficient rate. In some embodiments, the sample capture cartridge 100 includes a noise maker that makes a first noise after the whistle button 250 of the sample collection whistle 200 has been actuated (e.g., only after the whistle button 250 has been actuated may there be sufficient flow through the noise maker to produce the first sound).

In some embodiments both the sample collection whistle 200 and the sample capture cartridge 100 include a noise maker. For example the sample collection whistle 200 may include a noise maker that makes a first noise when fluid is pushed through the whistle sample inlet 212 of the whistle mouthpiece 210 at a sufficient rate (regardless of whether a sample capture cartridge 100 is in place and/or whether a sample capture cartridge 100 is in place and the whistle button 250 is actuated). The sample capture cartridge 100 may include a noise maker than makes a second noise when fluid is pushed through the sample capture cartridge 100 (e.g., into the cartridge desiccant canister 140 or out of the lens cap vents 114) at a sufficient rate. In such embodiments, a first noise may be generated upon pushing a fluid through the whistle sample inlet 212 of the whistle mouthpiece 210 at a sufficient rate, but the second noise (e.g., of the noise maker of the sample capture cartridge 100) will not be generated until the whistle button 250 is actuated (e.g., a seal is created between the sample capture cartridge 100 and the cartridge sealing grommet 214) such that sufficient fluid is forced through the sample capture cartridge 100.

Embodiments of the sample collection whistle 200 and/or sample capture cartridge 100 that include one or more noisemakers may advantageously facilitate simple sample segmentation. For example, a microphone, a processor and a software (e.g., a mobile phone having a microphone and an app) may be able to detect any of noises (e.g., sounds, tones, notes, etc.) discussed above (e.g., the first noise, second noise, and/or third noise). The processor and software (e.g., sound analyzer) may therefore detect any of a number of things, by analyzing the noise(s) produced by the sample collection whistle 200 and/or sample capture cartridge 100. For example, the sound analyzer may be able to detect when a sample is being pushed through the sample collection whistle 200 at a rate sufficient to be an appropriate sample (e.g., it can detect the beginning of sample flow) (e.g., when it detects a sound indicative of the sample flow). The sound analyzer may also be able to detect the presence of a sample capture cartridge 100 (e.g., when it detects a sound indicative of sample flow, but either a sound indicative of the absence of the sample capture cartridge 100 or the absence of a sound indicative of the sample capture cartridge 100). The sound analyzer may also be able to detect when the whistle button 250 was actuated (e.g., it may be able to detect a change in the sound or detect the addition of another sound).

In view of the above, a sound analyzer may be able to provide real-time segmentation instructions to a user. For example, if a late segment sample is desirable, the sound analyzer may start a time upon hearing a sound indicative of the beginning of sample flow. After a sufficient time has passed such that the late segment of the sample has been reached, the sound analyzer may signal the user to actuate the whistle button 250 to engage the sample capture cartridge 100 with the sample stream and capture at least part of the late segment sample. The sound analyzer may be able to determine the success of the sample collection based on the change of the sound (e.g., pitch, volume, and/or any new sounds) and the duration of such changed sound. In some embodiments, the sound analyzer may be attached to an automatic actuator that may replace the whistle button 250. In such embodiments, the sound analyzer may automatically segment a sample based on any of a number of criteria, which may be pre-programmed into the sound analyzer.

Electronic Sample Collection Whistle

Figure 26A:
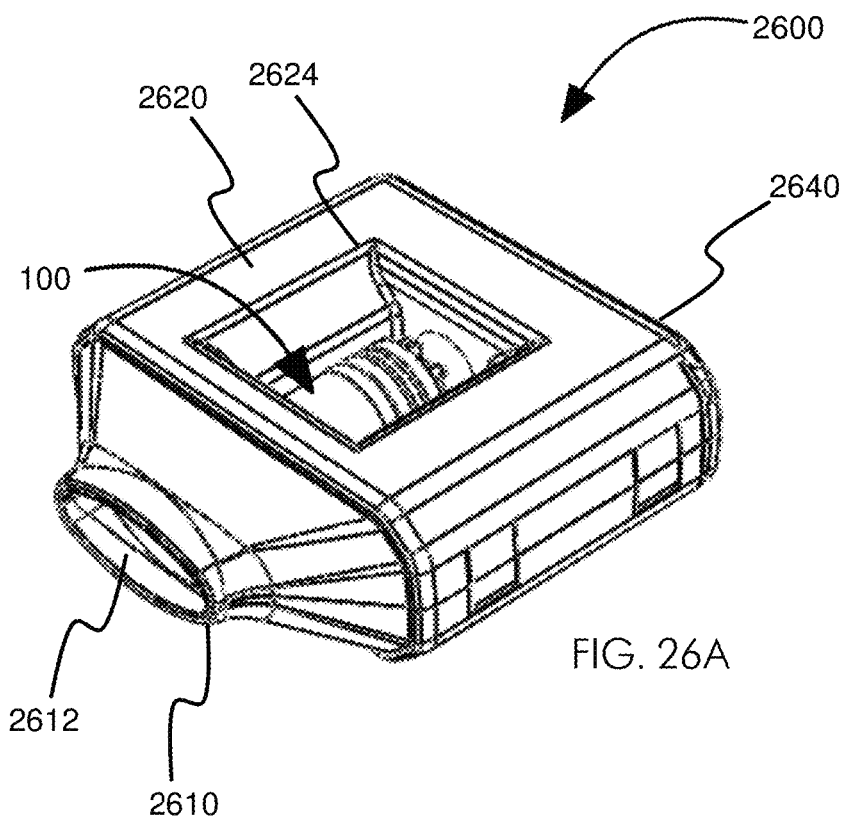
Figure 26B:
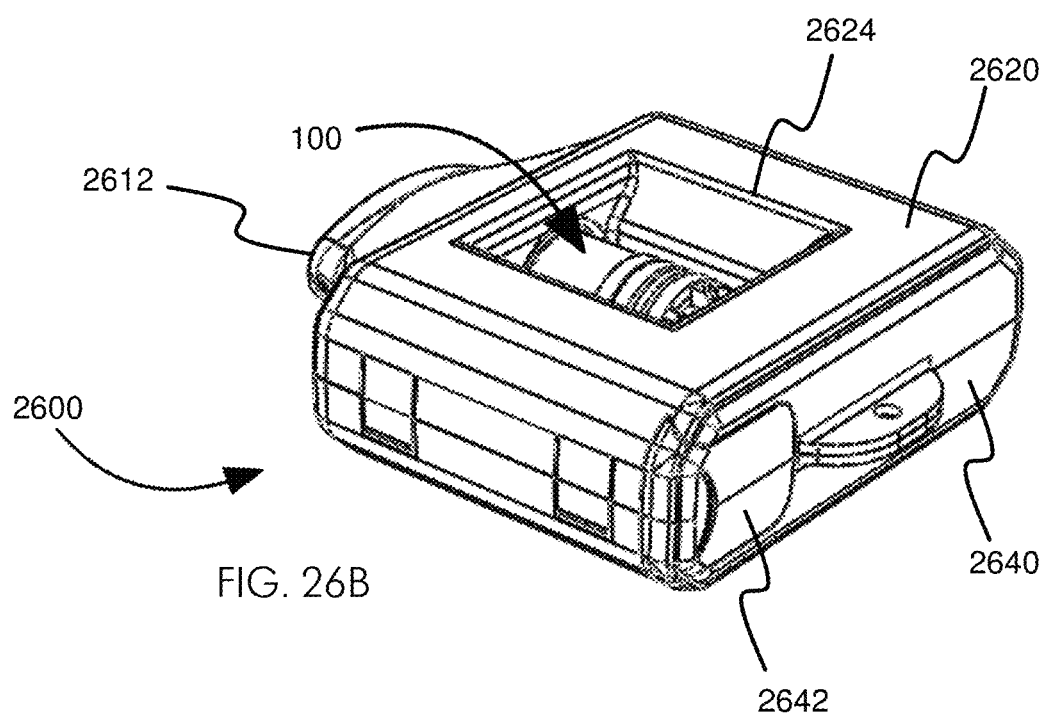

FIGS. 26A-26B illustrate various views of an embodiment of a sample capture cartridge 100, as disclosed herein, installed or placed in (e.g., snapped into) an embodiment of sample collection whistle 2600. While the sample collection whistle 2600 is discussed in additional detail herein, FIG. 26A shows sample capture cartridge 100 loaded in the sample collection whistle 2600 from a top-front biased three-quarters view. In much the same way, FIG. 26B shows the sample capture cartridge 100 loaded in the sample collection whistle 2600 from a top-rear biased three-quarters view.

FIGS. 26C-26E show the sample collection whistle 2600 of FIGS. 26A-26B with one or more external components, such as a plastic housing, removed, so that the various internal components of the sample collection whistle 2600 may be better seen. FIG. 26C shows a front-top biased three quarters view of the internal components of the sample collection whistle 2600, e.g., with various external housing components removed. FIG. 26D-26E show a rear-top biased three quarters view of the internal components of the sample collection whistle 2600, e.g., with various external housing components removed.

One or more components of the sample collection whistle 2600 of FIGS. 26A-26E may be similar in structure and/or function to the sample collection whistle 200 of FIGS. 8A-10D. For example: the whistle sample inlet 2612 may correspond to the whistle sample inlet 212; the whistle mouthpiece 2610 may correspond to the whistle mouthpiece 210, the cartridge insertion window 2624 may correspond to the cartridge insertion window 224; the whistle back 2640 may correspond to the whistle back 240; and the cartridge sealing grommet 2614 may correspond to the cartridge sealing grommet 214. While some components may be similar, or even identical between the sample collection whistle 2600 and the sample collection whistle 200, none are required to be similar, substantially similar, or identical.

As shown in FIG. 26A, the sample collection whistle 2600 has a whistle body 2620 with a cartridge insertion window 2624 at or near its middle. The cartridge insertion window 2624 may be at any location convenient for a user to insert and remove a sample capture cartridge 100 from within the cartridge insertion window 2624. At the front of the sample collection whistle 2600, best seen in FIG. 26A, is a whistle mouthpiece 2610 having a whistle sample inlet 2612. As best seen in FIG. 26B, the sample collection whistle 2600 includes a whistle back 2640 at its rear. The rear of the sample collection whistle 2600 may also include a battery cover 2642 that may be opened and closed by a user to remove and/or replace batteries into the whistle body 2620.

In some embodiments, the sample collection whistle 2600 includes two flow paths (e.g., most relevant when a sample capture cartridge 100 is in place within the sample collection whistle 2600), a sample collection flow path and an exhaust or venting flow path. The sample collection flow path begins at the whistle mouthpiece 2610, where it passes into the whistle sample inlet 2612, through the cartridge sealing grommet 2614, through the sample capture cartridge 100, and out of the lens cap vents 114 of the sample capture cartridge 100 to the atmosphere. The exhaust or venting flow path begins at the whistle mouthpiece 2610, where it passes into the whistle sample inlet 2612, then through the exhaust vent 2685 and out to the atmosphere. Flow of gases through these two flow paths may be dependent or modulated based on the restriction to flow of the various flow paths.

In some embodiments, the restriction to flow of the exhaust or venting flow path has an opened configuration and a closed configuration. In some embodiments, the exhaust or venting flow path may be opened and closed in many different ways. As shown in FIGS. 26C-26D, the sample collection whistle 2600 includes a solenoid 2682 that drives a stop shaft 2684, e.g., linearly drives. The solenoid 2682 is configured to drive stop shaft 2684 to extend it into the exhaust vent 2685 to close the exhaust vent 2685, thereby blocking the exhaust or venting flow path. In the same way, the solenoid 2682 is configured to drive stop shaft 2684 to withdraw it from the exhaust vent 2685 to open the exhaust vent 2685, thereby opening the exhaust or venting flow path. The stop shaft 2684 may mate, e.g., closely mate or sealingly mate, with the exhaust vent 2685 such that when the stop shaft 2684 is within the exhaust vent 2685, the flow through the exhaust or venting flow path is decreased by at least about 80%, at least about 85%, at least about 87.5%, at least about 90%, at least about 92.5%, at least about 95%, at least about 97.5%, or at least about 99%. FIG. 26D shows the stop shaft 2684 backed out of the exhaust vent 2685, leaving the exhaust or venting flow path open.

When the exhaust or venting flow path is open and a sample capture cartridge 100 is installed in the sample collection flow path, the sample capture cartridge 100 provides a substantial amount of flow resistance, such that the resistance to flow of the exhaust or venting flow path is less, e.g., significantly less, than the resistance to flow of the sample collection flow path. In this case, the amount of flow passing through the exhaust or venting flow path and to the atmosphere is at least about 80%, at least about 85%, at least about 87.5%, at least about 90%, at least about 92.5%, at least about 95%, at least about 97.5%, or at least about 99%. FIG. 26E shows the stop shaft 2684 extending into the exhaust vent 2685, blocking, closing, or sealing the exhaust or venting flow path.

When the exhaust or venting flow path is closed and a sample capture cartridge 100 is installed in the sample collection flow path, the flow is substantially blocked from passing through the exhaust or venting flow path and most of the flow is directed or forced through the sample capture cartridge 100 (less any losses due to imperfect fittings) as a user exhales or blows into the whistle. In this case, the amount of flow passing through the sample collection flow path and through the sample capture cartridge 100 is at least about 80%, at least about 85%, at least about 87.5%, at least about 90%, at least about 92.5%, at least about 95%, at least about 97.5%, or at least about 99%.

In some embodiments, the sample capture cartridge 100 is held securely in the sample collection whistle 2600 (e.g., to create a sealed sample collection flow path) by a ball 2681 (e.g., a plastic ball) and spring 2680 that push the sample capture cartridge 100 anteriorly against the cartridge sealing grommet 2614. Any type of spring or holding mechanism may be used. In some embodiments, in this or any other whistle disclosed herein, the mechanism used to retain the sample capture cartridge 100 within the sample collection whistle minimizes contact with or does not contact the lens cap window 112 so as to advantageously prevent damage to the window that may cause noise or artifacts in subsequent reading of the sample.

The solenoid 2682 may be run by battery 2644, which may be a rechargeable or replaceable battery 2644, e.g., removable by opening the battery cover 2642. Additionally, the sample collection whistle 2600 may include various components, e.g., electrical components, necessary to run the solenoid and or other electrical components of the sample collection whistle 2600. For example, the sample collection whistle 2600 may include a PCB.

The sample collection whistle 2600 may be used to segment breath samples so that deep-lung samples may be selectively collected. In operation, a user may insert a sample capture cartridge 100, e.g., a disposable replaceable cartridge, into the sample collection whistle 2600 through the cartridge insertion window 2624. The sample capture cartridge 100 is held in the sample collection whistle 2600 by the spring 2680 and the ball 2681.

The sample collection whistle 2600 may be turned on in any of a number of ways. In some embodiments, the sample collection whistle 2600 is turned on when the user presses an "on/off" button. In some embodiments, the sample collection whistle 2600 is turned on when the user begins blowing into the whistle sample inlet 2612 of the sample collection whistle 2600, e.g., the sample collection whistle 2600 may have a flow sensor that automatically turns the device on when sufficient flow is sensed. In some embodiments, the sample collection whistle 2600 is turned on when the user interacts with an application on a mobile device, such as a smart phone (e.g., the sample collection whistle 2600 may have wired or wireless connectivity such that it may connect to and communicate with another device).

To collect a deep-lung breath sample, the sample collection whistle 2600 selectively vents an initial portion of the user's breath. To do this, the sample collection whistle 2600 keeps the exhaust or venting flow path open for a set portion of the user's breath (as discussed above, the exhaust or venting flow path is open when the solenoid 2682 has backed the stop shaft 2684 out of the exhaust vent 2685). When the exhaust or venting flow path is open, a majority of the breath flow being generated by the user will be exhausted to the atmosphere, rather than passing through and being collected by the sample capture cartridge 100. The sample collection whistle 2600 may segment the user's breath based on any of a number of factors, such as time, pressure, flow rate, flow volume, or any of a number of other criteria that may be patient specific and programmed into the sample collection whistle 2600 (alternatively, the sample collection whistle 2600 may communicate with and receive segmenting instructions from the aforementioned mobile device). In addition, the device may detect the beginning of exhalation and use that time point as the start, e.g., starting point, for one or more measurements, such as flow, time, volume, etc.

Once the sample collection whistle 2600 has determined or been instructed that the desired breath segment has been reached, whether by time volume or any other metric, a programmed controller controls the solenoid 2682 and causes it to move the stop shaft 2684 into engagement with the exhaust vent 2685 to close the exhaust or venting flow path. As discussed herein, when the venting or exhaust flow path is closed, gases entering the sample collection whistle 2600 will be forced through the cartridge sealing grommet 2614 and through the sample capture cartridge 100 to be collected as a sample.

Once the flow path has changed, e.g., the solenoid 2682 has closed the exhaust flow path by inserting the stop shaft 2684 into the exhaust vent 2685, the user may continue to exhale for a time during which the sample capture cartridge 100 collects a sample of the user's breath.

In some embodiments, the user merely continues exhaling until he or she is no longer able to exhale (e.g., has no more breath). In some embodiments, the sample collection whistle 2600 is configured to instruct the user when to stop exhaling. In some embodiments, the sample collection whistle 2600 instructs the user to stop exhaling based on the amount of time the user has exhaled. In some embodiments, the sample collection whistle 2600 instructs the user to stop exhaling based on the volume of air that has passed through the sample collection flow path. In some embodiments, the sample collection whistle 2600 instructs the user to stop exhaling based on changes in flow rate of the air passing through the sample collection flow path. In some embodiments, the sample collection whistle 2600 instructs the user to stop exhaling based on feedback received from the mobile device. The task of informing the user when to stop exhaling may be performed by a mobile app based on a wireless signal generated by the whistle, e.g., a component of the whistle.

The sample collection whistle 2600 may provide a signal to the user indicating that he or she should stop exhaling. For example, the sample collection whistle 2600 may include one or more LEDs that signal the user to stop exhaling, e.g., by illuminating, flashing, etc. In addition, or instead of LEDs, the sample collection whistle 2600 may provide an auditory signal, such as beeps, clicks, tones, etc., that signals the user to stop exhaling. Such visual or auditory signals may also be used to instruct the user to begin blowing or exhaling into the 2600.

The sample collection whistle 2600 may be programmed with longer or shorter times for exhausting and sample collection based on user characteristic(s). For example, in some embodiments, the user may input one or more of his or her physical characteristics, e.g., age, gender, weight, health, etc., into the sample collection whistle 2600. In some embodiments, the user may input one or more of his or her physical characteristics, e.g., age, gender, weight, etc., into a mobile device with which the sample collection whistle 2600 communicates. In some embodiments, the exhausting stage can be lengthened in response to one or more of the user's physical characteristics. In some embodiments, the exhausting stage can be shortened in response to one or more of the user's physical characteristics. In some embodiments, the sample collection stage can be lengthened in response to one or more of the user's physical characteristics. In some embodiments, the sample collection stage can be shortened in response to one or more of the user's physical characteristics.

In some embodiments, the sample collection whistle 2600 includes memory such that it can store one or more data regarding the user, testing conditions, one or more tests, etc.

FIGS. 27A-27B illustrate an embodiment of a rotary valve 2700 that may be used in connection with one or more sample collection whistles disclosed herein, e.g., sample collection whistle 2600 (in place of the solenoid 2682 and stop shaft 2684). FIG. 27A shows the rotary valve 2700 in an open, or flow permitting configuration. FIG. 27B shows the rotary valve 2700 in a substantially closed, or flow blocking configuration.

The rotary valve 2700 includes a rotary valve inner sleeve 2712 nested inside a rotary valve outer sleeve 2710. Each of the rotary valve outer sleeve 2710 and rotary valve inner sleeve 2712 includes an outlet 2742. Additionally, the rotary valve inner sleeve 2712 has an inlet 2740. The rotary valve inner sleeve 2712 is configured to rotate within the rotary valve outer sleeve 2710 (or the rotary valve outer sleeve 2710 is configured to rotate about the rotary valve inner sleeve 2712). Rotation of the rotary valve inner sleeve 2712 with respect to the rotary valve outer sleeve 2710 may move the outlet 2742 of the rotary valve outer sleeve 2710 into and out of alignment with the outlet 2742 of the rotary valve inner sleeve 2712. When the outlet 2742 of the rotary valve outer sleeve 2710 completely overlaps with the outlet 2742 of the rotary valve outer sleeve 2710, the rotary valve 2700 is open or permits flow (shown in FIG. 27A). When the outlet 2742 of the rotary valve outer sleeve 2710 is not aligned or overlapping at all with the outlet 2742 of the rotary valve inner sleeve 2712, the rotary valve 2700 is closed or blocks flow. The rotary valve 2700 may block more or less flow based on how much overlap exists between the outlet 2742 of the rotary valve outer sleeve 2710 and the outlet 2742 of the rotary valve inner sleeve 2712. FIG. 27B shows the outlet 2742 of the rotary valve outer sleeve 2710 overlapping only very slightly with the outlet 2742 of the rotary valve inner sleeve 2712: in this case, little flow would be permitted to pass through the rotary valve 2700.

Each of the rotary valve outer sleeve 2710 and the rotary valve inner sleeve 2712 may be constructed out of plastic. The outlet 2742 of the rotary valve outer sleeve 2710 may be substantially perpendicular to an axis of the rotary valve outer sleeve 2710 and the 1712, e.g., a longitudinal axis of the rotary valve outer sleeve 2710 and the rotary valve inner sleeve 2712 (which may lie on the same axis).

One of the rotary valve outer sleeve 2710 and the rotary valve inner sleeve 2712 is fixedly attached to, e.g., press-fitted, onto the drive shaft 2720, which may be connected to a slow-turning, high-torque, micro-motor. In some embodiments, the press fit is tight enough that the motor can turn one of the rotary valve outer sleeve 2710 and the rotary valve inner sleeve 2712 with respect to the other of the rotary valve outer sleeve 2710 and the rotary valve inner sleeve 2712 (e.g., so that the drive shaft 2720 may turn the rotary valve inner sleeve 2712 with respect to the rotary valve outer sleeve 2710).

One or both of the rotary valve inner sleeve 2712 and the rotary valve outer sleeve 2710 may include a turn-stop 2730. The turn-stop 2730 may serve to stop rotation of the rotary valve inner sleeve 2712 with respect to the rotary valve outer sleeve 2710. In some embodiments, when the turn-stop 2730 prevents further turning, the press-fit between the drive shaft 2720 and the rotary valve inner sleeve 2712 is overcome and the motor is allowed to turn the drive shaft 2720 freely inside the rotary valve inner sleeve 2712. This can advantageously allow for imperfect run times of the electronic motor and may prevent the need for any form of sensor feedback, e.g., sensor feedback to the PCB. The motor can be run for an approximate, e.g., non-exact, time to open or close the valve. In some embodiments, the rotary motor is more exact and a turn-stop 2730 is not necessary. When the rotary motor is more precise, the flow rate allowed through the rotary valve 2700 may be modulated based on the overlap between the outlet 2742 of the rotary valve outer sleeve 2710 and the outlet 2742 of the rotary valve inner sleeve 2712.

Hybrid Mechanical and Electronic Sample Collection Whistle

Figure 28A:
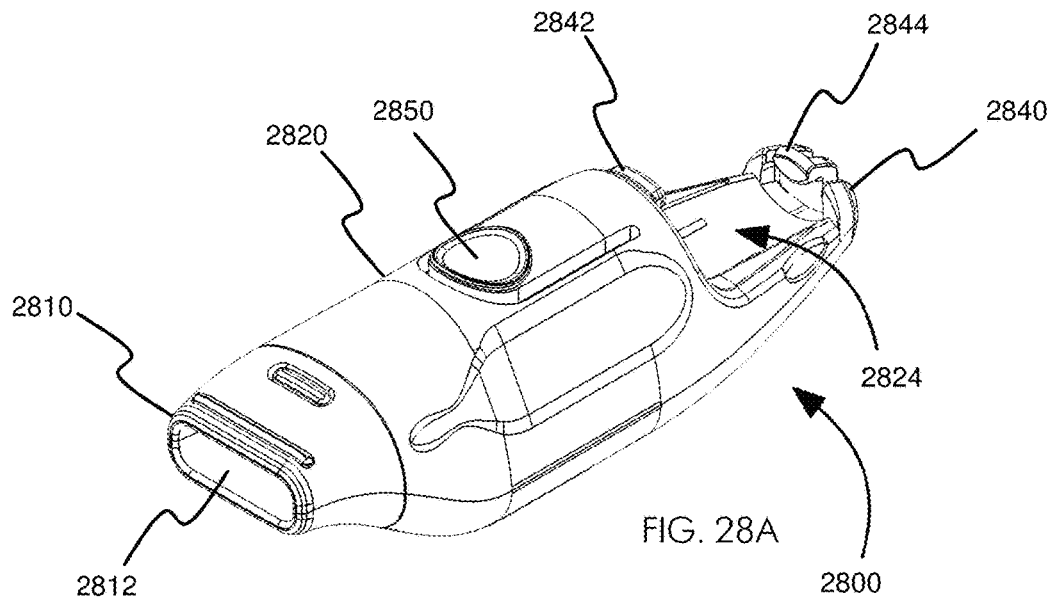
FIGS. 28A-28C show various views of an embodiment of a sample collection whistle.
Figure 28B:
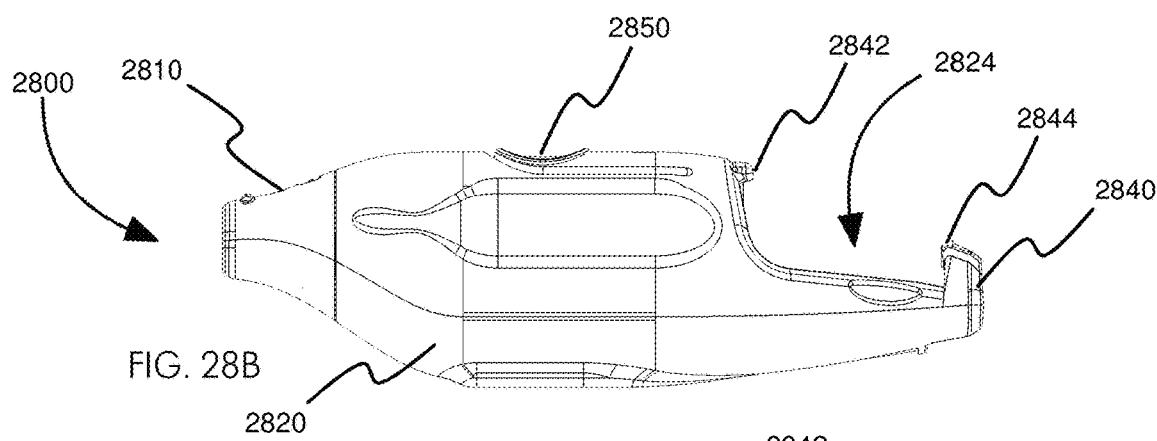
Figure 28C:
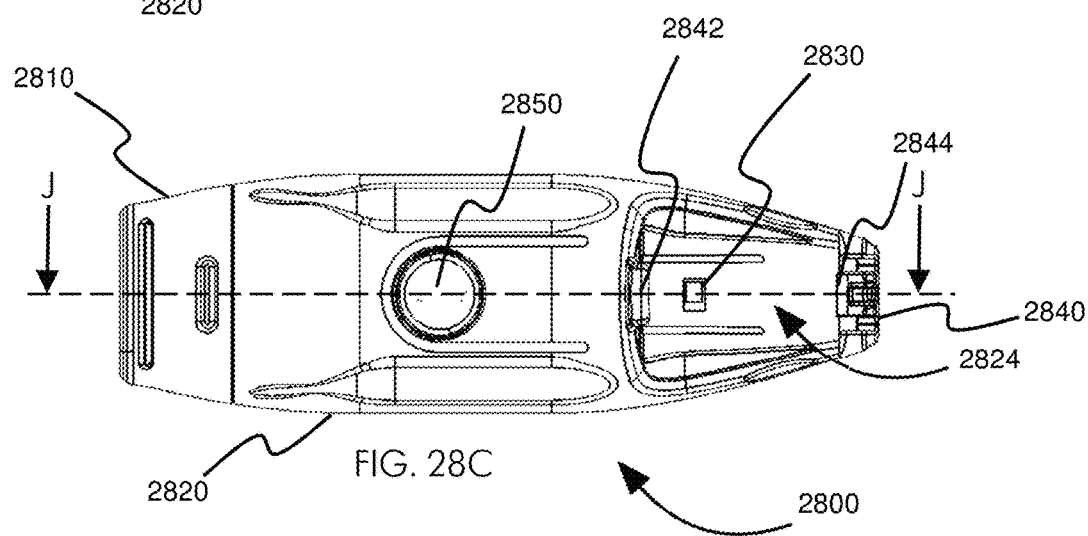
Figure 29A:
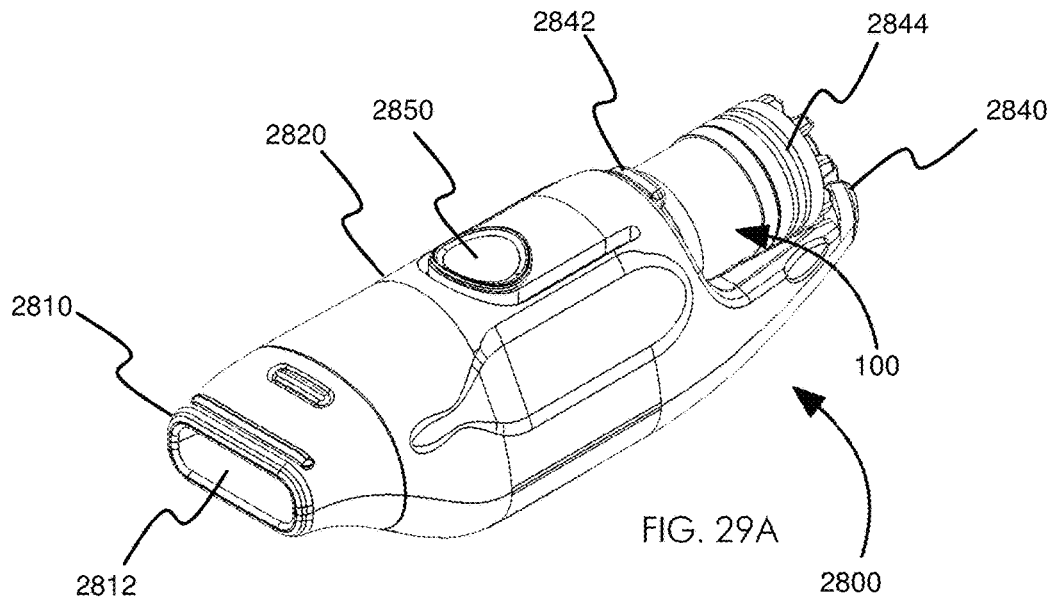
FIGS. 29A-29C show the sample collection whistle of FIGS. 28-28C with a sample capture cartridge loaded into the sample collection whistle.
Figure 29B:
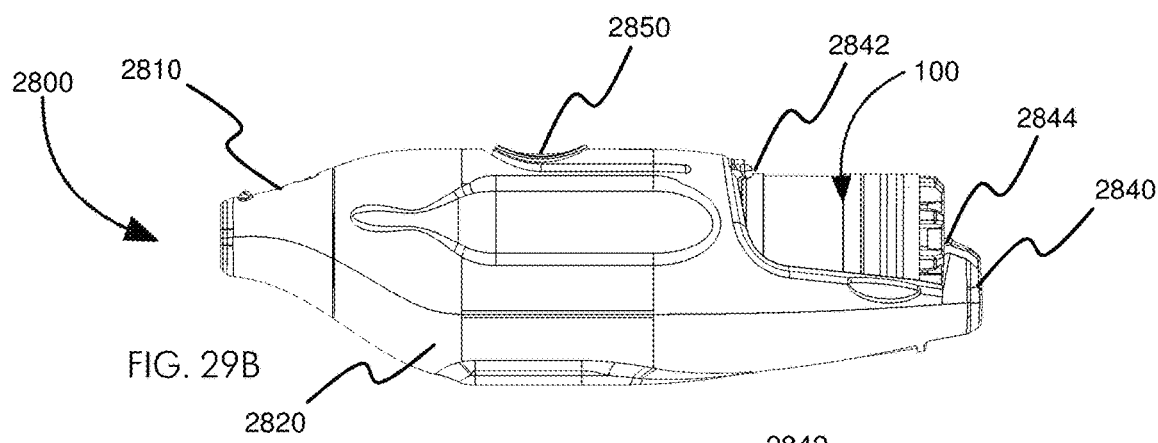
Figure 29C:
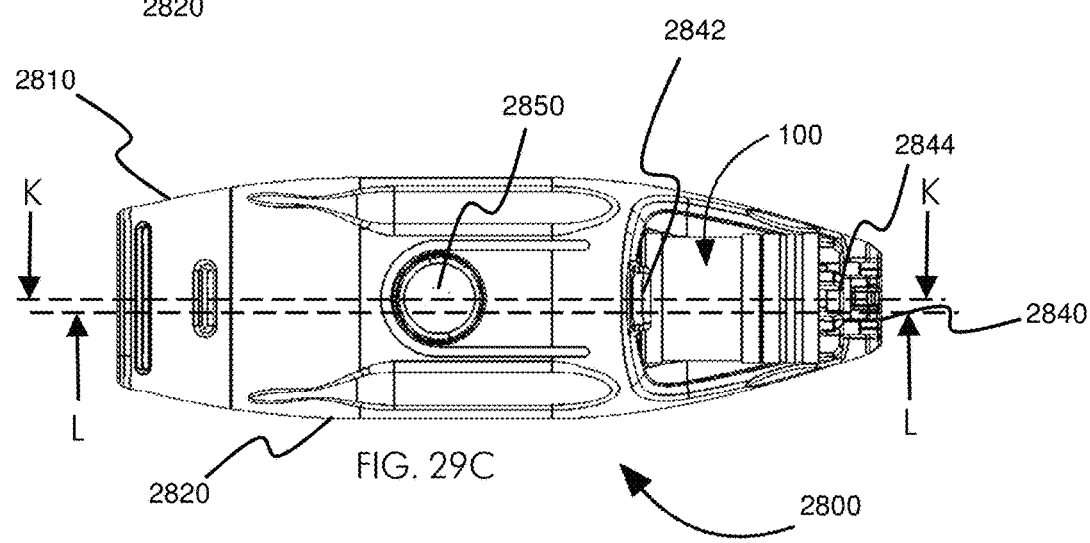

FIGS. 28A-28C, 29A-29C, and 30A-30C illustrate an embodiment of a sample collection whistle 2800 that may be used in conjunction with a sample capture cartridge 100, as disclosed herein, to collect and/or segment a sample. FIGS. 28A-28C show various view of the sample collection whistle 2800 without a sample capture cartridge 100 loaded into the sample collection whistle 2800. FIGS. 29A-29C show the same views as FIGS. 28A-29C, except with a sample capture cartridge 100 loaded into the sample collection whistle 2800, such as it might look while taking a sample. FIGS. 30A-30C show various cross-sectional views of the sample collection whistle 2800 shown in FIGS. 28A-28C and 29A-29C.

One or more components of the sample collection whistle 2800 of FIGS. 28A-28C, 29A-29C, and 30A-30C may be similar in structure and/or function to the sample collection whistle 200 of FIGS. 8A-10D and/or the sample collection whistle 2600 of FIGS. 26A-26E. For example: the whistle sample inlet 2812 may correspond to the whistle sample inlet 212 and/or the whistle sample inlet 2612; the whistle mouthpiece 2810 may correspond to the whistle mouthpiece 210 and/or the whistle mouthpiece 2610; etc. While some components may be similar, or even identical between the sample collection whistle 2800 and the sample collection whistle 200 and/or the sample collection whistle 2600, none are required to be similar, substantially similar, or identical.

FIGS. 28A-28C show a sample collection whistle 2800 without a sample collection cartridge, e.g., without a sample capture cartridge 100. FIG. 28A shows a front-top biased three-quarters view of the sample collection whistle 2800. FIG. 28B shows a right side view of the sample collection whistle 2800. FIG. 28C shows a top view of the sample collection whistle 2800. As shown in FIG. 28A, the sample collection whistle 2800 has at its proximal end a whistle mouthpiece 2810 defining a whistle sample inlet 2812. As disclosed herein, when being used to collect a breath sample, a user may blow into (e.g., place his/her lips around the whistle mouthpiece 2810 and exhale into) the whistle sample inlet 2812 and into the whistle mouthpiece 2810 to take a breath sample.

At its distal end, the sample collection whistle 2800 has a cartridge socket 2824 and a whistle back 2840 (shown clearly in FIG. 28B). The cartridge socket 2824 is configured to accept a sample collection cartridge, e.g., a sample capture cartridge 100, as disclosed herein. To retain the sample capture cartridge within the sample collection whistle 2800, the cartridge socket 2824 may have one or both of a front cartridge retaining clip 2842 and a back cartridge retaining clip 2844. Either one or both of the back cartridge retaining clip 2844 and the front cartridge retaining clip 2842 may have a lip configured to extend over and hold a portion of a sample collection cartridge. In some embodiments, the back cartridge retaining clip 2844 minimizes contact with or does not contact the lens cap window 112 so as to advantageously prevent damage to the window that may cause noise or artifacts in subsequent reading of the sample.

In some embodiments, either one or both of the back cartridge retaining clip 2844 and the front cartridge retaining clip 2842 has an indexing feature(s) configured to retain the sample collection cartridge in a certain (e.g., rotational) orientation during sampling. For example, the back cartridge retaining clip 2844 may have one or more small tabs configured to fit within the one or more lens cap vents 114 of the sample capture cartridge 100 and prevent rotation of the sample capture cartridge 100 during sampling.

Between the proximal end and the distal end, the sample collection whistle 2800 has a whistle body 2820. Additionally, on top of the sample collection whistle 2800 is a whistle button 2850. In some embodiments, the whistle button 2850 is used, at least in part, to segment the user's breath. For example, the user's breath is vented until the user presses the button, at which time, the user's breath is passed through the sample collection cartridge.

In some embodiments, as shown in FIG. 28C, the sample collection whistle 2800 includes an under-cartridge LED 2830. The under-cartridge LED 2830 may be used to illuminate the sample capture cartridge 100. In some embodiments, the illumination of the sample capture cartridge 100 provided by the under-cartridge LED 2830 may be provided for decorative purposes. In some embodiments, the under-cartridge LED 2830 serves as a power indicator, e.g., when the sample collection whistle 2800 is powered on or prepared to take a sample, the under-cartridge LED 2830 is lit, but when the sample collection whistle 2800 is powered off or not prepared to take a sample, the under-cartridge LED 2830 is not lit. In some embodiments, the sample collection whistle 2800 includes various electronics and power portions, e.g., battery or power cord, as may be needed to operate the various components discussed herein.

In some embodiments, the sample collection whistle 2800 includes a speaker or noise-maker that may be configured to provide auditory signals to a user of the sample collection whistle 2800. For example, the speaker or noise-maker may be configured to beep to signal the user to take an action or stop an action. Any various other types of signaling may be used to communicate commands or instructions to the user, for example visual, haptic, or auditory signals may be used (e.g., lights, buzzers, beeps, etc.).

FIG. 29A shows the sample collection whistle 2800 shown in FIG. 28A with a sample capture cartridge 100 loaded into the 2824 and held down by the front cartridge retaining clip 2842 (at the bottom of the sample capture cartridge 100). As can be seen, the front cartridge retaining clip 2842 may provide a lip under which the edge, e.g., the bottom edge, of the sample capture cartridge 100 may fit and be held, e.g., securely held.

FIG. 29B illustrates the sample collection whistle 2800 shown in FIG. 28B with a sample capture cartridge 100 loaded into the cartridge socket 2824 and held by the back cartridge retaining clip 2844 (e.g., at the top of the sample capture cartridge 100) and held down by the front cartridge retaining clip 2842 (at the bottom of the sample capture cartridge 100). Again, it is clearly shown that the front cartridge retaining clip 2842 may provide a lip under which the edge, e.g., the bottom edge, of the sample capture cartridge 100 may fit and be held, e.g., securely held. Furthermore, it may be seen that the back cartridge retaining clip 2844 provides a lip or hook that extends over a least a portion of the top of the sample capture cartridge 100 to hold it during sample collection.

FIG. 29C illustrates the sample collection whistle 2800 shown in FIG. 28C with a sample capture cartridge 100 loaded into the cartridge socket 2824 and held by the front cartridge retaining clip 2842 and the back cartridge retaining clip 2844. With reference to FIGS. 28C and 29C, it will be appreciated that when a translucent sample capture cartridge 100 (or a sample capture cartridge 100 having a translucent cartridge lens cap 110 or a translucent cartridge desiccant canister 140) is inserted, the under-cartridge LED 2830 may cause the sample capture cartridge 100 to "glow" when the under-cartridge LED 2830 is turned on. Such "glowing" of the sample capture cartridge 100 may be used to signal the user to take an action or to stop an action. Alternatively, the "glowing" of the LED 2830 or the sample capture cartridge 100 may indicate that the whistle is ready to receive a breath sample from the user.

FIGS. 30A-30C are cross-sectional views of the sample collection whistle 2800. FIG. 30A illustrates the sample collection whistle 2800 of FIG. 28C taken along line J-J, e.g., this figure shows a mid-line cross-section with no sample capture cartridge 100 in place within the cartridge socket 2824. FIG. 30B illustrates the sample collection whistle 2800 of FIG. 29C taken along line K-K, e.g., this figure shows a mid-line cross-section with a sample capture cartridge 100 in place within the cartridge socket 2824 (except for the presence/absence of the sample capture cartridge 100, FIGS. 30A and 30B are the same). FIG. 30C illustrates the sample collection whistle 2800 of FIG. 29C taken along line L-L.

As may be seen from the cross-sectional views of FIGS. 30A-30C, the sample collection whistle 2800 includes a sample conduit 2860 that connects the whistle mouthpiece 2810 and the whistle sample inlet 2812 to the front cartridge retaining clip 2842. The sample conduit 2860 may be a flexible hose. In some embodiments, the sample conduit 2860 is a rubber hose. The proximal end of the sample conduit 2860 connects or couples to the whistle mouthpiece 2810 and the whistle sample inlet 2812. The distal end of the sample conduit 2860 terminates at the front cartridge retaining clip 2842. Due to its, at least partially, flexible nature, the distal end of the sample conduit 2860 may also serve as a gasket or sealing ring against which the sample capture cartridge 100 may be pushed and held by the back cartridge retaining clip 2844. In this way, the distal end of the sample conduit 2860 may serve as a replacement for the cartridge sealing grommet 214 and/or the cartridge sealing grommet 2614 of the sample collection whistle 200 and the sample collection whistle 2600, respectively. As shown in FIG. 30B, to load the sample capture cartridge 100 into the sample collection whistle 2800, the bottom edge of the sample capture cartridge 100 may be slipped under the front cartridge retaining clip 2842 and against the distal end of the sample collection whistle 2800 and pushed into the distal end of the sample collection whistle 2800 so that the proximal end of the sample capture cartridge 100 may slip under the back cartridge retaining clip 2844. The tight fit between the sample capture cartridge 100 and the distal end of the sample collection whistle 2800 may serve to seal or substantially seal the bottom of the sample capture cartridge 100 to the distal end of the sample collection whistle 2800 (e.g., with an airtight or substantially airtight seal).

The sample collection whistle 2800 includes a hole on its dorsal, or top, side through which the button extension 2851 of the whistle button 2850 extends. As shown most clearly in FIG. 30C, an exhaust vent 2885 surrounds the button extension 2851 allowing gases to exhaust or vent around the button extension 2851 and past the whistle button 2850.

The sample collection whistle 2800 includes two flow paths through which gases may flow. The first flow path, or the exhaust or venting flow path starts at the whistle mouthpiece 2810, and enters through the whistle sample inlet 2812, passes through the exhaust vent 2885 in the top of the 2880, and goes past the whistle button 2850 (e.g., when the whistle button 2850 is not depressed to seal the whistle button 2850). The second flow path, or the sample collection flow path, starts, again, at the whistle mouthpiece 2810, and enters through the whistle sample inlet 2812, passes through the length of the sample conduit 2860 and enters the sample capture cartridge 100 where, because of the seal formed between the bottom of the sample capture cartridge 100 and the distal end of the sample conduit 2860, it passes through the sample capture cartridge 100 and exits through the lens cap vents 114.

In some embodiments, the exhaust or venting flow path has an open configuration and a closed configuration. The whistle button 2850 serves as an on/off switch, or flow reducer, for the exhaust vent 2885 (e.g., on, off, or modulation between the two). When the whistle button 2850 is not being pushed or depressed, the exhaust vent 2885 is fully open. When the whistle button 2850 is being pushed or depressed (e.g., pushed or depressed fully), the whistle button 2850 is configured to push down against the outer surface of the top of the sample conduit 2860 and seal, or substantially seal, the exhaust vent 2885 (e.g., with an airtight or substantially airtight seal).

When the whistle button 2850 is not depressed and the exhaust vent 2885 is fully open and a sample capture cartridge 100 is present, the sample capture cartridge 100 provides a substantial amount of flow resistance, such that the resistance to flow of the exhaust or venting flow path is less, e.g., significantly less, than the resistance to flow of the sample collection flow path. When the whistle button 2850 is not depressed and the exhaust vent 2885 is fully open, the amount of flow passing through the exhaust or venting flow path and to the atmosphere is at least about 80%, at least about 85%, at least about 87.5%, at least about 90%, at least about 92.5%, at least about 95%, at least about 97.5%, or at least about 99%.

When the whistle button 2850 is depressed, the whistle button 2850 may mate, e.g., closely mate or sealingly mate (e.g., with an airtight or substantially airtight seal), with the exhaust vent 2885 such that the flow through the exhaust or venting flow path is decrease by at least about 80%, at least about 85%, at least about 87.5%, at least about 90%, at least about 92.5%, at least about 95%, at least about 97.5%, or at least about 99%.

As discussed herein, the sample conduit 2860 may be flexible. Such flexibility allows the button extension 2851 of the whistle button 2850 to push down on an interior, ventral, surface of the sample conduit 2860 sufficiently such that push button 2832 below the sample conduit 2860 is activated. In this way, push button 2832 serves as feedback to identify when the whistle button 2850 is being pushed. Alternatively stated, the push button 2832 may serve as feedback to identify when gases, e.g., breath, is passing through the exhaust or venting flow path, or when gases, e.g., breath, is passing through the sample collection flow path.

The sample collection whistle 2800 may be used to segment breath samples so that deep-lung samples may be selectively collected. In operation, a user may insert a sample capture cartridge 100, e.g., a disposable replaceable cartridge, into the cartridge socket 2824 of the sample collection whistle 2800 by pushing it against the distal end of the sample conduit 2860 and under the lip of the front cartridge retaining clip 2842. The user may push the sample capture cartridge 100 against the sample conduit 2860 sufficiently hard that the top of the sample capture cartridge 100 may slip or fit under the back cartridge retaining clip 2844.

The sample collection whistle 2800 may be turned on in any of a number of ways, similar to those of other sample collection whistles disclosed herein. In operation, a sample capture cartridge 100 may inserted into the sample collection whistle 2800 and the sample collection whistle 2800 may be turned on. The sample collection whistle 2800 signals the user when to begin blowing into the whistle mouthpiece 2810, for example, by using an aural tone (e.g., a beep) or a light (e.g., a flashing light or a light of a certain color). As the user blows into the sample collection whistle 2800, the breath is exhausted (or primarily exhausted) out of the exhaust vent 2885 because of its lower resistance to flow. The sample collection whistle 2800 will register that the breath is being exhausted because the push button 2832 recognizes the presence or absence of the button extension 2851 of the whistle button 2850, which is correlated to opening and closing, respectively of the exhaust vent 2885.

As disclosed herein, various types of signals may be presented to the user as instructions or cues. For example, the various sample collection whistles disclosed herein may use an aural tone (e.g., a beep) or a light (e.g., a flashing light or a light of a certain color). Any of the various sample collection whistles disclosed herein may also include one or more of a processor and a speaker or a processor and a transmitter configured to transmit a signal ultimately to a speaker. For example, the sample collection whistle may include a processor and a speaker. The sample collection whistle may include only a processor and a transmitter, the processor and speaker configured to transmit a signal to one or more of a processor and a speaker external to the sample collection whistle (e.g., in a mobile device such as a smart phone). The processor and speaker (and transmitter, if present) may be configured to provide instructions to a user in any language (e.g., any language programmed into the processor). For example, the processor and speaker may be configured to provide audio instructions to the user, including, but not limited to: "press the button," "hold and exhale," "test complete," etc. The instructions provided to the user may be responsive to one or more conditions sensed and or reported by the sample collection whistle, including, but not limited to time, volume of fluid passing through the whistle, flow rate of fluid passing through the whistle, etc.

When the sample collection whistle 2800 detects, as is disclosed herein, that the desired breath segment has been reached, the sample collection whistle 2800 may change the signal to the user signaling the user to depress the whistle button 2850. When the whistle button 2850 is depressed, the exhaust vent 2885 is closed and the breath sample is forced through the sample capture cartridge 100. The sample collection whistle 2800 will register the flow path change because the push button 2832 will be activated by the button extension 2851 of the whistle button 2850 when the user presses the whistle button 2850. In some embodiments, the push button 2832 will not be properly activated until the whistle button 2850 is pressed down sufficiently far to effectively or substantially seal the exhaust vent 2885 (e.g., an airtight seal).

In some embodiments, when the sample collection whistle 2800 detects a flow path change (e.g., from exhausting to sample collection), it begins counting down the proper sample collection duration. The whistle may include a programmed controller that handles or controls the task of counting down the proper sample duration and any of the other various signaling tasks that may be required. Sample collection duration may be based on such factors as time, flow rate, flow volume, etc., as disclosed herein. In some embodiments, when the sample collection whistle 2800 detects a flow path change (e.g., from exhausting to sample collection), it changes a signal to the user, e.g., the visual, haptic, or auditory signal is changed. For example, when the sample collection whistle 2800 detects that sufficient breath has vented, the sample collection whistle 2800 may change from a beeping noise at a given tone to a sustained noise at a different tone. In some embodiments, when the sample collection whistle 2800 has detected that a sufficient sample has been collected, as disclosed herein, it again changes a signal to the user, e.g., the visual, haptic, or auditory signal is changed. In this way, the sample collection whistle 2800 may be configured to signal to the user when to begin or when to stop certain actions, including, but not limited to exhalation, whistle button 2850 depression, whistle button 2850 release, etc.

In some embodiments, the various sample collection whistles disclosed herein may incorporate sensor circuitry and/or components for analyzing a sample collection cartridge. Additionally, the various sample collection whistles disclosed herein may include a wireless transceiver for communicating with any other device, e.g., a mobile device or phone. In some embodiments, the various sample collection whistles disclosed herein may incorporate sufficient circuitry, components, transceivers, and/or sensors that no base unit or separate sample collection cartridge analyzer is needed to analyze the used sample collection cartridge(s), e.g., the sample collection whistle may be configured to both facilitate collection of the sample in the sample collection cartridge (e.g., segmenting and directing the breath) and analyze the sample collected by the sample collection cartridge.

Some embodiments of the sample collection whistles disclosed herein are portable, small, or hand-held devices. In some embodiments, the sample collection whistle is less than about 10 cm long. In some embodiments, the sample collection whistle is shorter than about 20 cm, shorter than about 19.5 cm, shorter than about 19 cm, shorter than about 18.5 cm, shorter than about 18 cm, shorter than about 17.5 cm, shorter than about 17 cm, shorter than about 16.5 cm, shorter than about 16 cm, shorter than about 15.5 cm, shorter than about 15 cm, shorter than about 14.5 cm, shorter than about 14 cm, shorter than about 13.5 cm, shorter than about 13 cm, shorter than about 12.5 cm, shorter than about 12 cm, shorter than about 11.5 cm, shorter than about 11 cm, shorter than about 10.5 cm, shorter than about 10 cm, shorter than about 9.5 cm, shorter than about 9 cm, shorter than about 8.5 cm, shorter than about 8 cm, shorter than about 7.5 cm, shorter than about 7 cm, shorter than about 6.5 cm, shorter than about 6 cm, shorter than about 5.5 cm, shorter than about 5 cm, shorter than about 4.5 cm, shorter than about 4 cm, shorter than about 3.5 cm, shorter than about 3 cm, shorter than about 2.5 cm, or shorter than about 2 cm. In some embodiments, the sample collection whistle weighs less than about 300 grams, less than about 280 grams, less than about 260 grams, less than about 240 grams, less than about 220 grams, less than about 200 grams, less than about 180 grams, less than about 160 grams, less than about 140 grams, less than about 120 grams, less than about 100 grams, less than about 80 grams, less than about 60 grams, or less than about 40 grams.

1 Piece Breather

The various sample capture cartridges 100 disclosed herein may be used with any of a number of cartridge holders and/or sample collectors. For example, some embodiments of the sample capture cartridge 100 are configured to be used with a sample collection whistle 200 as disclosed herein. The sample collection whistle 200 may be advantageously re-usable for a number of reasons. For example, the sample collection whistle 200 may be relatively complex, it may incur more than a comparatively low, e.g., de minimis cost, it may be particularly well suited towards segmenting samples, etc. In some embodiments, it may be advantageous to use a sample collection/capture cartridge with a simpler and/or disposable cartridge holder. For example, in some instances sample segmentation may not be particularly important. Rather, the mere presence and/or identification of an analyte of interest, irrespective of time, may be the primary objective. Additionally, it may be advantageous to have a cartridge holder that may be disposable, e.g., is small and relatively inexpensive. For example, point of care testers may need to use a new cartridge holder with each patient they see, i.e., for a number of reasons they may not be able to sterilize and re-use a cartridge holder. In such cases, a cartridge holder such as the sample collection whistle 200 may prove too complex and/or expensive for disposal. In such cases a one piece breather may advantageously be used.

Figure 12A:
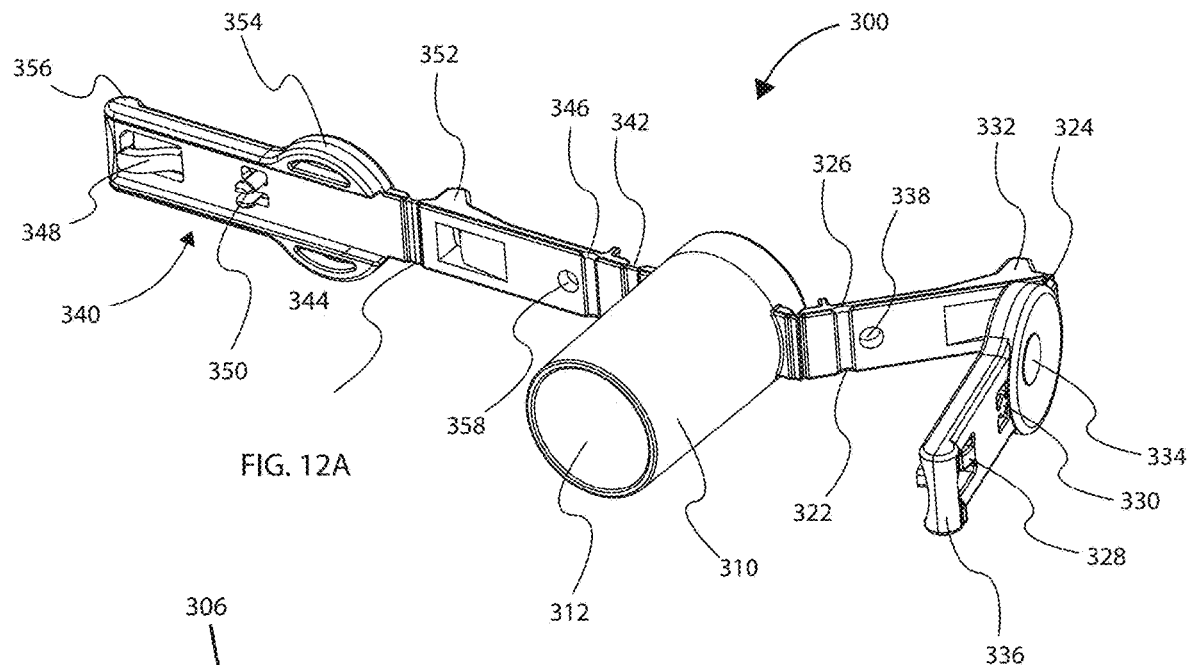
FIGS. 12A-12B show various views in an extended configuration of an embodiment of a one piece breather that may be used to collect samples.
Figure 12C:
FIG. 12C shows an embodiment of a cartridge sealing grommet that may be used in conjunction with various sample collection devices, such as the one piece breather of FIGS. 12A-12B.
Figure 12B:
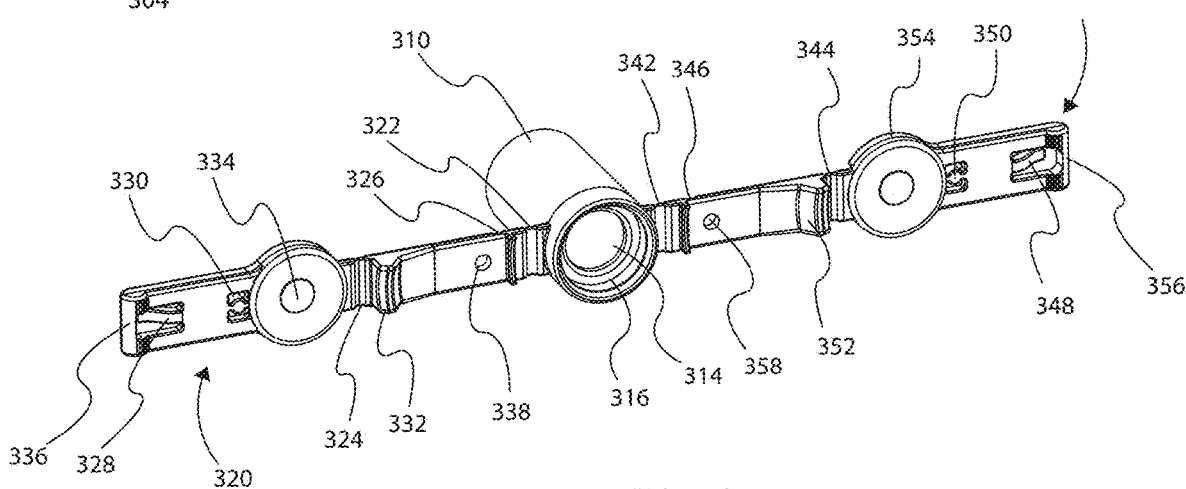

FIGS. 12A and 12B illustrate front and rear views of an unassembled one piece breather 300. With reference to FIG. 12B, the one piece breather 300 includes, at its core a breather body 310 having a grommet ridge 314 and a breather body cartridge port 316. The grommet ridge 314 is configured to accept and hold a cartridge sealing grommet 302, such as that shown in FIG. 12C.

The cartridge sealing grommet 302 may be used to help seal a sample collection cartridge to the one piece breather 300 to prevent leakage of sample between the sample collection cartridge (e.g., a sample capture cartridge 100) and the one piece breather 300. As will be readily understood, other structures or features may be used to accomplish similar ends. As such, some embodiments of the one piece breather 300 do not include a cartridge sealing grommet 302 (or the grommet ridge 314 that may be used to hold the cartridge sealing grommet 302). The cartridge sealing grommet 302, an example of which is shown in FIG. 12C, may have a grommet groove 304 and a grommet port 306. The cartridge sealing grommet 302 may snap into the breather body 310 such that the grommet groove 304 lies over and grips the grommet ridge 314. The cartridge sealing grommet 302 may function similarly to the cartridge sealing grommet 214 discussed in connection with the sample collection whistle 200. As with that cartridge sealing grommet 214, the cartridge sealing grommet 214 may be a lower durometer material, such as a rubber, that is configured to advantageously form a tight seal with a sample collection cartridge (e.g., the cartridge desiccant canister 140 of the sample capture cartridge 100) (e.g., the cartridge sealing grommet 214 has a diameter that is larger than the diameter of the cartridge desiccant canister 140 of the sample capture cartridge 100 such that the entire perimeter of the lower surface or ring of the cartridge desiccant canister 140 may be effectively pressed into the cartridge sealing grommet 214).

With continued reference to FIG. 12B, the one piece breather 300 may have two side wings, a first breather wing 320 and a second breather wing 340. One of ordinary skill in the art will understand that various and/or numerous modifications may be made to the one piece breather 300 and various and/or numerous different or alternative structures may be used to accomplish many, if not all, of the functions of the one piece breather 300 disclosed in FIG. 12B. The one piece breather 300 may be produced (e.g., molded, extruded, etc.) and/or provided (e.g., to the user or point of care provider) in the configuration shown in FIG. 12B, e.g., with the wings first breather wing 320 and second breather wing 340 extending from the breather body 310 in a substantially or approximately perpendicular fashion.

Starting from the end of the first breather wing 320 closest to the breather body 310 of the one piece breather 300, in some embodiments the first breather wing 320 includes a first wing first hinge 322, a first wing first spring 326, a first wing snap hole 338, a first wing ramp 332, a first wing second hinge 324, a first wing paddle 334, a first wing snap 330, a first wing second spring 328, and a first wing cartridge ejector 336. Starting from the end of the second breather wing 340 closest to the breather body 310 of the one piece breather 300, in some embodiments the second breather wing 340 includes a second wing first hinge 342, a second wing first spring 346, a second wing snap hole 358, a second wing ramp 352, a second wing second hinge 344, a second wing paddle 354, a second wing snap 350, a second wing second spring 348, and a second wing cartridge ejector 356. In some embodiments, the first breather wing 320 and the second breather wing 340 are bilaterally symmetrical. In some embodiments, the first breather wing 320 and the second breather wing 340 may be different. For example, in some embodiments, one of the wings may be fixed and molded while only the other wing is movable.

Turning to FIG. 12A, the one piece breather 300 is shown from the rear, e.g., the end into which the sample may be directed during use. As can be seen, the breather body 310 includes a breather body inlet 312 into which the sample may be directed during use, e.g., into which a patient may blow. In some embodiments, the breather body 310 may have a cross-sectional diameter that renders the one piece breather 300 hand held. For example the breather body 310 may have a cross-sectional diameter of between about 5-30 mm, between about 5.5-28 mm, between about 6-26 mm, between about 6.5-24 mm, between about 7-22 mm, between about 7.5-20 mm, between about 8-18 mm, between about 8.5-16 mm, between about 9-14 mm, between about 9.5-12 mm, or any other diameter that advantageously facilitates use and collection of samples as disclosed herein. The one piece breather 300 in FIG. 12A is shown with the second breather wing 340 in its extended (e.g., perpendicular) conformation while the first breather wing 320 is shown partially folded.

In operation, to prepare the one piece breather 300 for use, the first breather wing 320 and the second breather wing 340 may be folded in on themselves. In some embodiments, the first wing first hinge 322 and the first wing second hinge 324 are bent so that the first wing snap 330 swings toward the first wing snap hole 338. The first wing snap 330 may snap fully into the first wing snap hole 338, thereby holding the portion of the first breather wing 320 distal to the first wing second hinge 324 (distal being defined as away from the breather body 310 of the one piece breather 300) proximal/close/in contact to/with the portion of the first breather wing 320 proximal to the first wing second hinge 324. In much the same way, the second wing first hinge 342 and the second wing second hinge 344 are bent so that the second wing snap 350 swings toward the second wing snap hole 358. The second wing snap 350 may snap fully into the second wing snap hole 358, thereby holding the portion of the second breather wing 340 distal to the second wing second hinge 344 (distal again being defined as away from the breather body 310 of the one piece breather 300) proximal proximal/close/in contact to/with the portion of the second breather wing 340 proximal to the second wing second hinge 344. The various hinges or pivot points of the one piece breather 300, e.g., the first wing first hinge 322, first wing second hinge 324, second wing first hinge 342, and second wing second hinge 344, may be living hinges, or any other type of hinge that provides sufficient connection and retention as will be readily understood by one of ordinary skill in the art.

The portion of the first breather wing 320 (or corresponding portions of the second breather wing 340) distal to the first wing second hinge 324 may be held to the portion of the first breather wing 320 proximal to the first wing second hinge 324 using any type of connection means known to one of ordinary skill in the art. The figures illustrate a pronged snap/clip being used (e.g., first wing snap 330) that is shoved into first wing snap hole 338. However, any type of fixation or connection may be used, including, without limitation, ramp/step clips on the edge(s) of the first breather wing 320, adhesives, prongs, hooks, buttons, snaps, etc.

FIGS. 13A and 13B illustrate an embodiment of the one piece breather 300 ready for use, e.g., folded into a configuration in which the one piece breather 300 may accept a sample collection cartridge, such as the sample capture cartridge 100 of FIG. 1 (e.g., the first breather wing 320 has been fixed to itself using the first wing snap 330 and first wing snap hole 338 and the second breather wing 340 has been fixed to itself using the second wing snap 350 and the second wing snap hole 358). FIG. 13A shows the one piece breather 300 ready to accept a sample collection cartridge while FIG. 13B shows the one piece breather 300 into which the sample capture cartridge 100 has been placed.

As will be understood with Reference to FIGS. 13A and 12A, the first breather wing 320 and the second breather wing 340 may be held in an inwardly-biased configuration, e.g., with the first wing ramp 332 and the second wing ramp 352 held close towards each other. Such an inwardly-biased configuration may be facilitated, at least in part, by the first wing second spring 328 of the first breather wing 320 and the second wing second spring 348 of the second breather wing 340. These springs help force the first wing first hinge 322 and second wing first hinge 342, respectively, inward to hold the ramps, e.g., the first wing ramp 332 and the second wing ramp 352 close toward each other. When a sample collection cartridge is to be loaded into the one piece breather 300, the ramps may be forced apart from each other, thereby compressing the first wing second spring 328 of the first breather wing 320 and the second wing second spring 348 of the second breather wing 340.

The first wing ramp 332 and the second wing ramp 352 act as a combined ramped interface with an upper edge of a sample collection cartridge. As such, when the first breather wing 320 and the second breather wing 340 are brought closer to each other, e.g., by applying pressure to the first wing paddle 334 and the second wing paddle 354, the first wing ramp 332 and the second wing ramp 352 push "down" on the sample collection cartridge. Each ramp, e.g., first wing ramp 332 and second wing ramp 352, have a ramp angle defined as the angle between the approximately 90 degree outer-most surface of the ramp and the ramped, inward surface (e.g., that interfaces with or contacts the sample collection cartridge). As will be readily understood, the smaller the ramp angle, the more force is placed on the sample collection cartridge when the ramps are brought closer to each other. By extension, the larger the ramp angle, the less force is placed on the sample collection cartridge when the ramps are brought closer to each other. The ramps, e.g., the first wing ramp 332 of the first breather wing 320 and the second wing ramp 352 of the second breather wing 340 may have any angle that advantageously facilitates loading and compression of a sample collection cartridge, e.g., a sample capture cartridge 100, within the one piece breather 300. But, in any event, the ramp angle is less than 90 degrees (e.g., a flat surface parallel to the inner surface of the respective wing, e.g., the first breather wing 320 or the second breather wing 340). In some embodiments, the ramp angle is about 45 degrees. In some embodiments, the ramp angle is less than about 85 degrees, less than about 80 degrees, less than about 75 degrees, less than about 70 degrees, less than about 65 degrees, less than about 60 degrees, less than about 55 degrees, less than about 50 degrees, less than about 45 degrees, less than about 40 degrees, less than about 35 degrees, less than about 30 degrees, less than about 25 degrees, less than about 20 degrees, less than about 15 degrees, or less than about 10 degrees. In some embodiment, the ramp angle is in the range of between about 20-60 degrees, between about 22-58 degrees, between about 24-56 degrees, between about 26-54 degrees, between about 28-52 degrees, between about 30-50 degrees, between about 32-48 degrees, between about 34-46 degrees, between about 36-44 degrees, or between about 38-42 degrees.

Figure 14A:
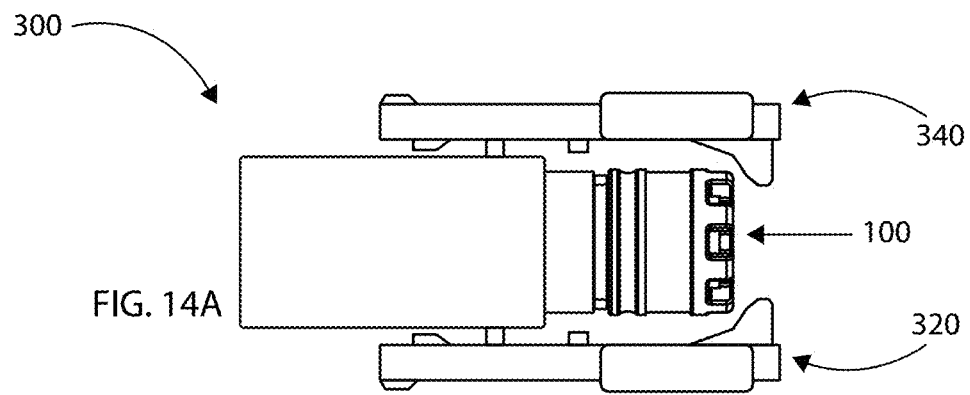
FIGS. 14A-14C show various views of breather wing positions of an embodiment of a one piece breather.

FIG. 14A illustrates a sample capture cartridge 100 being loaded into an embodiment of a one piece breather 300. In some embodiments, the first wing cartridge ejector 336 and the second wing cartridge ejector 356 may be simultaneously squeezes to bring the first wing cartridge ejector 336 and the second wing cartridge ejector 356 closer to the breather body 310 and provide space between the first wing ramp 332 and the second wing ramp 352 through which the sample capture cartridge 100 may pass. Once the sample capture cartridge 100 has passed the first wing ramp 332 and the second wing ramp 352, the pressure on the first wing cartridge ejector 336 and second wing cartridge ejector 356 may be release at which time the first wing second spring 328 and the second wing snap hole 358 may bias the first breather wing 320 and the second breather wing 340 such that the first wing ramp 332 and the second wing ramp 352 gently hold the sample capture cartridge 100 in place in the breather body cartridge port 316 (shown in both FIGS. 14A and 13B).

In some embodiments, the first breather wing 320 and the second breather wing 340 are configured to allow enough movement between the sample capture cartridge 100 and the breather body cartridge port 316 and/or the cartridge sealing grommet 302 (when present) that airflow is permitted around the sample capture cartridge 100. Thus, when a sample capture cartridge 100 is present and the first breather wing 320 and the second breather wing 340 are in their relaxed configurations (e.g., no external forces being applied), a sample fluid may enter the breather body inlet 312, pass through the breather body cartridge port 316 and flow around the sample capture cartridge 100, rather than being forced through the sample capture cartridge 100 (e.g., by exploiting the path of least resistance).

Figure 14B:
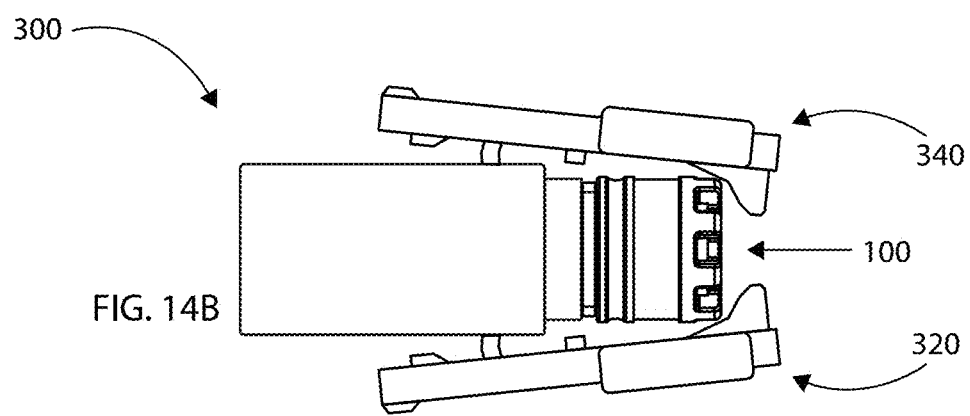

Turning to FIG. 14B, when an inward force is applied to the first breather wing 320 and the second breather wing 340, e.g., a force is applied to one or more of the first wing paddle 334 and the second wing paddle 354, the first wing ramp 332 and the second wing ramp 352 are brought closer to each other. As discussed herein, when the first wing ramp 332 and second wing ramp 352 are brought closer to each other, the ramps exert a downward/inward force on the sample capture cartridge 100, thereby pushing it towards or onto the breather body cartridge port 316 and/or cartridge sealing grommet 302 (when present). When the sample capture cartridge 100 is pressed onto/into the breather body cartridge port 316 and/or the cartridge sealing grommet 302, the base of the sample capture cartridge 100 may seal against the breather body cartridge port 316 and/or the cartridge sealing grommet 302, thereby forcing any sample fluid that is forced into the breather body inlet 312 to pass through the breather body inlet 312, through the breather body cartridge port 316, and through and out of the sample capture cartridge 100.

Figure 14C:
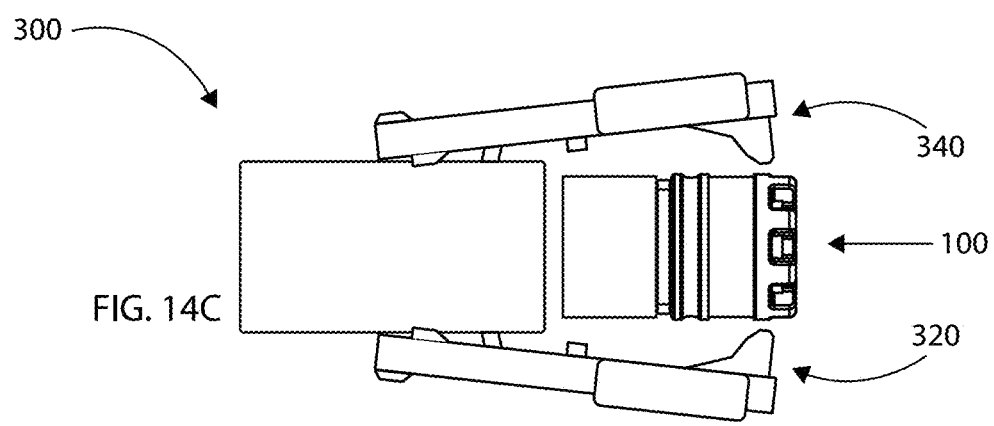

Turning to FIG. 14C, the first wing cartridge ejector 336 and second wing cartridge ejector 356 may be squeezes (e.g., brought closer to the breather body 310) to allow ejection of the sample capture cartridge 100. For example, after a sample is collected or if, for whatever reason, a user desires to ejection the sample capture cartridge 100, the first wing cartridge ejector 336 and second wing cartridge ejector 356 may be squeezed to cause the first wing ramp 332 and second wing ramp 352 to separate and allow passage of the sample capture cartridge 100 between the ramps.

In operation and to use the one piece breather 300, a user may squeeze the first wing cartridge ejector 336 and second wing cartridge ejector 356, compressing the first wing second spring 328 and the second wing second spring 348 and causing the distance between the first wing ramp 332 and the second wing ramp 352 to increase (e.g., causes the wings to open or flare). The user may then insert a sample collection cartridge, e.g., a sample capture cartridge 100, between the first wing ramp 332 of the first breather wing 320 and the second wing ramp 352 of the second breather wing 340. Once the sample collection cartridge has completely passed the ramps, the user may release (e.g., cease inward pressure or force on) the first wing cartridge ejector 336 and the second wing cartridge ejector 356. The first wing second spring 328 and the second wing second spring 348 will then bias the first breather wing 320 and the second breather wing 340 gently inward (e.g., so that the first wing ramp 332 and the second wing ramp 352 are gently biased toward each other) so that the sample capture cartridge 100 is held loosely in the breather body cartridge port 316 between the two wings, first breather wing 320 and second breather wing 340. The user may cause a flow of sample fluid to enter into the breather body inlet 312 of the one piece breather 300. However, as discussed above, before pressure is applied to the second wing paddle 354 of the second breather wing 340 and the first wing paddle 334 of the first breather wing 320 the sample fluid will flow between the breather body cartridge port 316 and the loosely-held sample capture cartridge 100. When the user is ready to collect a portion of the sample using the sample capture cartridge 100, the user may apply a force to the first wing paddle 334 of the first breather wing 320 and the second wing paddle 354 of the second breather wing 340 (e.g., the user may squeeze the two paddles with her fingers). As discussed herein, when the user squeezes the paddles, the first wing ramp 332 and the second wing ramp 352 will force the sample capture cartridge 100 toward and against the breather body cartridge port 316 and/or the cartridge sealing grommet 302, thereby sealing the sample capture cartridge 100 against the breather body cartridge port 316 and/or the cartridge sealing grommet 302 and forcing the sample to pass through the sample capture cartridge 100. In this way, a user may be able to segment a sample (e.g., the user may blow into the breather body inlet 312 then, partially through the breath, the user may squeeze the paddles to begin collection of a desired breath segment, e.g., a deep alveolar sample). Once the collection is complete, the user may squeeze (e.g., apply a force to or on) the first wing cartridge ejector 336 and the second wing cartridge ejector 356, thereby biasing the first wing ramp 332 and the second wing ramp 352 apart, e.g., away from each other, so that the sample capture cartridge 100 might pass through the ramps and be removed from the one piece breather 300, e.g., as shown in FIG. 14C. Finally, the one piece breather 300 may be discarded (though this is not necessary).

Rapid Test Sample Collection Cartridge

A number of separable sample collection cartridges and sample collection whistles (sample collection cartridge holders) are disclosed herein. As discussed, to use some of these separable systems, the sample collection cartridge may be inserted into the sample collection whistle, a sample fluid may be forced through the sample collection whistle (e.g., holder) and the sample collection cartridge, the sample collection cartridge removed from the sample collection whistle, and the collected sample evaluated. In some embodiments, it may be advantageous to use a rapid test sample collection cartridge that eliminates one or more steps needed to use the separable system. For example, in some instances sample segmentation may not be particularly important. Rather, the mere presence and/or identification of an analyte of interest, irrespective of time, may be the primary objective. Moreover, the speed of detection may be a primary objective. Additionally, it may be advantageous to entirely eliminate the collection whistle. For example, point of care testers may need a binary test (present/not present, or positive/negative) that they may use quickly and/or with young, inexperienced, or difficult patients. In such cases, a cartridge holder such as the sample collection whistle 200 may prove too complex and/or time consuming. In such cases a rapid test sample collection cartridge may advantageously be used.

Figure 15A:
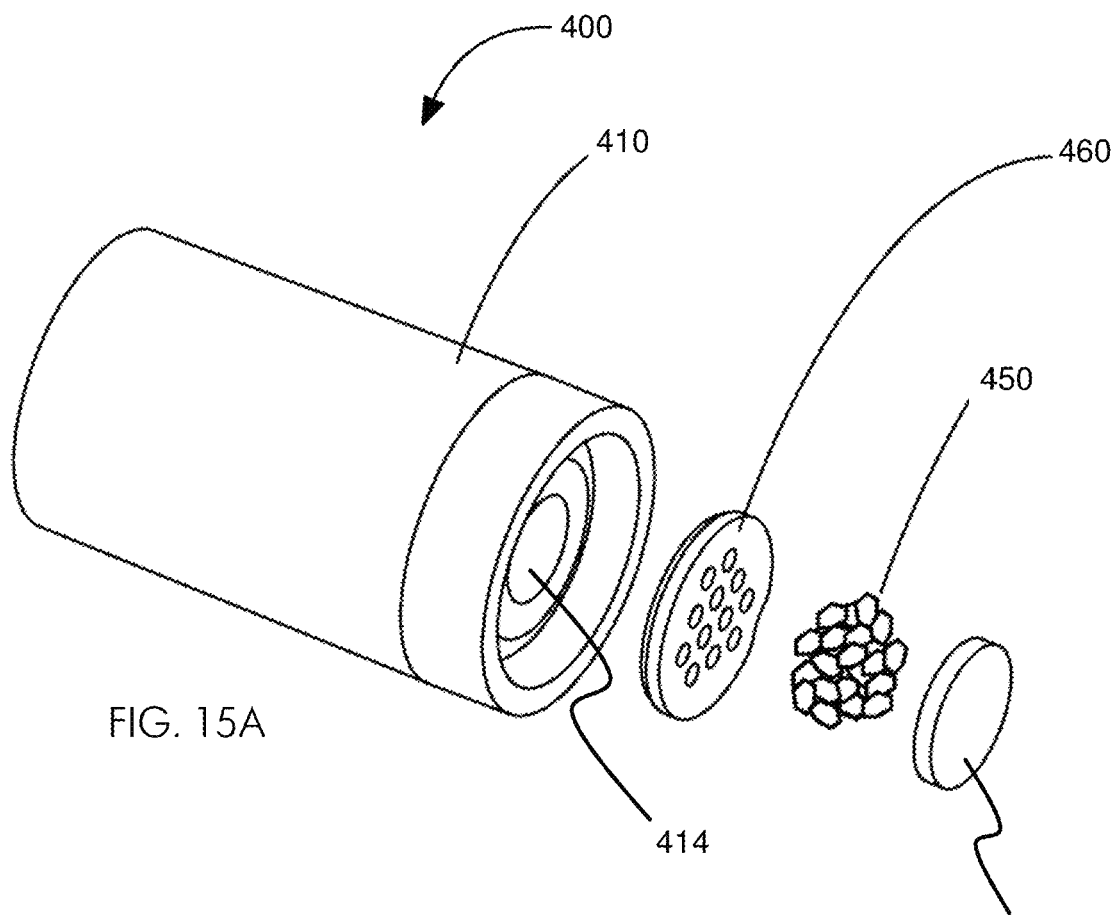
FIG. 15A shows an exploded view of an embodiment of a rapid test sample collection cartridge.

A rapid test sample collection cartridge 400 may include a collection cartridge body 410. As shown in FIG. 15A, the collection cartridge body 410 may be similar to the breather body 310 of the one piece breather 300, except without the wings first breather wing 320 and second breather wing 340. The collection cartridge body 410 may also be a hollow body with a collection cartridge body port 416 through which a fluid sample may be passed. Unlike the breather body 310 of the one piece breather 300, the collection cartridge body 410 of the rapid test sample collection cartridge 400 is not configured to accept and/or hold a sample collection cartridge. The collection cartridge body 410 of the rapid test sample collection cartridge 400 may include a sample collection portion build directly into the collection cartridge body 410. The rapid test sample collection cartridge 400 is similar to an integral combination of a one piece breather 300 and a sample capture cartridge 100.

In some embodiments, the collection cartridge body 410 may have a cross-sectional diameter that renders the rapid test sample collection cartridge 400 hand held. For example the collection cartridge body 410 may have a cross-sectional diameter of between about 5-30 mm, between about 5.5-28 mm, between about 6-26 mm, between about 6.5-24 mm, between about 7-22 mm, between about 7.5-20 mm, between about 8-18 mm, between about 8.5-16 mm, between about 9-14 mm, between about 9.5-12 mm, or any other diameter that advantageously facilitates use and collection of samples as disclosed herein. The rapid test sample collection cartridge 400 may have a length that renders the rapid test sample collection cartridge 400 easy to hold, manipulate, use, etc. For example the rapid test sample collection cartridge 400 has a length of about 30 mm. In some embodiments, the rapid test sample collection cartridge 400 has a length of between about 10-100 mm, between about 15-90 mm, between about 20-80 mm, between about 25-70 mm, between about 30-60 mm, between about 35-50 mm, or any other length that advantageously facilitates use and collection of samples as disclosed herein.

Figure 15B:
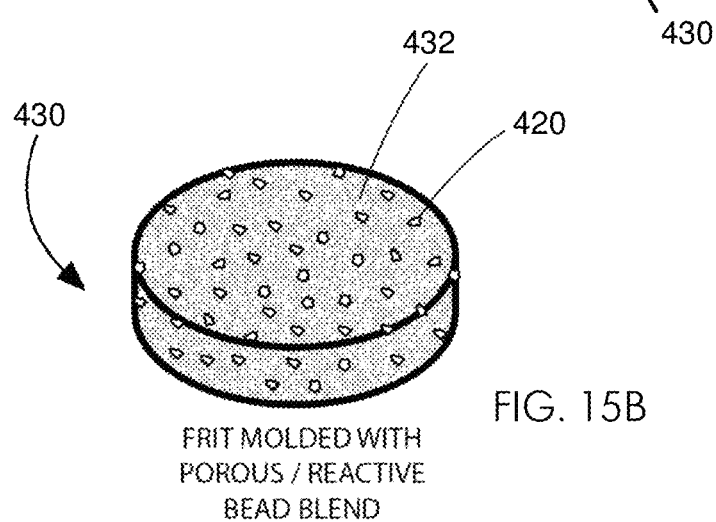
FIG. 15B shows a sample collection frit that may be used in conjunction with the rapid test sample collection cartridge of FIG. 15A.

The collection cartridge body 410 may include a sample collection frit 430 that is configured to pass the sample fluid while collecting an analyte of interest. In some embodiments, the sample collection frit 430 is similar to the blended bowl discussed herein. As shown in FIG. 15B, and as discussed in connection with the blended bowl, the sample collection frit 430 may comprise a porous base material 432 holding functionalized silica beads 420. When the analyte of interest passes through the porous base material 432 of the sample collection frit 430, it interacts with, e.g., passes by or contacts, the functionalized silica beads 420 and some of the analyte of interest binds with the silica 420. The binding of the analyte of interest with the functionalized silica beads 420 is a reaction that may be detected, e.g., at the time of reaction or later (such as using a developer solution). In some embodiments, the reaction of the analyte of interest with the functionalized silica beads 420 is analyzed using an optical analyzer, e.g., the reaction produces a change in the sample collection frit 430 that may be detected optically (such as color).

The rapid test sample collection cartridge 400 may also include a cartridge desiccant retainer 460 and or desiccant 450. In some embodiments the cartridge desiccant retainer 460 is similar in structure and function to the cartridge desiccant retainer 160 of the sample capture cartridge 100 (e.g., the cartridge desiccant retainer 460 may have: ports similar to the desiccant retainer ports 164 of the cartridge desiccant retainer 160; a notch similar to the desiccant retainer notch 162 of the cartridge desiccant retainer 160; and/or a bevel similar to the desiccant retainer bevel 166 of the cartridge desiccant retainer 160). In much the same way, the desiccant 450 may be similar in one or more metrics (e.g., size, quantity, positioning, function, etc.) to the desiccant 150 of the sample capture cartridge 100. In some embodiments, not shown, the rapid test sample collection cartridge 400 does not include either a cartridge desiccant retainer 460 or a desiccant 450. In some embodiments, the rapid test sample collection cartridge 400 has two cartridge desiccant retainers 460 between which the desiccant 450 is sandwiched, e.g., the collection cartridge body 410 holds a first cartridge desiccant retainer 460, then a quantity of desiccant 450, then a second cartridge desiccant retainer 460, then the sample collection frit 430 containing the functionalized silica beads 420. In some embodiments, the rapid test sample collection cartridge 400 has only one cartridge desiccant retainer 460, but no desiccant 450. In such embodiments, the cartridge desiccant retainer 460 may advantageously be provided as support for a comparatively think sample collection frit 430.

Figure 16A:
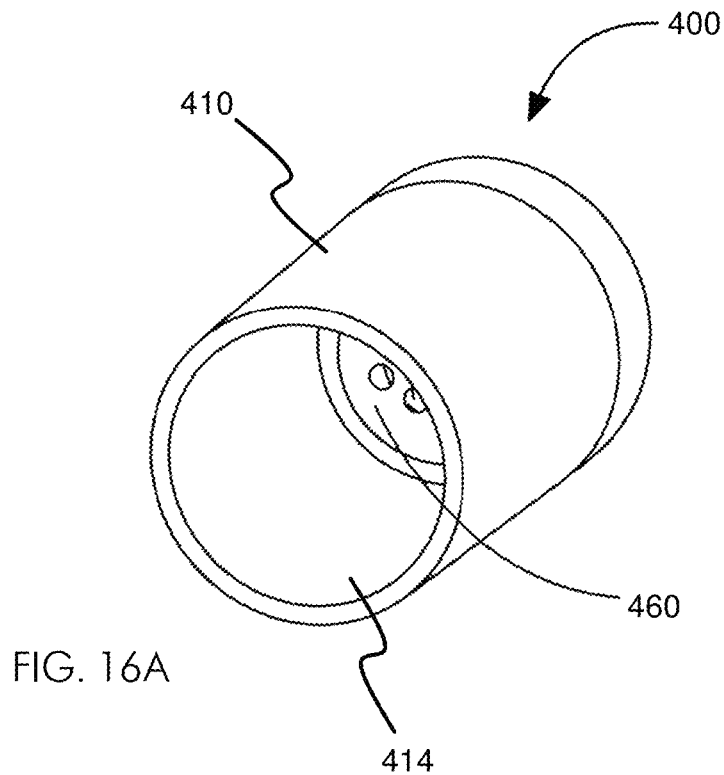
FIGS. 16A-16B show various views of a rapid test sample collection cartridge.
Figure 16B:
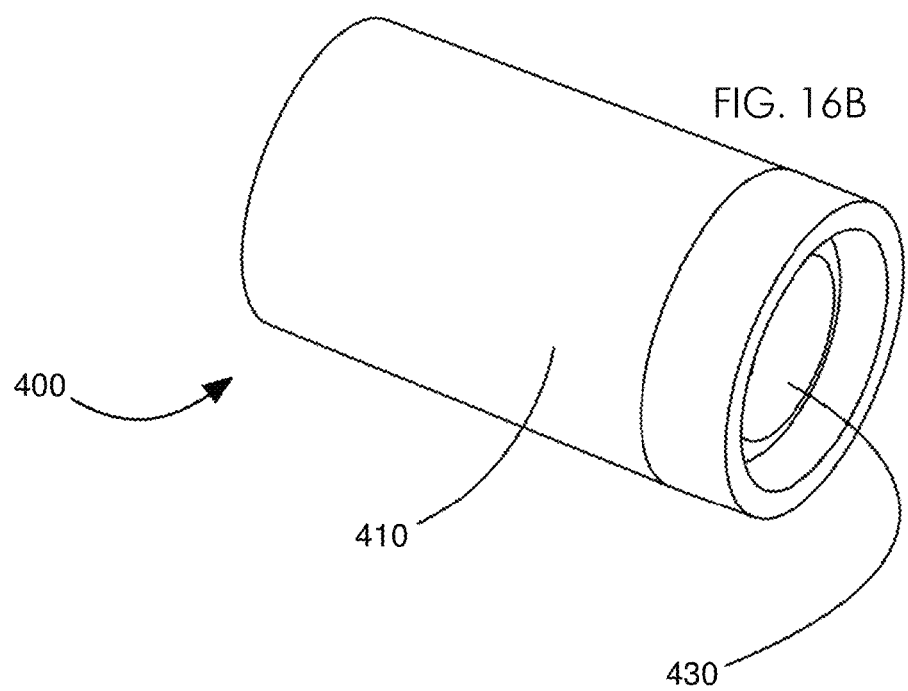

FIG. 16A-16B illustrate an embodiment of a rapid test sample collection cartridge 400. The rapid test sample collection cartridge 400 of FIGS. 16A-16B includes a collection cartridge body 410 having a collection cartridge body inlet 414 at a proximal or first end of the collection cartridge body 410. At the distal or second end (e.g., opposite the first end) of the collection cartridge body 410, the collection cartridge body 410 holds a cartridge desiccant retainer 460, as can be seen in FIG. 16A. With reference to FIG. 16B, the collection cartridge body 410 holds a sample collection frit 430 on its distal end. Between the sample collection frit 430 and the cartridge desiccant retainer 460, not shown in either FIG. 16A or 16B, the collection cartridge body 410 holds a quantity of desiccant 450 to absorb excess moisture from a fluid sample passed through the rapid test sample collection cartridge 400.

The rapid test sample collection cartridge 400 may be used to quickly and easily collect a fluid sample, e.g., a breath sample. In operation, a subject may be instructed to blow through the rapid test sample collection cartridge 400. The subject's breath will therefore be forced into the collection cartridge body inlet 414, and through the interior of the collection cartridge body 410, through any cartridge desiccant retainer(s) 460 and desiccant 450 present, and through the sample collection frit 430. The lid 702 and the base 704 may be closed to prevent the developer contained within the developer pad 710 from drying out when the developer pad 710 is not in use.

The rapid test sample collection cartridge 400 may be used with a rapid developer stamp pad 700, e.g., when a developing solution is needed or useful to detect (e.g., to induce a detectable change, such as an optically detectable change) the binding of the analyte of interest to the functionalized silica beads 420. The rapid developer stamp pad 700 may include at least a lid 702 and a base 704 which contain a developer pad 710. The developer pad 710 may be similar in structure and function to an ink pad, e.g., it may comprise a sponge or solution holding pad that contains a volume of a developer (an appropriate developer that is configured to induce a detectable change, such as an optically detectable change, in the sample collection frit 430 when/after an analyte of interest has bound to the functionalized silica beads 420).

Figure 17A:
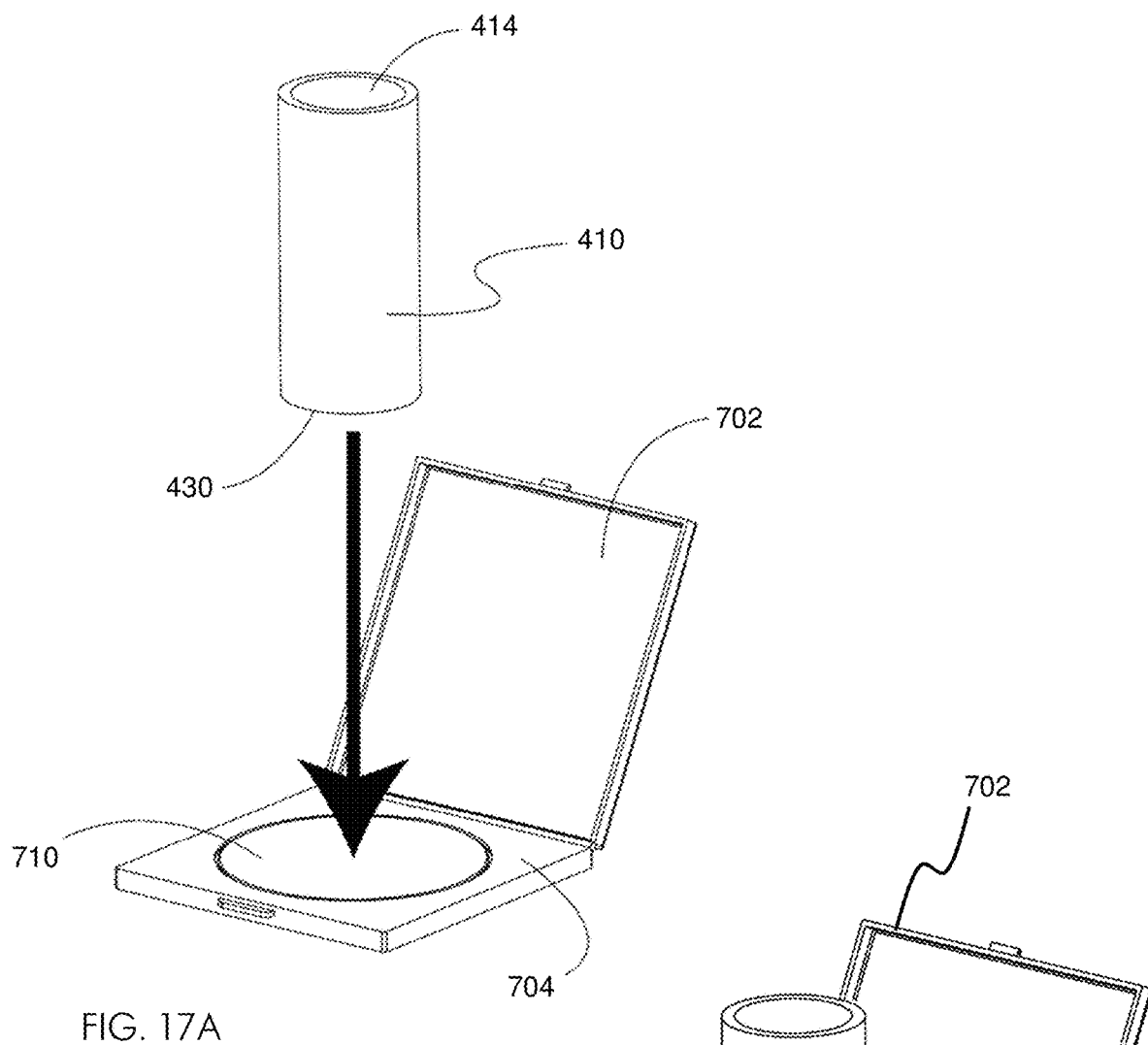
FIGS. 17A-17B show select steps in an embodiment of a method of using a rapid test sample collection cartridge.
Figure 17B:
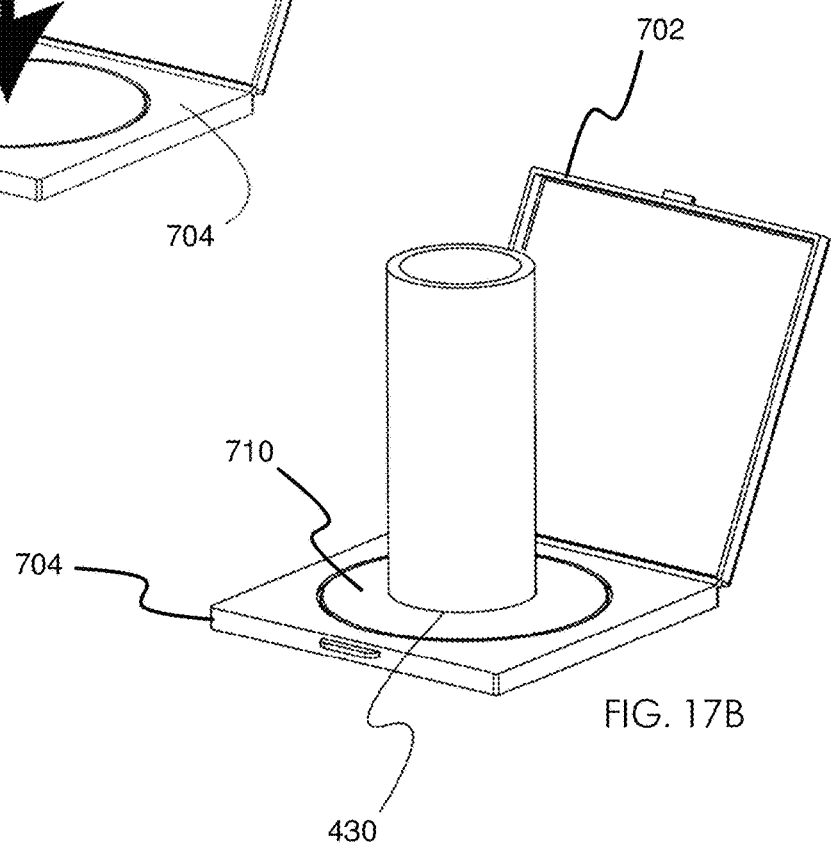
Figure 19A:
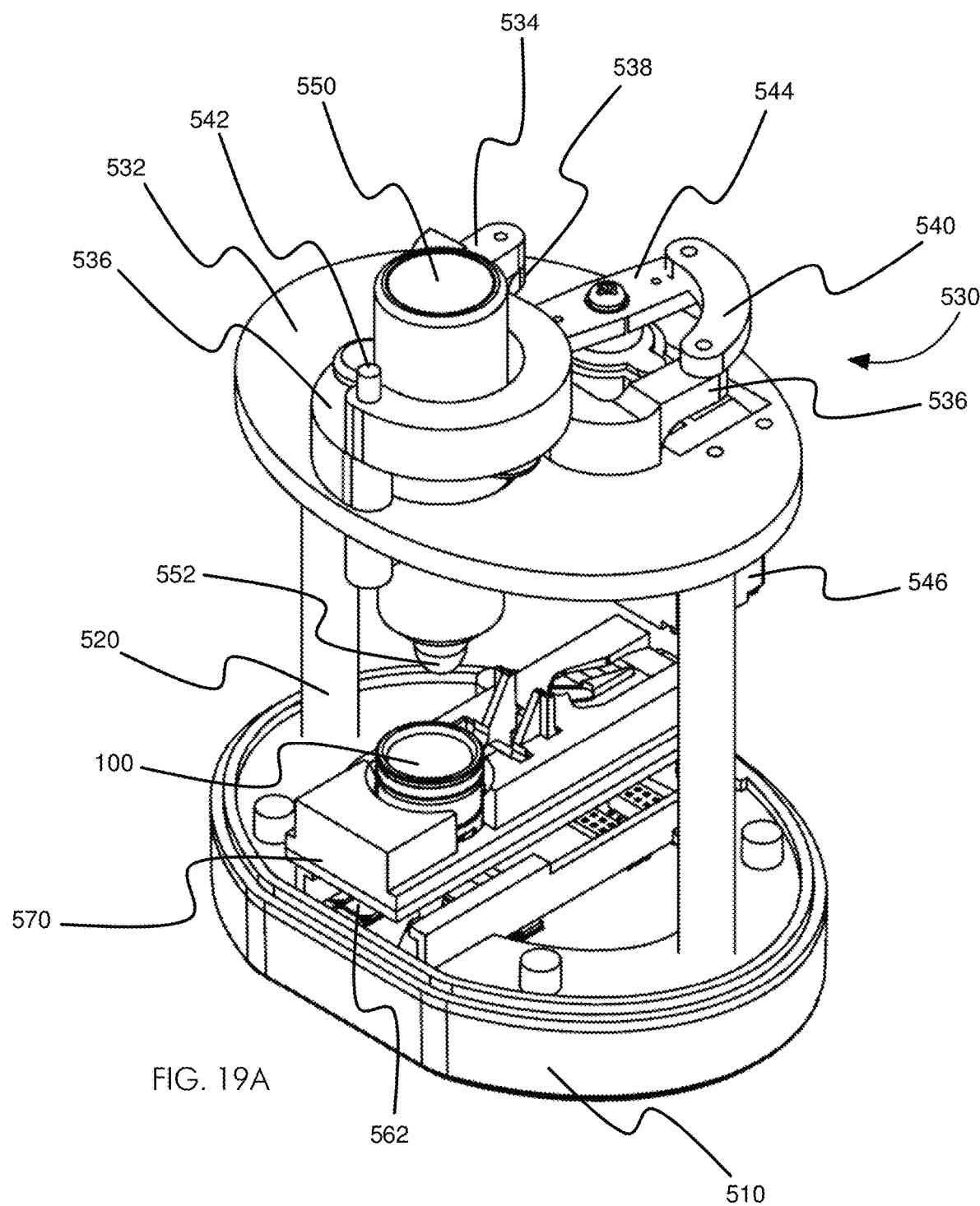
FIGS. 19A-19C show various view of the internal components of an embodiment of a base unit.
Figure 19B:
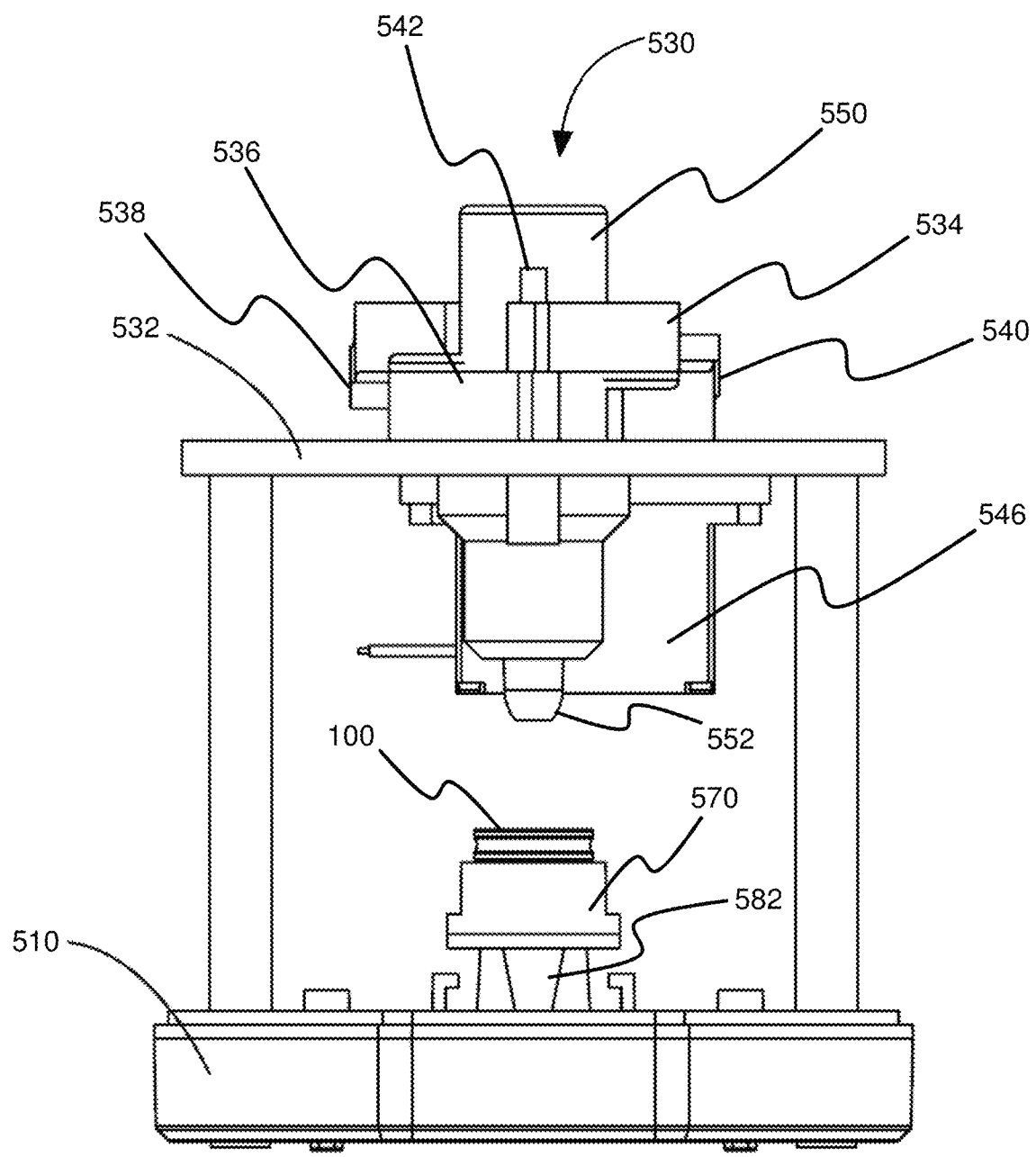
Figure 19C:
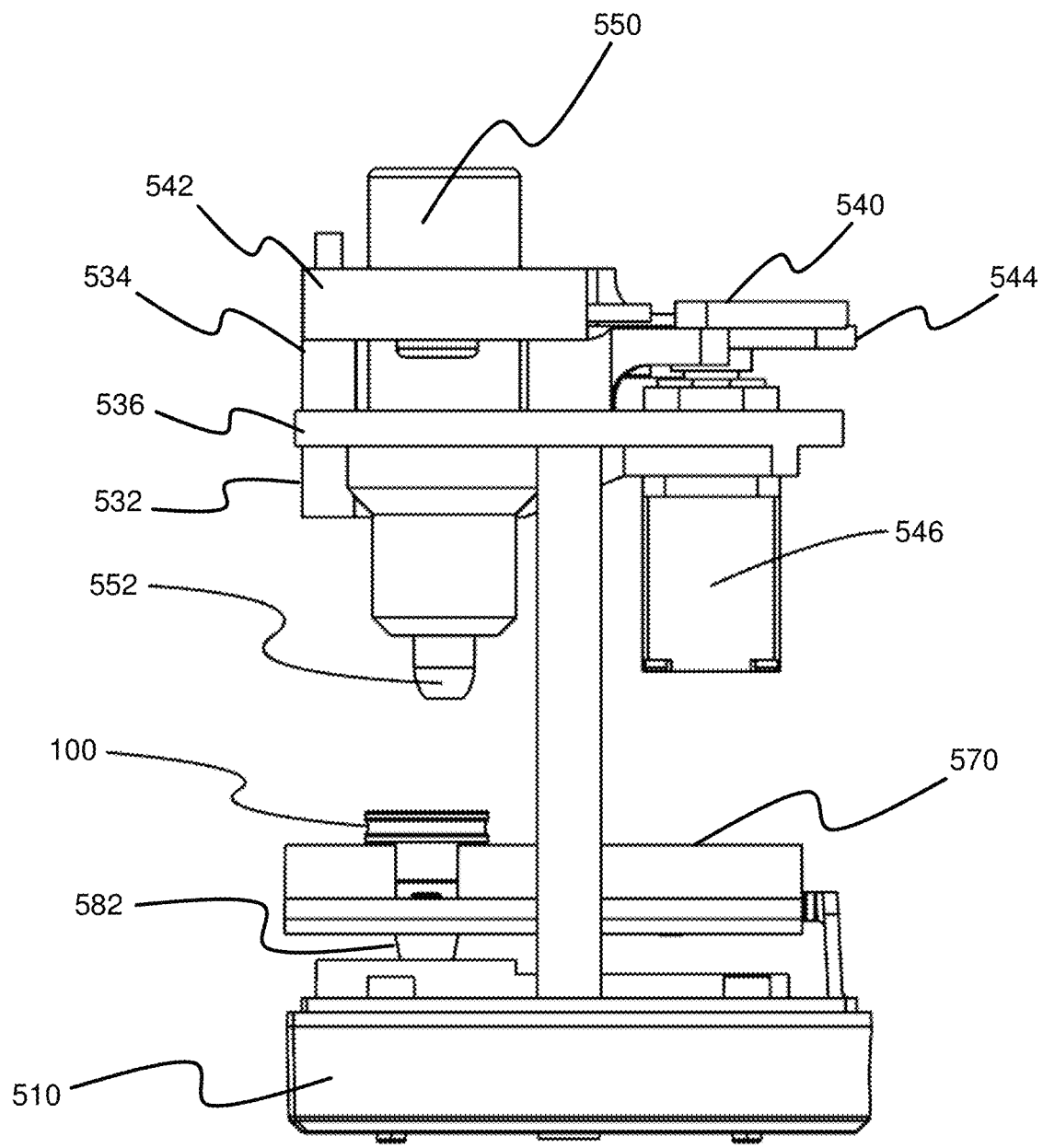

As shown in FIGS. 17A and 17B, after a sample has been collected, the rapid developer stamp pad 700 may be used in conjunction with the used rapid test sample collection cartridge 400 to analyze the sample. As shown in FIG. 17A, the rapid test sample collection cartridge 400 is lowered down onto the developer pad 710 of the rapid developer stamp pad 700, e.g., manually lowered. As will be readily understood, so that the sample collection frit 430, which presumably bound some concentration or amount of the analyte of interest (e.g., onto the functionalized silica beads 420) should be facing the developer pad 710 and the collection cartridge body inlet 414 pointing away from the 710. As shown in FIG. 17B, sample collection frit 430 of the used rapid test sample collection cartridge 400 may be pushed into the developer pad 710 of the rapid developer stamp pad 700. When the sample collection frit 430 of the rapid test sample collection cartridge 400 is pushed into the developer pad 710, the developer contained within the developer pad 710 enters into the porous body of the sample collection frit 430 and reacts/interacts with the sample collection frit 430 and the analyte of interest contained therein (e.g., the analyte of interest bound to the functionalized silica beads 420). Upon removal of the sample collection frit 430 of the rapid test sample collection cartridge 400 from the developer pad 710 of the rapid developer stamp pad 700, the developer may induce a detectable change, such as an optically, thermally, etc. detectable change, in the sample collection frit 430. The change in the sample collection frit 430, e.g., the optically detectable change, may be analyzed to determine the presence or absence of the analyte of interest within the sample collection frit 430 of the rapid test sample collection cartridge 400.

Base Unit

FIGS. 18A-18E illustrate various views of an embodiment of a base unit that may be used to analyze samples collected in sample capture cartridges as disclosed herein. In some embodiments, the various sample collection whistles disclosed herein may be used remotely from the base unit, and sample collection cartridges may be analyzed after collecting the samples when the user brings the sample collection cartridge to the base unit. FIG. 18A shows a top-biased front three-quarters view of an embodiment of a base unit. FIG. 18B shows a side view of an embodiment of a base unit. FIG. 18C shows a front view of an embodiment of a base unit. FIG. 18D shows a top view of an embodiment of a base unit. FIG. 18E shows a top-biased front three-quarters view of an embodiment of a base unit having a cartridge tray in an extended position. As shown in FIGS. 18A-18E, the base unit 500 may include a housing lower 510, housing middle 512, housing upper 514, and a cartridge tray 570. The cartridge tray 570 of the base unit 500 may be configured to accept and hold a sample capture cartridge 100, as shown in FIG. 18E.

FIG. 19A-21C show select internal components of the base unit 500 of FIGS. 18A-18E.

Figure 22A:
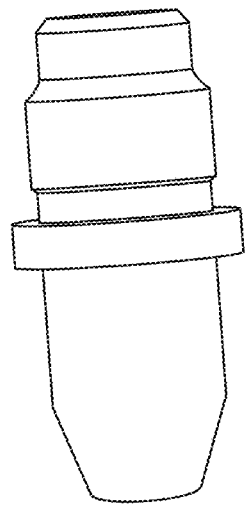
FIGS. 22A-22C show various views of an embodiment of a drip-resistant dropper tip.
Figure 22B:
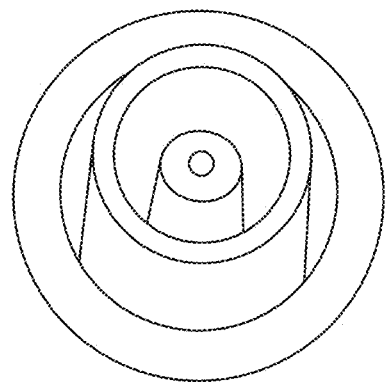
Figure 22C:
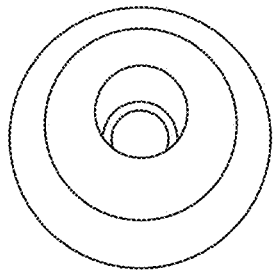

FIGS. 22A-22C illustrate various views of an embodiment of a dropper tip that may be used in connection with various developer solution bottles to control the drop size produced during dispensing of the developer solution.

Figure 23A:
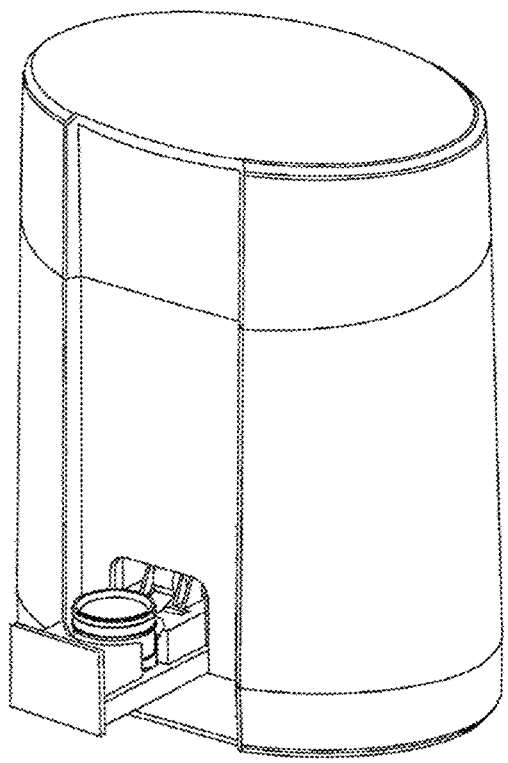
FIG. 23A shows a top-biased front three-quarters view of an embodiment of a base unit having a cartridge tray in an extended position.
Figure 23B:
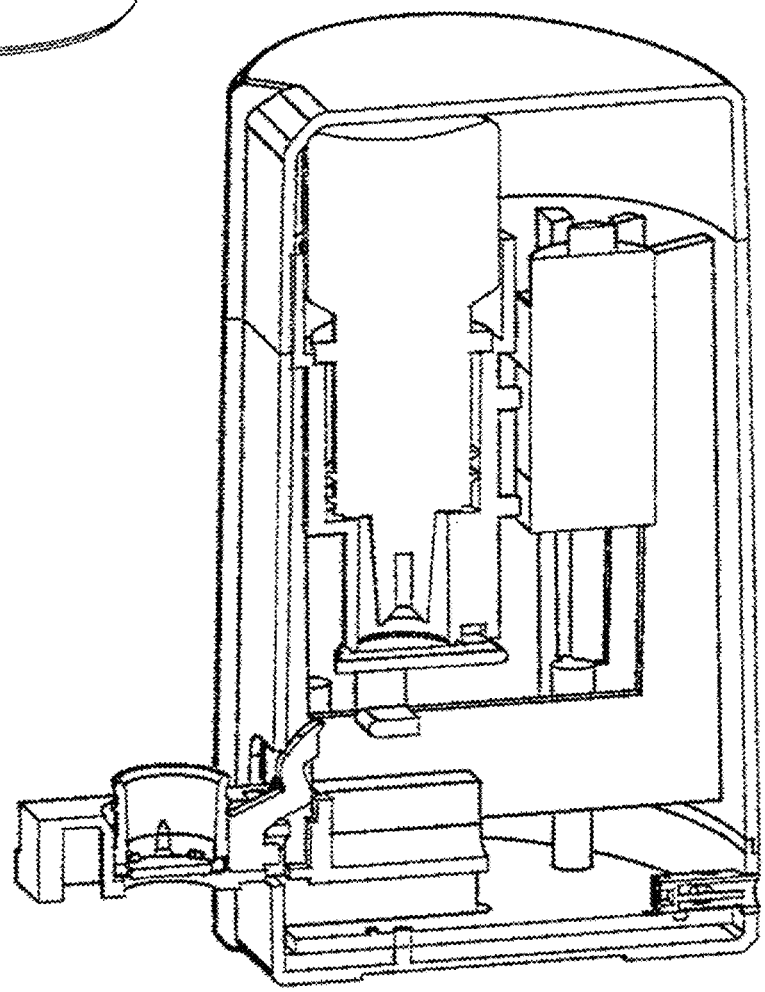
FIG. 23B shows a side cut-away view of an embodiment of a base unit having a cartridge tray in an extended position.

FIGS. 23A-23B show various views of a sample capture cartridge 100 loaded in a base unit.

Figure 24A:
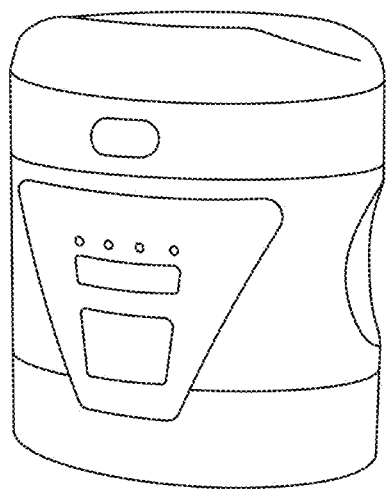
FIGS. 24A-24C show various views of an embodiment of a base unit.
Figure 24B:
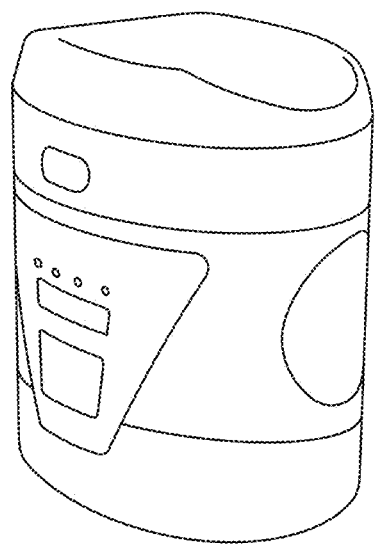
Figure 24C:
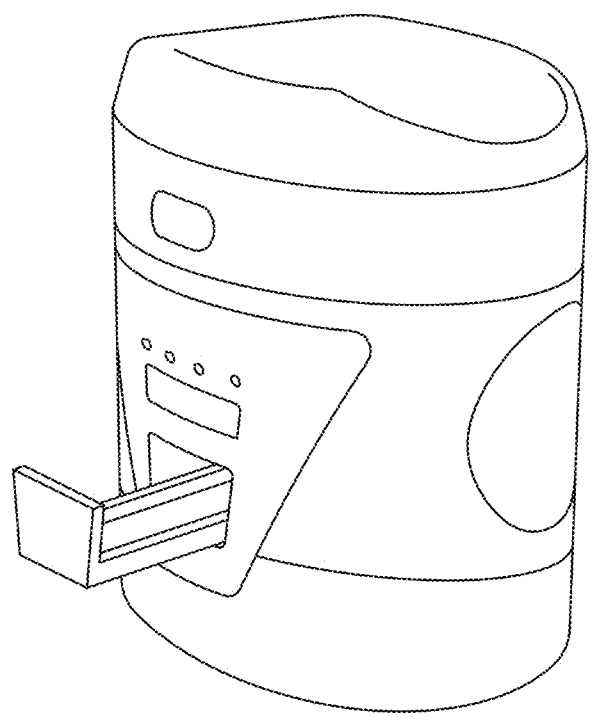

FIGS. 24A-24B illustrate various view of an embodiment of a base unit that may be used to analyze samples collected in sample capture cartridges as disclosed herein.

Figure 25:
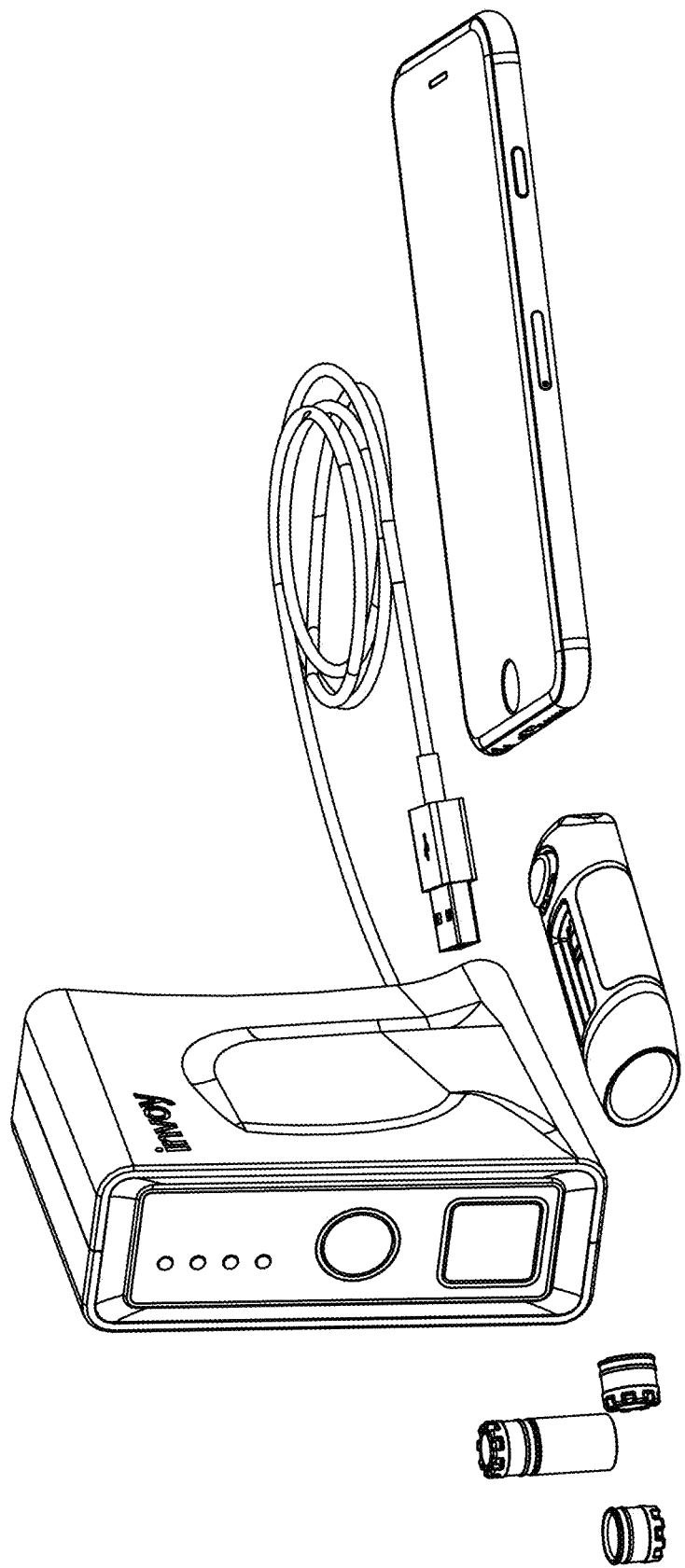
FIG. 25 shows a system for collecting and analyzing a sample using a sample capture cartridge, a sample collection whistle, a base unit, and a mobile phone.

FIG. 25 illustrates a system that may be used to capture and analyze (among other potential actions) a breath sample. The system includes a mobile device, e.g., an iPhone, a sample collection whistle, and a base unit.

Figure 32A:
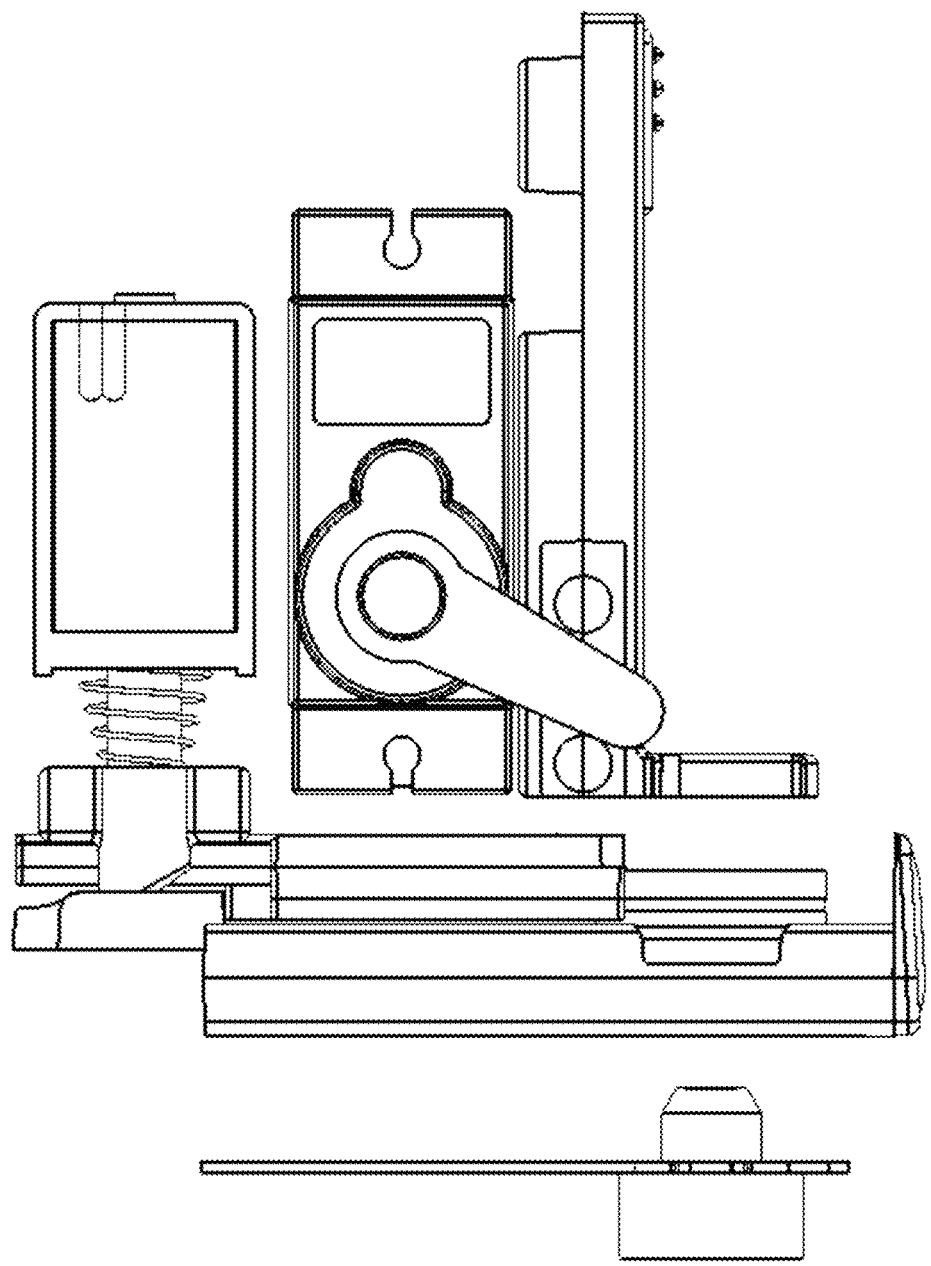
FIGS. 32A-32C show various view of various internal components of a base unit.
Figure 32B:
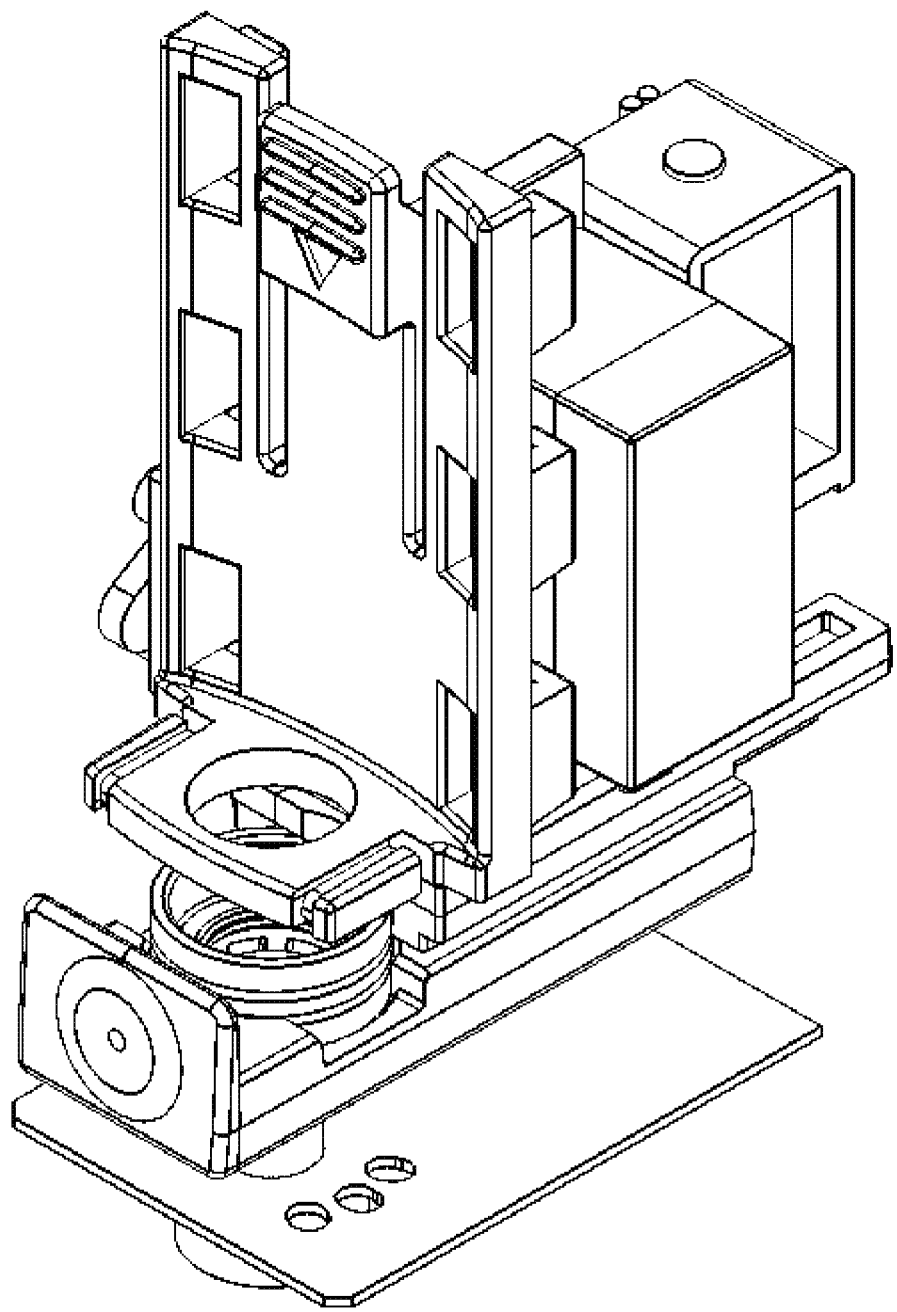
Figure 32C:
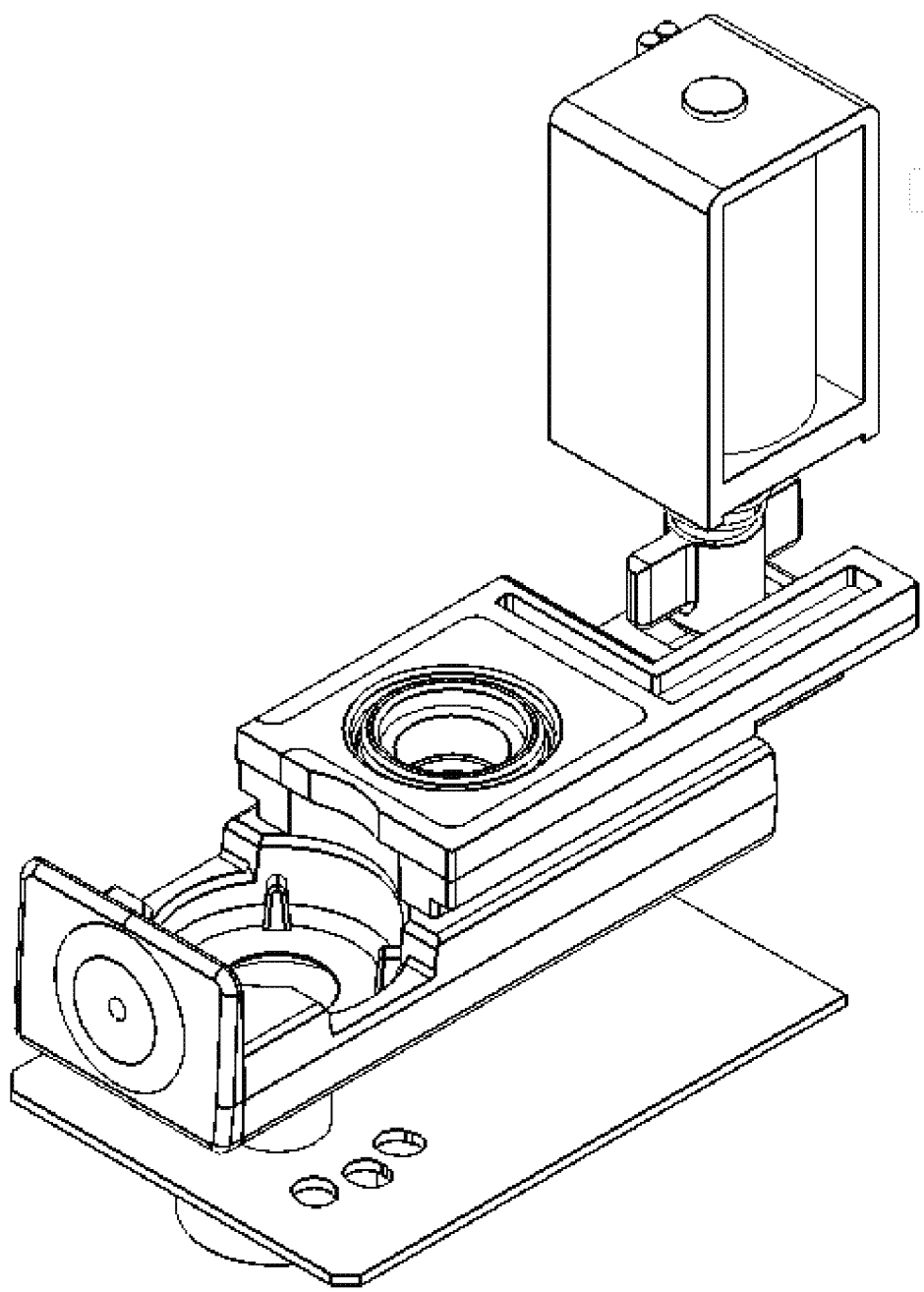

FIGS. 31A-31E illustrate various view of an embodiment of a base unit that may be used to analyze samples collected in sample capture cartridges as disclosed herein. FIG. 31A shows the base unit from a top-front biased three-quarters view. FIG. 31B shows the base unit from the front. FIG. 31C shows the base unit from the back. FIG. 31D shows the base unit from the right. FIG. 31E shows the base unit from the left. FIG. 32A-32C show select internal components of the base unit of FIGS. 31A-31E.

In some embodiments, the base unit is configured to hold and store a developer solution for use in analyzing samples collected in sample capture cartridges. The base unit may be further configured to accept a used sample capture cartridge 100 in a tray, which can be withdrawn into the body of the base unit. The body of the base unit may be substantially sealed from light pollution as some developer solutions may be light sensitive. The base unit may be further configured to dispense a set volume of developer solution into the used sample capture cartridge 100 then to analyze the developed sample using a light source and detector pair.

In some embodiments, the base unit holds a developer tank containing the developer solution. In some embodiments, the base unit dispenses developer solution from the developer tank using, at least partially, gravity. As such, some embodiments of the base unit may be sensitive to gravity (e.g., if the base unit is not vertical or substantially vertical, the developer solution may not dispense properly or at all). To address any sensitivity to gravity, some embodiments of the base unit may include a tilt sensor, e.g., an accelerometer, configured to detect when the base unit is impermissibly tilted. For example, the title sensor may be configured to disable the base unit (e.g., from performing a test analysis) when the base unit is tilted (e.g., off vertical) by more than about 1 degree, more than about 2 degrees, more than about 3 degrees, more than about 4 degrees, more than about 5 degrees, more than about 6 degrees, more than about 7 degrees, more than about 8 degrees, more than about 9 degrees, more than about 10 degrees, more than about 15 degrees, or more than about 20 degrees.

In some embodiments, the base unit includes a developer tank cover configured to cover the dispensing portion of the tank when not in use, such that the tank does not drip any developer solution on components of the base unit below it. The developer tank cover may be a sliding tray, spring-loaded from the rear, such that when no sample capture cartridge 100 is in the developer solution, the developer tank cover slides forward to cover the tip of the developer tank (the developer tank may be, for example, lowered into a cup on the developer tank cover when not in use). The developer tank cover may be configured such that when a sample capture cartridge 100 is placed in the base unit, e.g., a sliding tray in the base unit, for analysis, the sample capture cartridge 100 pushes the developer tank cover out of the way so that the developer tank may descend and dispense developer solution into the sample capture cartridge 100.

In some embodiments, the base unit is comparatively or relatively small, e.g., a hand-held, or a table-top, base unit. The base unit may be generally defined by a height (e.g., a dimension from the bottom of the base unit to the top of the base unit), a depth (e.g., a dimension from the front of the base unit to the back of the base unit), and a width (e.g., a dimension from a first side of the base unit to the other, opposite side of the base unit). In some embodiments, that height of the base unit is about 4.5 inches. In some embodiments, the height of the base unit is between about 1-12 inches, between about 1.5-11.5 inches, between about 2-11 inches, between about 2.5-10.5 inches, between about 3-10 inches, between about 3.5-9.5 inches, between about 4-9 inches, between about 4.5-8.5 inches, between about 5-8 inches, between about 5.5-7.5 inches, or between about 6-7 inches. In some embodiments, the height of the base unit is between about 3-30 inches, between about 4-25 inches, between about 5-20 inches, between about 6-15 inches, or between about 7-10 inches. In some embodiments, the depth of the base unit is about 4 inches. In some embodiments, the depth of the base unit is between about 1-10 inches, between about 1.5-9.5 inches, between about 2-9 inches, between about 2.5-8.5 inches, between about 3-8 inches, between about 3.5-7.5 inches, between about 4-7 inches, between about 4.5-6.5 inches, or between about 5-6 inches. In some embodiments, the depth of the base unit is between about 2-20 inches, between about 2.5-18 inches, between about 3-16 inches, between about 3.5-14 inches, between about 4-14 inches, between about 4.5-12 inches, between about 5-10 inches, between about 5.5-8 inches, or between about 6-7 inches. In some embodiments, the width of the base unit is about 2 inches. In some embodiments, the width of the base unit is between about 0.5-5 inches, between about 0.75-4.5 inches, between about 1-4 inches, between about 1.25-3.5 inches, between about 1.5-3.25 inches, between about 1.75-3 inches, or between about 2-2.75 inches. In some embodiments, the width of the base unit is between about 1-20 inches, between about 1.5-18 inches, between about 2-16 inches, between about 2.5-14 inches, between about 3-12 inches, between about 3.5-10 inches, between about 4-8 inches, or between about 4.5-6 inches.

Developer Tank

The developer tank held by the base unit may be a user-replaceable tank for holding a developer solution. In some embodiments, the solution that this tank is designed to house and dispense is a challenging liquid to manage. For example, in some embodiments, the developer solution is viscous. In some embodiments, the developer solution is light sensitive. In some embodiments, the developer solution produces a residue upon drying. In some embodiments, the developer solution has a lower boiling point. In some embodiments, the developer solution is flammable. In some embodiments, the developer solution may suffer from all of these limitations: it may be comparatively viscous, be flammable, have UV-light sensitivity, produce a crust-like residue (post dry-out), and/or have a low boiling point (which may cause pressurization or negative pressure within any rigid storage vessel). Developer tanks as disclosed herein address each of these specialized needs.

In some embodiments, the developer solution comprises dimethyl sulfoxide (DMSO), methanol, and sodium nitroprusside (SNP). Dimethyl sulfoxide is a viscous. Methanol is flammable. Sodium nitroprusside is light sensitive. In some embodiments, the developer solution comprises about 24 mL of dimethyl sulfoxide, about 120 mL of methanol, and about 4.8 g of sodium nitroprusside. However, other ratios may be used. Additionally, developer solutions containing or comprising entirely different ingredients or components may be used and/or dispensed from develop tanks as disclosed herein.

In some embodiments, the developer solution tank 3300 disclosed herein is configured to be used in a small, e.g., hand-held, or table-top, base unit. For example, in some embodiments, the developer solution tank 3300 has a volume (e.g., a volume of developer solution in a full developer solution tank 3300) of about 1.2 mL. In some embodiments, the developer solution tank 3300 has a maximum developer solution volume that is less than about 20 cc, less than about 18 cc, less than about 16 cc, less than about 14 cc, less than about 12 cc, less than about 10 cc, less than about 9 cc, less than about 8 cc, less than about 7 cc, less than about 6 cc, less than about 5 cc, less than about 4.5 cc, less than about 4 cc, less than about 3.5 cc, less than about 3 cc, less than about 2.5 cc, less than about 2 cc, less than about 1.75 cc, less than about 1.5 cc, less than about 1.25 cc, less than about 1 cc, less than about 0.9 cc, less than about 0.8 cc, less than about 0.7 cc, less than about 0.6 cc, or less than about 0.5 cc. In some embodiments, the developer solution tank 3300 has an end-to-end length of less than about 5 inches, less than about 4.5 inches, less than about 4 inches, less than about 3.5 inches, less than about 3 inches, less than about 2.5 inches, less than about 2 inches, less than about 1.5 inches, less than about 1 inch, or less than about 0.5 inches. In some embodiments the developer solution tank 3300 has a side-to-side width of less than about 4.5 inches, less than about 4 inches, less than about 3.5 inches, less than about 3 inches, less than about 2.5 inches, less than about 2 inches, less than about 1.5 inches, less than about 1 inch, or less than about 0.5 inches.

FIGS. 33A-33C show various views of an embodiment of a developer solution tank 3300. FIG. 33A shows a side view of the developer solution tank 3300. FIG. 33B shows a bottom-biased three-quarters view of the developer solution tank 3300. FIG. 33C shows a cross-sectional view of the developer solution tank 3300. The developer solution tank 3300 has a tank body top portion 3311, a tank body 3310, a tank body lower portion 3312, and a nozzle 3320. The tank body 3310, tank body lower portion 3312, and nozzle 3320 may be formed as a unitary part and the tank body top portion 3311 formed as a separate part and added to the developer solution tank 3300 after filling the developer solution tank 3300 with the developer solution. The connection between the tank body top portion 3311 may have a seal, e.g., an o-ring or other type of seal. In some embodiments, the tank body top portion 3311 is welded, e.g., ultrasonically welded to the tank body 3310.

With reference to FIG. 33B, the nozzle 3320 comprises various portions that move respect to the housing of the developer solution tank 3300, e.g., the nozzle housing 3322. The portions of the nozzle 3320 that move with respect to the nozzle housing 3322 include the dispenser tip 3332, which is connected to the connecting rod 3340, the dispenser tip o-ring 3331 surrounding the dispenser tip 3332, and the dispenser o-ring flange 3333 configured to hold the dispenser tip o-ring 3331 in place around the dispenser tip 3332.

In some embodiments, the nozzle recess 3321 is configured to catch small volumes of developer solution that are successfully deposited into a sample capture cartridge 100 during sample analysis. In addition, the nozzle recess 3321 may serve to hold and/or accumulate dried crusts from such excess developer solution that is not successfully deposited into a sample capture cartridge 100 during sample analysis.

With continued reference to FIG. 33B, the bleed valve 3350 comprises a bleed valve housing 3352 surrounding the connecting rod 3340 which has a bleed valve o-ring 3351 in a bleed valve o-ring recess 3353 near or proximal its upper end.

The connecting rod 3340 extend from the dispenser tip 3332 and the dispenser o-ring flange 3333 (which extend out of the dispenser valve 3330) all the way through and out of the bleed valve housing 3352 of the bleed valve 3350. The spring 3342 surrounds the connecting rod 3340 and is biased on its upper end against the bleed valve housing 3352, which is held stationary with respect to the rest of the developer solution tank 3300, and is biased on its lower end against the dispenser o-ring flange 3333, which is movable with respect to the housing of the developer solution tank 3300.

In some embodiments, the developer solution tank 3300 is configured to stabilize its own internal pressure prior to dispensing the liquid solution contained therein. In some embodiments, the developer solution tank 3300 is configured to dispense onto a surface that can aid in the dispensing process by wicking liquid from the dispenser valve 3330 of the nozzle 3320, e.g., a porous surface. In some embodiments the developer solution tank 3300 is configured to dispense onto a surface that does not wick liquid from the dispenser valve 3330 of the nozzle 3320.

In some embodiments, the developer solution tank 3300 is configured to sequentially dispense reproducible volumes of developer solution (e.g., similar volumes for sequential tests). In some embodiments, the developer solution tank 3300 is configured to dispense developer solution at a substantially constant flow rate (e.g., the volume of the developer solution dispensed may be determined based on the time the developer solution tank 3300 is dispensing. In some embodiments, the developer solution tank 3300 is configured to dispense about 60-70 µL per dispensing (e.g., this may be based on flow rate and time dispensing at a given, or variable, flow rate). In some embodiments, the developer solution tank is configured to dispense between about 10-300 µL, between about 15-280 µL, between about 20-260 µL, between about 25-240 µL, between about 30-220 µL, between about 35-200 µL, between about 40-180 µL, between about 45-160 µL, between about 50-140 µL, between about 55-120 µL, between about 60-100 µL, between about 65-80 µL, or between about 70-75 µL. In some embodiments, the developer solution tank 3300 has a substantially continuous and/or stable flow rate such that given a substantial time open or dispensing, the variance between subsequent dispensings is less than about 30 µL, less than about 29 µL, less than about 28 µL, less than about 27 µL, less than about 26 µL, less than about 25 µL, less than about 24 µL, less than about 23 µL, less than about 22 µL, less than about 21 µL, less than about 20 µL, less than about 19 µL, less than about 18 µL, less than about 17 µL, less than about 16 µL, less than about 15 µL, less than about 14 µL, less than about 13 µL, less than about 12 µL, less than about 11 µL, less than about 10 µL, less than about 9 µL, less than about 8 µL, less than about 7 µL, less than about 6 µL, less than about 5 pt, less than about 4 µL, less than about 3 µL, less than about 2 µL, or less than about 1 µL. In some embodiments, the developer solution tank 3300 increases in accuracy over time. The volumetric variance of each drop after the first few drops may be less than the volumetric variance of each drop for the first few drops. For example, the volumetric variance of each drop for the first few drops dispensed from the developer solution tank 3300 is about ±10 µL and the volumetric variance of each subsequent drop is about ±5 µL. In some embodiments, the volumetric variance of each drop for the first few drops (e.g., less than about 10, 9, 8, 7, 6, 5, 4, 3, 2, 1) is about ±20 µL, ±18 µL, ±16 µL, ±14 µL, ±12 µL, ±10 µL, ±8 µL, ±6 µL, ±4 µL, ±2 µL, and the volumetric variance of each subsequent drop is about ±18 µL, ±16 µL, ±14 µL, ±12 µL, ±10 µL, ±8 µL, ±6 µL, ±4 µL, ±2 µL, ±1 µL.

Figure 34A:
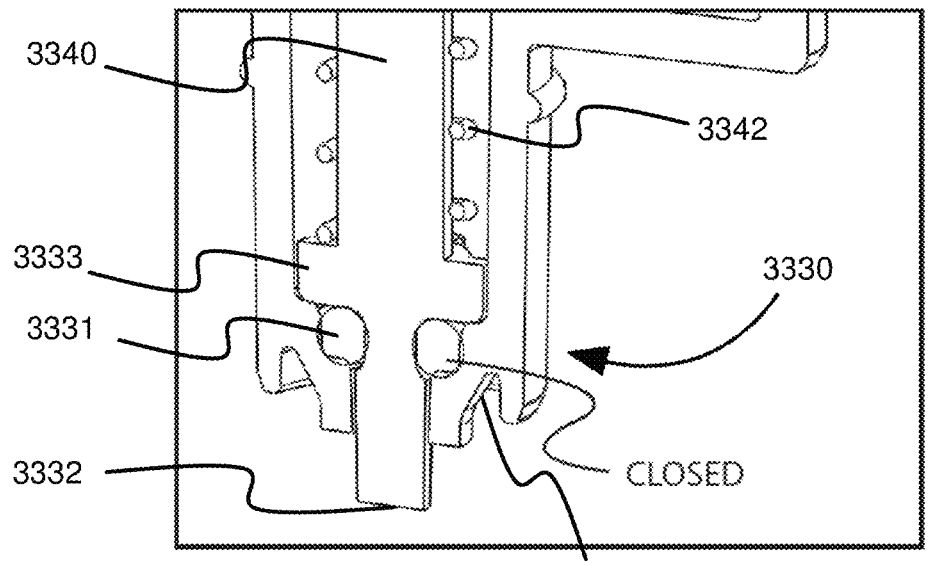
FIGS. 34A-34B show various views of an embodiment of a nozzle.
Figure 34B:
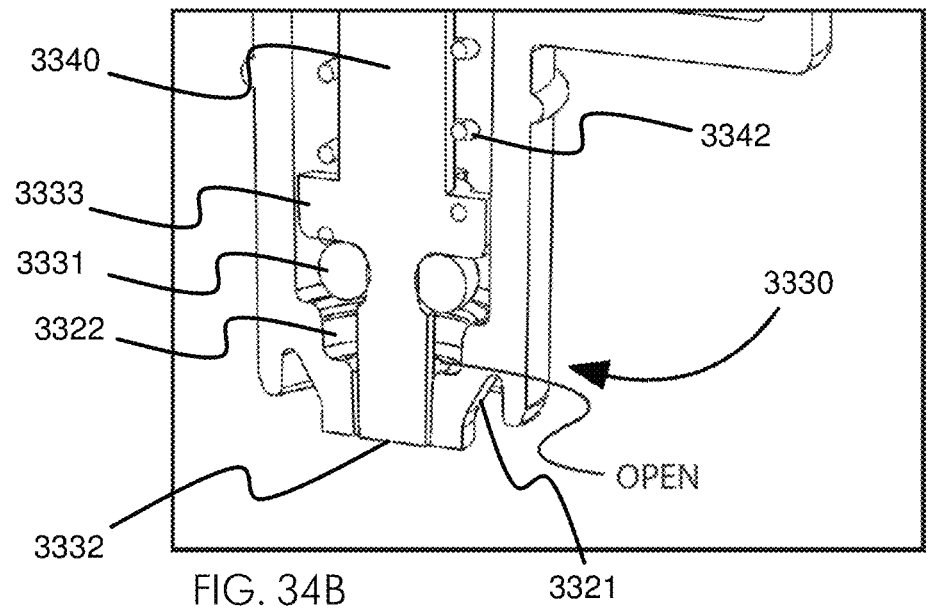

FIGS. 34A-34B illustrate enlarged views of the nozzle 3320 of the developer solution tank 3300. FIG. 34A shows the dispenser valve 3330 of the nozzle 3320 in a closed configuration. FIG. 34B shows the dispenser valve 3330 of the nozzle 3320 in an open configuration. At the lower end of the tank, e.g., at nozzle 3320, the small, cylindrical tip of the dispenser tip 3332 protrudes out of a hole in the dispenser valve 3330 of the nozzle 3320. In some embodiments, when closed the dispenser tip 3332 protrudes approximately 2.38 mm past the end of the nozzle 3320. In some embodiments, when closed the dispenser tip 3332 protrudes past the end of the nozzle 3320 by less than about 3 mm, less than about 4 mm, less than about 3.8 mm, less than about 3.6 mm, less than about 3.4 mm, less than about 3.2 mm, less than about 3 mm, less than about 2.8 mm, less than about 2.6 mm, less than about 2.4 mm, less than about 2.2 mm, less than about 2 mm, less than about 1.8 mm, less than about 1.6 mm, less than about 1.4 mm, less than about 1.2 mm, less than about 1 mm, or less than about 0.8 mm, When the dispenser valve 3330 of the nozzle 3320 is brought to a surface, such as porous polyethylene (such as may be used in connection with one or more embodiments of the porous bowl 130 disclosed herein), the dispenser tip 3332 is depressed. In some embodiments, the dispenser tip 3332 is depressed until the body of the nozzle 3320 touches the surface and the dispenser tip 3332 is telescopically pushed inside, e.g., completely inside, the body of the nozzle 3320, such as is shown in FIG. 34B.

As shown in FIG. 34C, the dispenser tip 3332 is backed by spring 3342, e.g., an internal compression return spring, that forces the dispenser tip 3332 back out of the nozzle 3320 when dispensing stops and the dispenser valve 3330 is withdrawn from the surface, e.g., the porous surface. When the dispenser tip 3332 is depressed, dispenser tip o-ring 3331 is unseated from within the nozzle housing 3322 and a flow path is opened to allow the liquid solution stored above to flow. In some embodiments, gravity facilitates or helps to promote flow of develop solution out of the dispenser valve 3330 of the nozzle 3320. In some embodiments, along with gravity, wicking by a porous surface, such as the porous surface of one or more porous bowls 130 disclosed herein, facilitates or helps to promote flow of develop solution out of the dispenser valve 3330 of the nozzle 3320. When dispensing stops, the tip travels back out of the dispenser valve 3330 of the nozzle 3320 and dispenser tip o-ring 3331 is reseated against the nozzle housing 3322 (e.g., when the spring 3342 pushes downward on the dispenser o-ring flange 3333, thereby blocking off the flow path, e.g., completely blocking off the flow path.

In some embodiments, the developer solution tank 3300 is a rigid tank. In a rigid tank, any volume of developer solution that is lost during dispensing must be replaced with air from the outside of the developer solution tank 3300. Bleed valve 3350, located at the top of the developer solution tank 3300, opposite the dispenser valve 3330 and nozzle 3320, is configured to allow this air to enter.

In some embodiments, the bleed valve 3350 opens and closes at specific times. In some embodiments, the bleed valve 3350 advantageously opens shortly before, e.g., a fraction of a second before, the dispenser valve 3330 of the nozzle 3320 opens. In some embodiments, a base unit configured to hold and/or move the developer solution tank 3300 includes a programmed controller that controls the movement of the developer solution tank 3300 as well as the opening and/or closing of the bleed valve 3350 and/or the dispenser valve 3330 or other automated tasks (such base unit may also include a wireless transceiver for communicating with a smartphone). In some embodiments, the bleed valve 3350 opens at the same time as, e.g., simultaneously with, the dispenser valve 3330 of the nozzle 3320 opens. In some embodiments, the bleed valve 3350 opens shortly after, e.g., a fraction of a second after, the dispenser valve 3330 of the nozzle 3320 opens. The relationship of the timing of the closure of the bleed valve 3350 of the timing of the closure of the dispenser valve 3330 may be controlled with the distance between the dispenser o-ring flange 3333 and the bleed valve o-ring recess 3353 on the connecting rod 3340 as well as the depth of the nozzle housing 3322 and the depth of the bleed valve housing 3352 (e.g., the distance that the o-ring of the respective structure may travel into the respective housing). As will be readily appreciated, the bleed valve 3350 may advantageously close when dispensing is complete to prevent evaporation of a volatile liquid contained within the developer solution tank 3300.

Figure 35A:
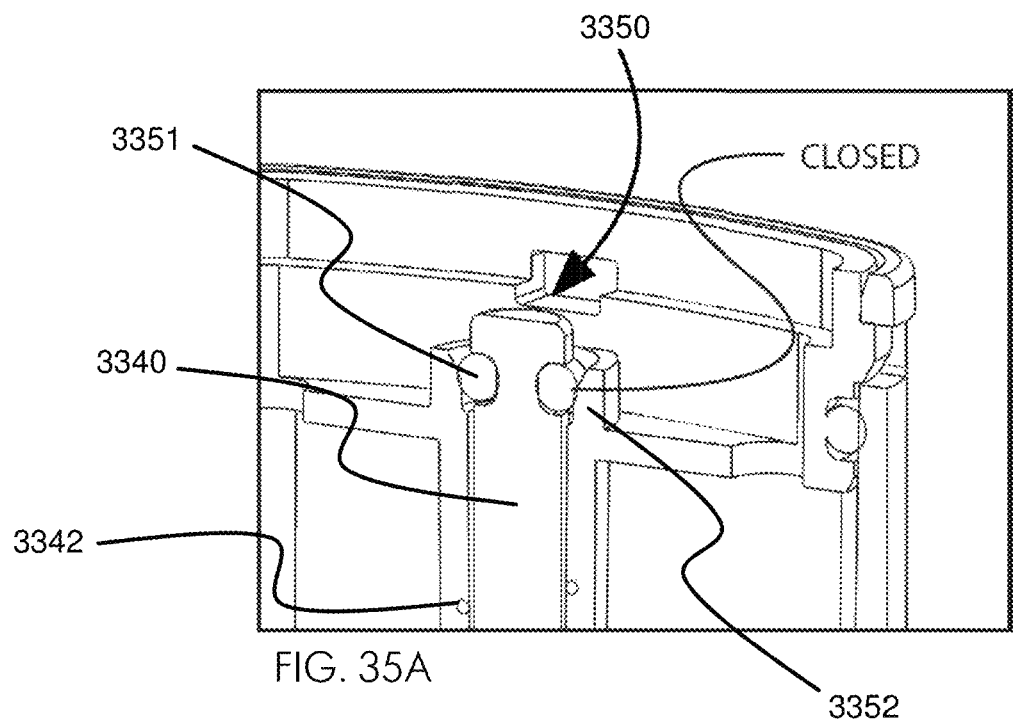
FIGS. 35A-35B show various views of an embodiment of a bleed valve.

FIG. 35A illustrates the bleed valve 3350 in a closed configuration. As shown, the bleed valve o-ring 3351 (nested within bleed valve o-ring recess 3353) is seated within the bleed valve housing 3352 (note that the bleed valve o-ring recess 3353 may be forcibly seated against the bleed valve housing 3352 as spring 3342 pushes down on the dispenser o-ring flange 3333 fixed to the connecting rod 3340). The closed configuration of the bleed valve 3350 shown in FIG. 35A advantageously prevents evaporation of the developer solution between dispensings: this is particularly important when a low boiling point developer solution is being used.

Figure 35B:
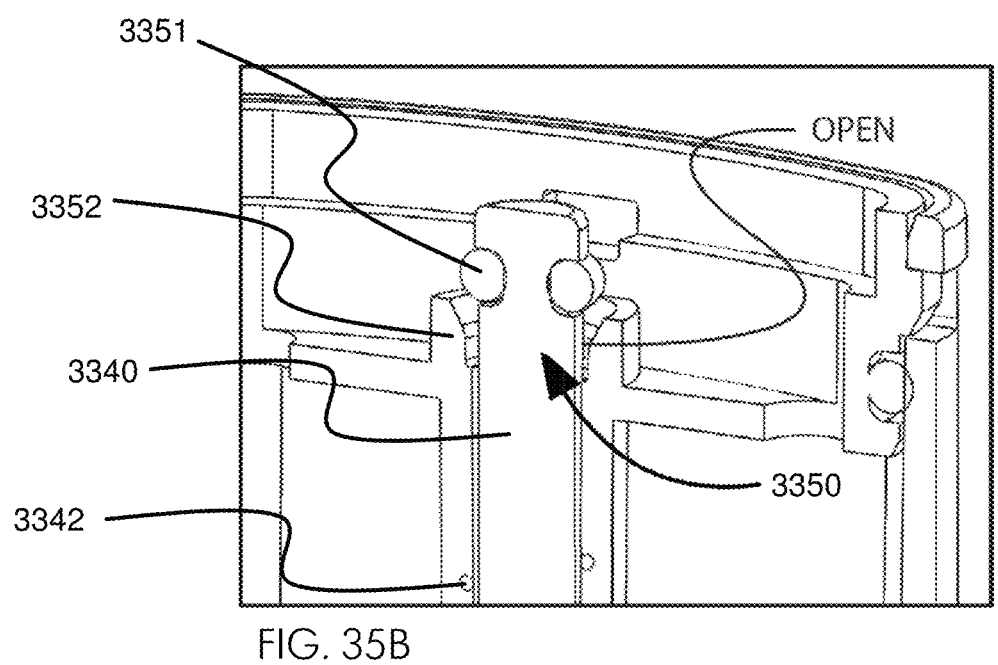

FIG. 35B illustrates the bleed valve 3350 in an open configuration. As shown, the bleed valve o-ring 3351 is lifted off the bleed valve housing 3352 opening a passageway into the body of the developer solution tank 3300, and thereby advantageously allowing the equalization of pressure within the tank body 3310 as the developer solution within the developer solution tank 3300 is dispensed.

Because the bleed valve 3350 and the dispenser valve 3330 are connected mechanically, e.g., via the connecting rod 3340, the developer solution tank 3300 may advantageously be provided with a dispensing lock to prevent accidental dispensing, e.g., during shipping or installation. In some embodiments, the dispensing lock may simply be a clip that attaches over the bleed valve 3350, e.g., lockingly engaging over the uppermost end of the connecting rod 3340. In this way, when the uppermost end of the connecting rod 3340 is locked in place, the dispenser tip 3332 of the dispenser valve 3330 may not move within the nozzle 3320 and the dispenser tip o-ring 3331 may not unseat from within the nozzle housing 3322. Thus, when the dispensing lock is in place, the developer solution tank 3300 is not capable of dispensing. The dispensing lock may be removed before the developer solution tank 3300 is used to develop a test sample, e.g., before installing the developer solution tank 3300 in a base unit.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure. Furthermore, all references cited herein are incorporated by reference in their entirety. Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Unless otherwise explicitly stated, articles such as "a" or "an" should generally be interpreted to include one or more described items. Accordingly, phrases such as "a device configured to" are intended to include one or more recited devices. Such one or more recited devices can be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

Although systems and methods for breath collection, sampling, segmentation, and analysis have been disclosed in the context of certain embodiments and examples, this disclosure extends beyond the specifically disclosed embodiments to other alternative embodiments and/or uses of the embodiments and certain modifications and equivalents thereof. Various features and aspects of the disclosed embodiments can be combined with or substituted for one another in order to form varying modes of systems and methods for breath collection, sampling, segmentation, and analysis. The scope of this disclosure should not be limited by the particular disclosed embodiments described herein.

Certain features that are described in this disclosure in the context of separate implementations can be implemented in combination in a single implementation. Conversely, various features that are described in the context of a single implementation can be implemented in multiple implementations separately or in any suitable subcombination. Although features may be described herein as acting in certain combinations, one or more features from a claimed combination can, in some cases, be excised from the combination, and the combination may be claimed as any subcombination or variation of any subcombination.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described herein should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. Certain figures are drawn and/or shown to scale, but such scale should not be limiting, since dimensions and proportions other than what are shown are contemplated and are within the scope of the embodiments disclosed herein. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

The methods disclosed herein may include certain actions taken by a practitioner; however, the methods can also include any third-party instruction of those actions, either expressly or by implication. For example, actions such as "positioning an electrode" include "instructing positioning of an electrode."

In summary, various embodiments and examples of systems and methods for breath collection, sampling, segmentation, and analysis have been disclosed. Although the systems and methods for breath collection, sampling, segmentation, and analysis have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described herein, but should be determined only by a fair reading of the claims that follow.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 V" includes "1 V." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure.

The invention claimed is:

1. A process for manufacturing a device capable of extracting an analyte of interest from a breath sample, the process comprising:
    creating a mixture that comprises a combination of reactive particles and resin particles, the reactive particles comprising a reactant capable of reacting with the analyte of interest, the reactive particles comprising an amine; and
    transforming the mixture into a solid, porous structure of a selected shape using a sintering process in which the mixture is heated, the solid, porous structure capable of extracting the analyte of interest from a breath sample passed through the porous structure.

2. The process of claim 1, wherein the reactive particles comprise functionalized silica particles.

3. The process of claim 1, wherein the resin particles comprise polyethylene or polypropylene.

4. The process of claim 1, wherein the solid, porous structure is capable of extracting and reacting with acetone in the breath sample.

5. The process of claim 1, wherein the selected shape is a disk shape.

6. The process of claim 1, wherein the mixture additionally comprises a desiccant.

7. The process of claim 1, wherein the mixture is heated during the sintering process to a temperature that exceeds a melting point of the resin particles.

8. The process of claim 1, wherein the sintering process is a laser sintering process.

9. The process of claim 1, further comprising:
    creating a second porous structure by a process that comprises (1) creating a second mixture containing resin particles and a desiccant material, and (2) transforming the second mixture into the second porous structure using a sintering process, the second porous structure configured to remove moisture from the breath sample; and
    fusing or molding together the solid, porous structure with the second porous structure to create a multi-layered structure.

10. The process of claim 1, further comprising incorporating the porous structure into a disposable cartridge that comprises a flow path, the disposable cartridge comprising a transparent window than enables visual monitoring of a color change produced by a chemical reaction involving the porous structure and the analyte of interest.

11. The process of claim 1, wherein the selected shape is a puck shape.

12. A structure for extracting an analyte from a breath sample, the structure manufactured by a process that comprises:
    creating a mixture that comprises a combination of reactive particles and resin particles, the reactive particles comprising a reactant capable of reacting with the analyte of interest, the reactive particles comprising an amine; and
    transforming the mixture into a solid, porous structure of a selected shape using a sintering process in which the mixture is heated, the solid, porous structure capable of extracting the analyte of interest from a breath sample passed through the porous structure.

13. The structure of claim 12, wherein the reactive particles comprise functionalized silica particles.

14. The structure of claim 12, wherein the resin particles comprise polyethylene or polypropylene.

15. The structure of claim 12, wherein the solid, porous structure is capable of extracting and reacting with acetone in the breath sample.

16. The structure of claim 12, wherein the selected shape is a puck shape.

17. The structure of claim 12, wherein the mixture additionally comprises a desiccant.

18. The structure of claim 12, wherein the mixture is heated during the sintering process to a temperature that exceeds a melting point of the resin particles.

19. The structure of claim 12, wherein the sintering process is a laser sintering process.

* * * * *